US008636755B2

(12) United States Patent
Berreklouw

(10) Patent No.: US 8,636,755 B2
(45) Date of Patent: Jan. 28, 2014

(54) ASSEMBLY COMPRISING A STABILISER AND AN INSTRUMENT TO BE POSITIONED IN OR AROUND A PASSAGE SURROUNDED BY BODY TISSUE

(75) Inventor: Eric Berreklouw, Son (NL)

(73) Assignee: Daidalos Solutions B.V., Son (NL)

( * ) Notice: Subject to any disclaimer, the term of this patent is extended or adjusted under 35 U.S.C. 154(b) by 1232 days.

(21) Appl. No.: 10/510,032

(22) PCT Filed: Apr. 2, 2003

(86) PCT No.: PCT/NL03/00246
§ 371 (c)(1),
(2), (4) Date: Oct. 1, 2004

(87) PCT Pub. No.: WO03/082121
PCT Pub. Date: Oct. 9, 2003

(65) Prior Publication Data
US 2005/0228410 A1   Oct. 13, 2005

(30) Foreign Application Priority Data
Apr. 2, 2002  (NL) .................................. 1020288

(51) Int. Cl.
*A61B 17/08* (2006.01)
(52) U.S. Cl.
USPC ........................................................ 606/153
(58) Field of Classification Search
USPC ................. 606/131–150, 151–158, 115, 123, 606/213–221; 623/1.23; 601/6, 7; 604/35
See application file for complete search history.

(56) References Cited

U.S. PATENT DOCUMENTS

| | | | | |
|---|---|---|---|---|
| 5,154,723 A * | 10/1992 | Kubota et al. | ................. | 606/130 |
| 5,695,504 A * | 12/1997 | Gifford et al. | ................ | 606/153 |
| 5,725,553 A * | 3/1998 | Moenning | ..................... | 606/213 |
| 5,891,159 A * | 4/1999 | Sherman et al. | .............. | 606/144 |
| 6,032,672 A * | 3/2000 | Taylor | ........................... | 128/898 |
| 6,033,375 A * | 3/2000 | Brumbach | ....................... | 604/22 |
| 6,547,724 B1 * | 4/2003 | Soble et al. | .................... | 600/156 |
| 6,575,168 B2 * | 6/2003 | LaFontaine et al. | .......... | 128/898 |
| 6,626,918 B1 * | 9/2003 | Ginn et al. | .................... | 606/148 |
| 6,740,098 B2 * | 5/2004 | Abrams et al. | ................ | 606/148 |
| 7,338,505 B2 * | 3/2008 | Belson | ........................... | 606/150 |
| 2002/0095147 A1 * | 7/2002 | Shadduck | ........................ | 606/41 |

FOREIGN PATENT DOCUMENTS

WO        0215796        2/2002

OTHER PUBLICATIONS

European Office Action dated Mar. 24, 2010 from EP03745482.4.

* cited by examiner

*Primary Examiner* — Melanie Tyson
(74) *Attorney, Agent, or Firm* — Young & Thompson

(57) ABSTRACT

An assembly includes a stabilizer and an instrument to be positioned in or around a passage surrounded by body tissue, in particular vascular tissue. The stabilizer is provided with a loop-shaped suction nozzle, which nozzle can be operationally connected to suction elements in order to suck tightly to tissue close to and around the passage. The instrument has a head section for performing operations on vascular tissue.

24 Claims, 21 Drawing Sheets

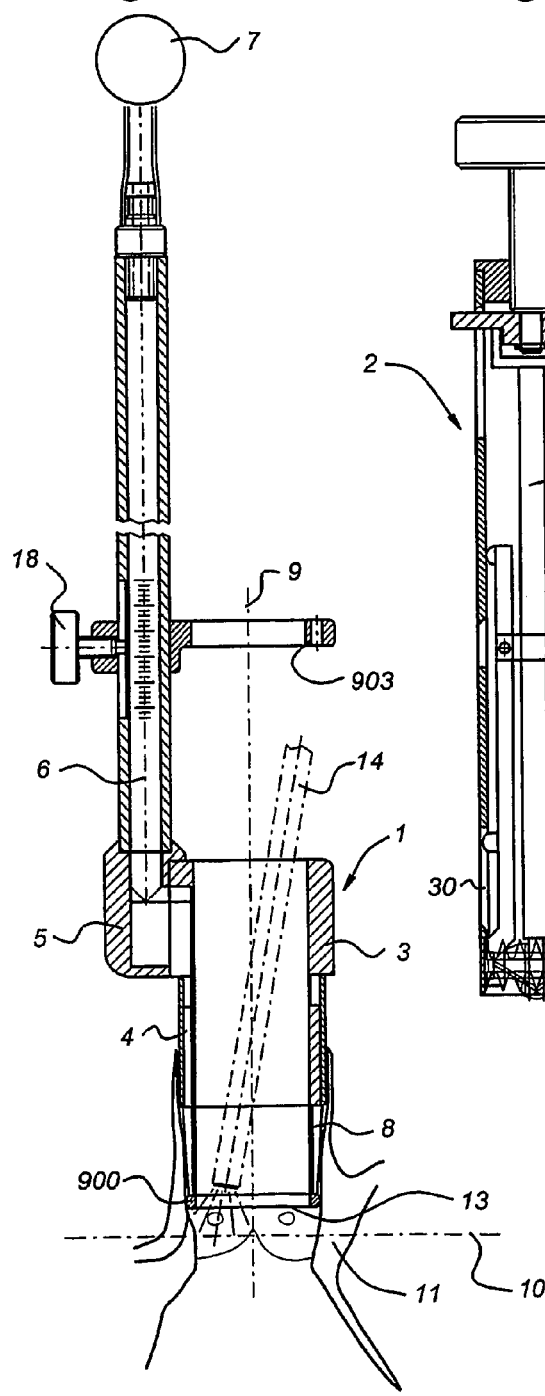

ASSEMBLY COMPRISING A STABILISER AND AN INSTRUMENT TO BE POSITIONED IN OR AROUND A PASSAGE SURROUNDED BY BODY TISSUE

The present invention relates to an assembly comprising a stabiliser and an instrument to be positioned in or around a passage surrounded by body tissue, in particular vascular tissue. According to the invention an instrument is understood to be not only a tool, appliance or implement, but also an aid in the general sense. In the assembly according to the invention the instrument is in particular an applicator for positioning and fixing a fixing device in or around the passage, the applicator having a head section that is equipped for carrying and releasing the fixing device. According to the invention, the instrument can also be the fixing device itself, or according to the invention at least the fixing device can also be part of the instrument.

According to the invention, a fixing device is in particular understood to be an accessory that at one end is fitted in or around the passage surrounded by body tissue and to which an object is fixed or can be fixed at the other end. The object can thus clearly already have been fixed, for example integrated with the fixing device, for example in the factory, before fitting of the fixing device in or around the passage surrounded by body tissue, but can clearly also be fixed to said fixing device only after the fixing device has been fitted in or around the passage surrounded by body tissue. The additional object can also be, in particular, a cardiac fixing device, such as for an artificial valve or biological donor valve, a vessel fixing device, such as for an artificial vessel or donor vessel, a working duct, access port or a further accessory. The accessory is, as it were, a connector by means of which "something" can be secured in or around a passage surrounded by body tissue. In this respect the fixing device could possibly also be termed a connector.

Conventionally, the positioning of a fixing device in a passage surrounded by body tissue, such as vascular tissue, is usually carried out manually in practice, by suturing the prosthetic fixing device in the passage. Consideration can be given, for example, to the positioning of an artificial heart valve, making a vessel join between an artificial vessel or natural vessel and, for example, a coronary artery. Nowadays the requisite "mechanically anchoring" fixing devices are known which, at least in the meaning given to "mechanically anchoring" here, no longer require manual suturing. Such mechanically anchoring fixing devices also make so-called minimally invasive techniques possible in the field of heart operations, or at least should make this possible, it no longer being necessary to open the chest to expose the heart. In particular in the case of the heart and also in the field of vessel anastomoses the problem arises with these devices that the accuracy with which the fixing device is positioned in the correct location is extremely important and that the means with which the fixing device is positioned tend to shift this location, for example to push it along. In the case of a beating heart, there is also the problem that this location moves as a consequence of the beating of the heart. All of this means that such so-called "mechanical fixing devices" still find little or no practical use, especially in minimally invasive operations.

A system for vacuum-assisted remote suturing for securing a heart valve fixing device is disclosed in WO 00/59382. This system consists of a tube with a closed distal end directed to the heart. This tube is preferably also closed at the opposing, proximal end. This tube is provided with an annular opening extending around the entire periphery some distance away from the distal end. By now applying vacuum to the tube, tissue that is on the outside of said tube around said annular opening is drawn into the tube. By now moving needles fitted distally from the annular opening in the axial, proximal direction, this tissue drawn into the tube is pierced by said needles. The corollary of the various aspects is that the distance from the annular suction opening in the tube to the closed distal end must be at least equal to the length of the needles used. According to page 12, lines 16-18 of WO 00/59382, these needles have a length in the range of 35-40 mm. This single distance is thus a significant distance, certainly in the field of heart valve operations, to which said WO 00/59382 relates in particular. This significant distance between the suction ring and the distal end implies that the closed distal end will protrude to well beyond the location in which the natural heart valve is fixed, which natural heart valve therefore has to be removed beforehand. This makes it completely impossible to perform repair operations on the natural heart valve using the system as disclosed in WO 00/59382. In the case of repair operations consideration can be given, for example, to a so-called ring fixing device that is used to constrict the passage for the bloodstream at the heart valve, to repair, for example, a leaking heart valve. Moreover, the fact that the distal end of the tube in the system from WO 00/59382 is closed males it completely impossible to use this system for positioning a fixing device. This is because the tube will continue past the entire location for fixing the fixing device and, as a consequence of the closed distal end, will no longer be able to be removed after fixing a fixing device in place, or at least will not be able to be removed without removing said fixing device at the same time. Moreover, for fitting the fixing device in position it will be necessary to interrupt the vacuum suction at the annulus, and the tissue surrounding the suction nozzle will thus be released. What is disclosed in WO 00/59382 can thus be used only for the intended purpose described in this publication, that is to say the preparation of a suture join by inserting the sutures in an automated manner through the tissue at the location of the passage, for subsequent fixing of the fixing device.

U.S. Pat. No. 6,071,295 discloses a device for keeping motionless the surface of the heart where an anastomosis for a bypass with a coronary artery has to be produced. This is effected by sucking the surroundings of the receiving target vessel tightly to a vacuum system around the location where an anastomosis (join between graft vessel and target vessel) has to be produced. The surgeon will then produce the anastomosis by hand by suturing the graft vessel to the target vessel.

The aim of the present invention is to make it possible for a fixing device to be positioned with high accuracy in or around a passage surrounded by body tissue, in particular vascular tissue.

According to a first aspect of the invention this aim is achieved by providing an assembly comprising a stabiliser and an instrument to be positioned in or around a passage surrounded by body tissue, in particular vascular tissue, wherein the stabiliser is provided with one or more suction nozzles running in the shape of a loop, which suction nozzles can be operationally connected to suction means in order to suck tightly to tissue close to and around said passage, which may still have to be made; wherein the instrument has a head section for performing operations on vascular tissue and wherein the stabiliser and the instrument are provided with, respectively, an instrument stop provided on the stabiliser and a stabiliser stop provided on the instrument, which, in the stop position when they are in contact with one another, unambiguously define the position of the head section with respect to the position of the loop shape.

According to the invention the instrument is, in particular, an applicator for positioning and fixing a fixing device in or around the passage, the head section being equipped for carrying and releasing the fixing device.

According to the invention the stabiliser ensures, by means of the suction nozzles, that tissue around and close to the passage is sucked on tightly. By means of the instrument the head section can then be positioned in or with respect to the passage. With this arrangement the head section of the instrument can optionally also be in or close to the suction nozzles, running in the shape of a loop, in advance, but will preferably be brought into or close to said loop shape after the stabiliser has sucked the tissue tightly. In order to be able to guarantee the desired accuracy of positioning with this arrangement, the instrument and the stabiliser are provided with, on the one hand, a stabiliser stop provided on the instrument and, on the other hand, an instrument stop provided on the stabiliser. These stops are intended to engage on one another and in the position in which they engage on one another unambiguously define the position of the head section of the instrument with respect to the position of the loop shape. In this way it can be ensured that the operation to be performed is performed, or in the case of an applicator the fixing device is positioned and fixed, at a distance from the suction nozzles running in the shape of a loop which is determined by the stops. In the stop position it is thus ensured that the instrument to be used, in particular the applicator, assumes a fixed, unchangeable position with respect to the suction nozzles and thus also with respect to the location for fixing the fixing device. A high accuracy can be achieved in this way.

Using an assembly according to the invention fixing devices can be used to secure mechanical, animal or human valves, but also to produce vessel joins between natural and/or synthetic vessels. Vessel joins can be, inter alia, end-to-end, end-to-side or side-to-side. The said fixing devices can also be used to position (temporary) ports that can be closed off by a cap, closures, (temporary) working ducts or (temporary) cannulas. Using an assembly according to the invention it is, for example, possible to position and fix fixing devices as disclosed in WO 00/24339 and WO 00/44311, both in the name of the same Applicant as the present application. Such fixing devices are of the type having a tubular member provided with flange fingers or arms with pins pointing outwards arranged distributed around the periphery of the tubular member, which flange fingers or arms with pins, prior to anchoring in the tissue, are in a straightened position to produce a slim shape, in which straightened position the projection of the respective flange fingers or arms is located on a radial transverse surface of the tubular member essentially on or within the periphery of the tubular member. The assembly according to the invention can, however, also very suitably be used for positioning very many other fixing devices known from the state of the art in or around a passage surrounded by body tissue.

In the case of the assembly according to the invention it is readily conceivable that the instrument stop and stabiliser stop are firmly fixed, to all intents and purposes in advance in the factory, to the stabiliser and applicator, respectively, so that the position of the applicator head with respect to the position of the loop shape of the suction nozzle(s) in the stop position is predetermined, to all intents and purposes in the factory. For example, this is conceivable when using the assembly according to the invention to produce anastomoses. The disadvantage of this is, however, that in this way it is not possible to make adjustments to especially the geometry of the patient. A further disadvantage is, moreover, that the corollary of the various features is that it is necessary to work very accurately when producing the suction connection between the suction nozzles and the tissue surrounding the passage. Although this can be achieved it is not very practical since it could soon degenerate into an iterative mechanism of sucking tightly, checking the position of the suction hold, terminating the suction hold, sucking tightly again, checking the position of the suction hold, etc. In order, on the one hand, to enable adaptation to the geometry of the patient concerned and, on the other hand, to render an iterative fixing process superfluous, it is advantageous according to the invention if the stabiliser is provided with a guide on which the instrument stop is fitted such that it can slide along the guide and with respect to which the instrument stop can be locked, if the guide has a direction of extension essentially transverse to the loop shape, and if the one or more suction nozzles running in the shape of a loop and the guide are firmly linked to one another in such a way that the mutual positions of the loop shape and guide are fixed with respect to one another.

It then becomes possible first to fix the stabiliser in place by sucking the tissue tightly by means of the suction nozzles and then to measure the distance between the location in which the stabiliser is sucked on tightly, on the one hand, and the location for fixing the fixing device, on the other hand, and to set the instrument stop along the guide of the stabiliser on the basis of this distance. It is pointed out that it is also possible, completely within the scope of the invention, to adjust the stabiliser stop provided on the applicator along a guide instead of providing and adjusting the instrument stop along a guide, or to make both adjustable along a guide. To facilitate setting of the instrument stop (or optionally the stabiliser stop) along the guide it is advantageous according to the invention if the guide is provided with a scale with a zero point and if the distance from the zero point to the loop shape is chosen such that when, on the one hand, the instrument stop is aligned with the zero point and, on the other hand, the instrument stop and stabiliser stop are in the stop position, the head section, or at least a fixing device provided thereon, is located at the distal bottom end of the stabiliser. After the stabiliser has been sucked tightly to the tissue, this distal bottom end of the stabiliser can easily be observed by means of, for example, an endoscope or other instrument, so that the distance from said bottom end to the desired location for the fixing device can easily be measured by means of the endoscope or other instrument. Instead of making use of an endoscope for this measurement and/or the positioning of the stabiliser, instrument, fixing device and/or tissue, it would, for example, also be possible to make use of real and/or virtual two- or three-dimensional imaging, it optionally being possible to make use of, for example, echographic sound waves, X-ray examination, computer tomography, magnetic resonance, electromagnetic techniques or another imaging technique and/or computer-controlled navigation system, optionally in combination with the measurement instrument described below. It is also possible that prior to or during the operation markers are placed at the location of the target area or at a fixed distance and position therefrom, such that stabiliser, instrument, fixing device and/or tissue can be positioned in the desired location, optionally making use of imaging techniques, including computer-controlled navigation systems.

The idea here is that one or more markers are placed at the location of the target or landing area, usually tissue, and one or more markers are also placed on the fixing device, applicator, instrument, stabiliser and/or tissues to be moved. By virtually and/or actually moving the markers on the target area and the markers on the said accessories, tissues or instruments towards one another, it is possible to bring the markers into contact and/or to make them overlap one another and/or to bring the markers to a predetermined distance and/or position away from one another, the desired positioning of target area and said instrument, tissues and/or accessories being achieved, after which an operation can take place, such as, for example, the ejection of a fixing device. In this context the functions of target marking and what we will now for simplicity term moving part marking can also be reversed or relate to two moving (groups of) markers; after all, the point at issue is that both (groups of) markers can be brought towards one another into a desired position, it being possible to bring the parts on which these (groups of) markers have been placed not only the desired distance apart but also into the mutual angular and/or rotational position. Thus, for example, in the case of a valve operation the location of the target or landing area for the fixing device, stabiliser, instrument, applicator or accessory, in this case usually the region of or around the valve annulus, can be marked with one or more markers in advance or during the operation. Markers can consist of so-called LEDs (light emitting electrodes) which emit infrared light and can be detected by cameras suitable for this purpose. However, this marking could also be effected by fitting one or more very small coils (a few millimeters in size) at the location, which coils can be pressed into the tissues at that location, for example using very small pins, and can be detected in an electromagnetic field or fields and/or a navigation system that makes use of electromagnetic field. Such markers can be placed from inside the bloodstream but also from outside, for example by fitting such a small coil-shaped marker on a sort of pin and/or placing at a specific distance from and in a specific position with respect to the target area. In the case of a replacement of the tricuspid aortic valve it is then possible, for example to place three markers approximately 120 degrees apart. In the case where a fixing device or a valve prosthesis of flat construction has to be positioned at the location of the aortic valve annulus, three such markers approximately 120 degrees apart could, for example, be placed, for example in the vertical plane halfway between the tops of the commissura and the troughs of the valve leaf sinuses, so that the valve prosthesis can be positioned precisely midway between them. When positioning a fixing device or heart valve prosthesis of sinusoidal shape it is then possible, for example, to place three markers 120 degrees apart precisely at the location of the remnant of the original valve annulus. In the case of a mitral valve operation it is then possible, for example, to place one marker at the location of each of the two commissura and one marker at the location of the annulus in the centre of the rear valve leaf, but other numbers and positions are possible. Placing markers prior to the operation can be effected via an intravascular catheter which is operated remotely, but can also be achieved by placing one or several markers transthoracically percutaneously on, at or via the outside of heart, blood vessel or other hollow organ at the location of the target area. When placing markers use can also be made of one or more stabilisers, working ducts, applicators and/or instruments according to the invention. In the case of vessel joins, such as, for example, in coronary bypass operations, one or more markers can be placed around the existing opening, or the opening to be made, in the target vessel, which markers can also be positioned in the shape of a loop. In this context such markers can be used to navigate the said instruments and/or another vessel (the donor vessel) to the desired (target) blood vessel and/or to the desired target area at the location of the blood vessel itself, such as the existing opening, or opening that has been made or is still to be made, of or in the wall of said blood vessel. As has been stated, markers can also be placed on the said instruments and aids, including also on detachable components thereof, it being possible for the markers themselves also to serve as target markers for other instruments or aids. Such markers can also have been fitted on the suction nozzles of a stabiliser and fixed by an adjustment mechanism of the stabiliser, by suturing, stapling, mechanical compressive or tensile forces, but also by other fixing techniques such as are disclosed in WO 00/24339 and WO 00/44311, both in the name of the same Applicant as the present application, or gluing or combinations of fixing techniques. The markers can be removed again or left in the body. The latter is certainly possible if these markers no longer come into contact with the bloodstream, when they are separated from the bloodstream because they are, for example, covered by the wall of a fixing device, such as, for example, a valve prosthesis fixing device.

Positioning of the bottom edge of the stabiliser on a recognisable anatomical structure can likewise be facilitated if, for example, sutures on mechanical grippers are placed at the location of said structure, which sutures can be joined to the bottom edge and/or wall of the stabiliser a fixed distance away. Thus, for example in the case of an aortic valve replacement, three traction sutures can be placed at the location of the three commissura which sutures are fed through or in contact with the wall of the stabiliser, such that the bottom edge of the stabiliser is in contact with the commissura or a fixed distance away therefrom.

Sensors can also be fitted on the stabiliser, instrument and/or fixing device for positioning these components in the desired location. Such sensors can, for example, consist of contact sensors, to establish that there is tissue contact, pressure sensors, to, for example, position the prosthesis in the region with the smallest passage diameter when implanting a valve prosthesis, or flow sensors, to, for example, position a vessel fixing device precisely along the longitudinal axis of a blood vessel, or sensors which in some other way give an impression of the anatomy of the target area at that location.

It should be clear that said navigation methods, with the aid of markers and/or sensors, can also be used in the case of other interventions in the human and/or animal body, even without the said assembly of stabiliser and instrument.

So as to facilitate the introduction of the stabiliser into a blood vessel or elsewhere in the body and when working with the instrument, for example an applicator, not to be hindered too much by surrounding tissue, it is preferable according to the invention if the stabiliser comprises a working duct with the one or more suction nozzles running in the shape of a loop at the distal end. This working duct can be regarded as a tube through which the instrument, for example an applicator, is then inserted or at least can be inserted. With this embodiment the guide will preferably have been provided at the proximal end of the working duct so that the guide is accessible for adjusting the instrument stop along it without coming too close to the location for fixing the fixing device. Furthermore, part of the suction line for applying a vacuum to the suction nozzles will advantageously be accommodated in the wall of the working duct.

According to the invention it is advantageous if the one or more suction nozzles running in the shape of a loop comprise one or more axial suction nozzles opening in the axial direction viewed with respect to the loop shape. This is useful for holding the so-called target vessel by suction when producing so-called "end-to-side" anastomosis. However, this is very particularly advantageous when using the assembly according to the invention for fitting a mitral valve or tricuspid valve.

This is because when fitting such valves the suction nozzles can then adhere by suction to the heart atrium tissue.

According to the invention it can furthermore be advantageous if the one or more suction nozzles running in the shape of a loop comprise one or more radial suction nozzles opening in the radially outward direction, viewed with respect to the loop shape. This is useful, inter alia, when positioning a fixing device in a blood vessel. For example, when producing an "end-to-end" anastomosis it can be useful if the stabiliser is able to attach by suction inside one of the blood vessels on the inside wall thereof. Furthermore, such a positioning of the suction openings is also suitable for positioning a fixing device for the aortic valve. This is because the suction nozzles can then suck tightly to blood vessel tissue that essentially is located around the suction nozzles like the inside wall of a hose.

According to the invention it can furthermore be advantageous if the one or more suction nozzles running in the shape of a loop comprise one or more radial suction nozzles opening in the radially inward direction, viewed with respect to the loop shape. This is useful, inter alia, when positioning a fixing device on or around the outside of a blood vessel, or other hollow organ, it being possible for the suction nozzles to have a completely or partially cylindrical shape.

According to the invention it can furthermore be advantageous if the one or more suction nozzles running in the shape of a loop comprise one or more inclined suction nozzles opening outwards obliquely with respect to the axial direction, viewed with respect to the loop shape. As a consequence of the geometry of the heart, this is particularly useful when positioning a fixing device for the mitral and tricuspid valve prosthesis. Here the slope could be, in particular, approximately 45°. Furthermore, for use for a mitral or tricuspid valve, it will be advantageous here if axial suction nozzles are provided in addition to inclined suction nozzles.

According to a further embodiment of the invention it is possible to make the entire or partial part of the stabiliser with the suction nozzle or nozzles such that it can be uncoupled from the rest of the stabiliser. This can, for example, be very useful if following the intervention it is no longer possible easily to remove this suction nozzle section of the stabiliser from the body or it is possibly deliberately desired to leave this suction nozzle section in the body so that the uncoupled section, after it has been fixed to the body or organ, can remain behind as a functional or non-functional implant. This uncoupled part or these uncoupled parts of the stabiliser can be fixed to the tissues by, for example, suturing, mechanical fixing techniques, including those as described in WO 00/24339 and WO 00/44311, both by the same Applicant as the present application, tissue adhesive, other fixing techniques or combinations of these techniques.

In particular for fitting so-called ring prostheses, or at least the fixing device thereof, it is advantageous according to the invention if the suction nozzles are provided on at least two, preferably three, four, five or six or possibly more, segments defining the loop shape and if a number of said segments, preferably all said segments or all said segments bar one are adjustable in the radial direction, viewed with respect to the loop shape, by means of an adjustment mechanism in order to constrict or widen the passage, after having sucked the tissue close to the passage tightly all round, by adjusting a number, in particular all, of the adjustable segments inwards or outwards, respectively. What is usually concerned in the case of a so-called ring prosthesis is constriction of the passage for the bloodstream close to the heart valve concerned in order to repair a leaking valve. To this end a so-called ring prosthesis which has a desired narrower passage than the locally widened bloodstream is usually fitted within the bloodstream. In order then to bring the wall of the bloodstream into contact with the ring prosthesis, or at least the fixing device thereof, in order to be able to anchor the ring prosthesis or fixing device in said wall and to keep the wall permanently in a constricted state, it is advantageous if the suction nozzles in the wide state are able to grip the vascular wall firmly so as then to be able to pull said vascular wall inwards towards the ring prosthesis or fixing device to be fitted. Adjustable suction nozzles of this type can also be advantageous when fitting ordinary valve prostheses. Thus, for example, it is possible if the fixing device or prosthesis is somewhat too small compared with the passage in the bloodstream at that location, to pull the vascular wall at that location into contact with the outer periphery of the fixing device before anchoring the fixing device in the wall of the bloodstream. Adjustability of the suction nozzles can, incidentally, also be useful for first gripping the vascular wall firmly and then widening the passage of the bloodstream at that location by moving the adjustable suction nozzles apart. This can be useful, for example, if the fixing device or prosthesis to be fitted is somewhat larger than the passage for the original bloodstream at that location. In general, the adjustable segments with suction nozzles make it possible for the shape, that is to say not merely the diameter, of the passage in the tissue to be made to match the fixing device or prosthesis to be fitted.

According to the invention, the loop shape in which the suction nozzles are arranged can assume very diverse shapes. In particular, said loop shape will have a ring-shaped or circular or ellipsoidal or oval-like or completely or partially tubular or saddle-shaped or 3-fold sine shaped or bean- or kidney-shaped contour. The saddle-shaped contour is particularly useful when producing so-called "end-to-side" anastomoses or "side-to-side" anastomoses. The 3-fold sine-shaped contour can be useful in particular when positioning a fixing device for an aortic valve where the so-called annulus has a corresponding three-fold sine-shaped pattern. The bean- or kidney-shaped contour can be useful in particular when positioning a fixing device for a mitral or tricuspid valve where the so-called annulus has a corresponding bean- or kidney-shaped pattern.

In order to achieve good contact of the suction nozzle on the tissue, the suction nozzle can be of completely open construction, but the shape of the suction nozzle according to the invention can also be like a casting of the shape of the tissue against which the suction nozzle has to be positioned. The shape of such a casting can be determined on the basis of the average shape of the structure against which the suction nozzle comes into contact, but can also be achieved by providing the suction nozzle on the suction side with a gas-permeable, deformable membrane that is made of a material that is flexibly resilient material without being deformed by the vacuum force, such as, for example, flexible metals or plastics. It is also possible on the basis of per- and/or pre-operative exploratory investigation to provide the suction nozzle pre- or per-operatively, optionally custom-made, with a shape that is unique to the tissue of that patient, so that optimum contact of the suction nozzle on that patient's tissue can be achieved. This applies the more so insofar as the suction nozzle section remains behind in the body as a functional implant.

In the case of the use of a suction nozzle for stabilisation of a coronary artery, which is not or cannot be freed from the surrounding tissue, the shape of such a suction nozzle can also be fairly flat, the stabiliser stabilising not only the coronary artery but also part of the surrounding epicardial tissue.

According to a more detailed embodiment it is, in particular, advantageous if the suction nozzle consists of parts or segments that can be coupled to one another. Especially in the case of vessel joins it can be advantageous first to provide the individual vessels with suction nozzle parts and subsequently then to join the suction nozzle parts together. Insofar as that involves a vessel that is attached at both ends and it is desired to fit a suction nozzle around the entire periphery of such a vessel, suction nozzles of this type must consist of several parts or segments that can or cannot be coupled to one another.

According to a more detailed embodiment it is, in particular, advantageous if the assembly according to the invention comprises an applicator for, in particular provided with, a fixing device of the type comprising a tubular member provided with pins arranged distributed around the periphery, each pin being arranged on an arm that is attached by one end to the tubular member in a manner which permits swinging about a hinge axis, and the arms and pins being movable, by swinging about the hinge axis, from an insertion position, in which they are located essentially inside the tubular member, into a fixing position in which at least the pins, viewed in the radial direction, project outside the tubular member in order to penetrate the surrounding vessel wall tissue. A fixing device of this type is the subject of Sections 1.2, 2.2, 3.2 and 4.2 of the Applicant's WO 00/44311, which has already been mentioned.

According to a further advantageous embodiment, the assembly according to the invention comprises an applicator for, in particular provided with, a fixing device of the type having a tubular member, which member is provided with flange fingers arranged distributed around the periphery of the tubular member, in particular distal and optionally proximal flange fingers, which flange fingers, in particular at least the distal flange fingers, and preferably the distal and proximal flange fingers, can be or have been reversibly bent, against a resilient force, from a position projecting outwards with respect to the tubular member into a straightened position in which the projection of the respective flange fingers is located on a radial transverse surface of the tubular member essentially on or within the periphery of said tubular member. Fixing devices of this type are disclosed, in particular in WO 00/24339 and WO 00/44311, both in the name of the same Applicant as the present application. As far as the fixing devices are concerned, these two WO applications are therefore also incorporated in the present application by reference. WO 00/24339 relates in particular to vessel fixing devices and specifically in particular to coupling means for joining to one another blood vessels and/or vessel fixing devices or other types of tubular ducts or organs in the human or animal body. WO 00/44311 has four sections, the subject of all of which is fixing devices where the assembly according to the present invention can be used for the positioning thereof.

In this context it is furthermore advantageous if the applicator comprises:
- an elongated support member with, at the distal end thereof, a support ring that fits inside the tubular member of the fixing device, which support ring has an external peripheral surface suitable for supporting the tubular member;
- an obstructing member that can be moved parallel to the elongated support member from an obstructing position at least partially overlapping at least the straightened, distal flange fingers into a release position completely exposing said flange fingers.

According to a second aspect the present invention relates to an applicator, in particular intended for use with an assembly according to the first aspect of the invention, comprising:
- an elongated support member comprising two, three or more gripper arms that run parallel to the support member, are arranged distributed around the support member and are fixed to the support member such that they can pivot about a pivot point, which gripper arms have free gripper ends that fit in the tubular member of the fixing device, it being possible to tilt the gripper arms with respect to the longitudinal axis of the support member about the pivot point between, on the one hand, a gripping position located radially outwards and gripping the tubular member by the outer surface of the gripper ends from the inside and, on the other hand, a release position moved radially inwards that releases the tubular member; and
- an obstructing member in the form of a sleeve running around the gripper arms, which sleeve can be moved parallel to the gripper arms from an obstructing position surrounding the tubular member and straightened fingers, such as flange fingers, provided thereon, in the proximal direction into a release position completely exposing the tubular member and flange fingers provided thereon.

Using an applicator of this type it is possible to position a fixing device with anchoring fingers, such as, for example, flange fingers, which, prior to positioning, are held in the straightened position by an exterior sleeve, from some distance away, for example 10 cm or more. Whilst the gripper arms hold the fixing device in place, the sleeve can then be slid away in order to release the fingers held straight by the sleeve and to allow these fingers to pivot outwards for anchoring in the surrounding vessel wall tissue. After the sleeve has been slid away and the fingers have anchored themselves, the gripper arms can then be tilted about their respective pivot point in such a way that the gripper ends move towards one another in the radially inward direction so as to release the tubular member and then to be able to be removed from the tubular member.

According to the second aspect of the invention it is in particular advantageous if the gripper arms each comprise a distal arm section located on the distal side of the respective pivot point and a proximal arm section located on the proximal side of said respective pivot point, if the proximal arm sections are provided with tensioning means that hold the proximal arm sections together towards one another in the radial direction, at least in the gripping position, and if the distal arm sections are each provided with a distal projection that faces radially outwards and extends into the wall of the sleeve; and if the sleeve is provided, per distal projection, with a distal longitudinal slot opening to the inside, into which, in the gripping position, one distal projection extends in each case, the various features being such that when the sleeve is moved so far in the proximal longitudinal direction with respect to the gripper arms that the distal projections leave the longitudinal slots and the gripper ends move inwards in the radial direction to reach the release position. The tensioning means can be, for example, springs here. By now moving the sleeve the distal projections will, if there is adequate movement in the proximal direction, leave the respective distal longitudinal slot and then be pushed inwards by the inside wall side of the sleeve so as thus to move the gripper ends on the gripper arms towards one another in the radial direction and to release the fixing device. Thus, with a suitable construction of the various features it is possible to provide that the sleeve, on moving in the proximal direction, first releases the fingers and then, on further movement in the proximal direction, brings the gripper arms into their release position. This can be achieved with a single uninterrupted movement in the proximal direction. It is pointed out that the distal longitudinal slots can be slots which completely penetrate the wall of the sleeve in the radial direction. Furthermore, it is pointed out that where a distal longitudinal slot is mentioned here this refers, in the broad sense, to a local widening of the interior space in the sleeve at the location of the distal projection, when the gripper arms are in the gripping position. It is thus also conceivable that the sleeve is completely closed and on the inside has a smooth surface except for a few ribs, which ribs then press the distal projections radially inwards on proximal movement of the sleeve.

The operational reliability of the applicator according to the second aspect of the invention can be ensured to a large extent if the tensioning means comprise a proximal projection per gripper arm, which proximal projection, in the gripping position, is in contact with the interior surface of the sleeve, and if the sleeve is provided, per proximal projection, with a proximal slot that in the gripping position is located a distal distance away from said proximal projection and opens to the inside, or at least a local proximal widening of the interior of the sleeve, in which slot or widening said respective proximal projection can be accommodated when the gripper arms reach the release position. It is pointed out that here everything can be reversed completely within the scope of the invention, in the sense that the proximal projection is provided on the interior of the sleeve instead of on the gripper arm, the requisite widening then being obtained when the proximal projection provided on the interior of the sleeve loses contact with the gripper arm. The said widening is needed to make it possible for the proximal ends of the arms to pivot outwards, the distal ends of the arms then pivoting inwards to bring the gripper ends into the release position. Here the task of the proximal projection is to hold the gripper arms in their gripping position, in particular to hold them immobile, as long as the sleeve is not moved. On adequate proximal movement of the sleeve with respect to the gripper arms, the contact between the proximal projection and the inside wall of the sleeve or between the proximal projection and the gripper arm will be lost, after which the gripper arm now obtains precisely the space required to allow the gripper ends to move radially inwards to release the fixing device.

According to the invention simple and reliable operation of the applicator, in particular proximal movement of the sleeve with respect to the support member, can be achieved if the support member and the sleeve are secured against mutual rotation about the common longitudinal axis by securing means and if the proximal end of the support member and the proximal end of the sleeve are joined to one another by screw means comprising a threaded bolt, such that turning of the threaded bolt results in movement of said sleeve and the support member in the longitudinal direction with respect to one another. To enable turning of the threaded bolt this can be provided with a rotary knob or an engagement point for an operating tool.

According to a third aspect the present invention relates to an applicator, in particular intended for use with an assembly according to the first aspect of the invention, the applicator being an applicator in accordance with one of the claims of NL Patent 1018302, which applicator is provided with a stabiliser stop. NL patent 1018302 is in the name of the Applicant and was published on 17 Jul. 2001 and is integrally incorporated in the present application by reference.

According to the third aspect of the invention the present invention furthermore also relates to an applicator according to the invention which is provided with a fixing device of the type described in Claim 18 of the present application fitted thereon, the distal flange fingers and preferably also the proximal flange fingers being in the straightened position. In order to restrict the actions on the part of the specialist or surgeon to a minimum and also to be able to preclude errors or incompleteness in such actions, it is advantageous to market the applicator with the fixing device to be positioned already fitted under tension therein in advance in the factory.

Where the terms "distal" and "proximal" are used in the present application in relation to the instrument or the stabiliser, "distal" means the end that, when the assembly is in use, faces away from the surgeon or specialist and faces towards the patient and "proximal" means the end that during use faces towards the surgeon or specialist and faces away from the patient.

The present invention will be explained in more detail below with reference to illustrative embodiments shown in the drawing. In the drawing:

FIG. 1 shows an assembled longitudinal section of an assembly according to a first aspect of the invention with an applicator according to the second aspect of the invention;

FIG. 1*a* shows a detail of the movable instrument stop of the stabiliser according to FIG. 1;

FIG. 2 shows a longitudinal sectional view of the stabiliser of the assembly according to FIG. 1;

FIG. 3 shows a longitudinal sectional view of the applicator according to the second aspect of the invention as shown for the assembly according to the invention according to FIG. 1, the applicator being shown in the so-called obstructing position;

FIG. 4 shows a longitudinal section of the applicator according to the FIGS. 1-3, the applicator being shown in a release position completely exposing the flange fingers;

Figure 5:
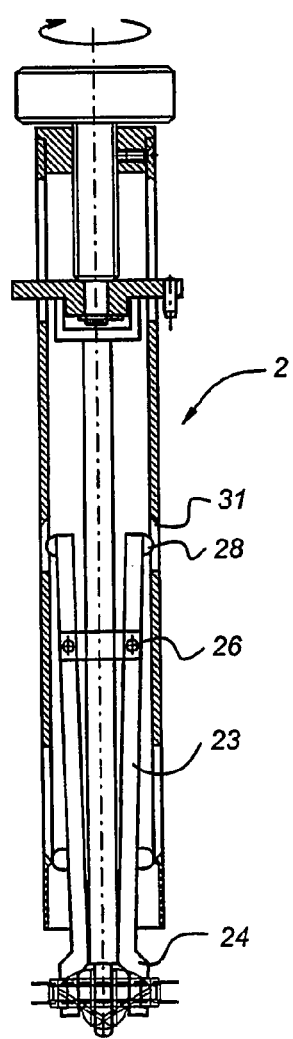
FIG. 5 shows the applicator according to FIGS. 1-4 in longitudinal section, the applicator being shown in the release position.
Figure 6A:
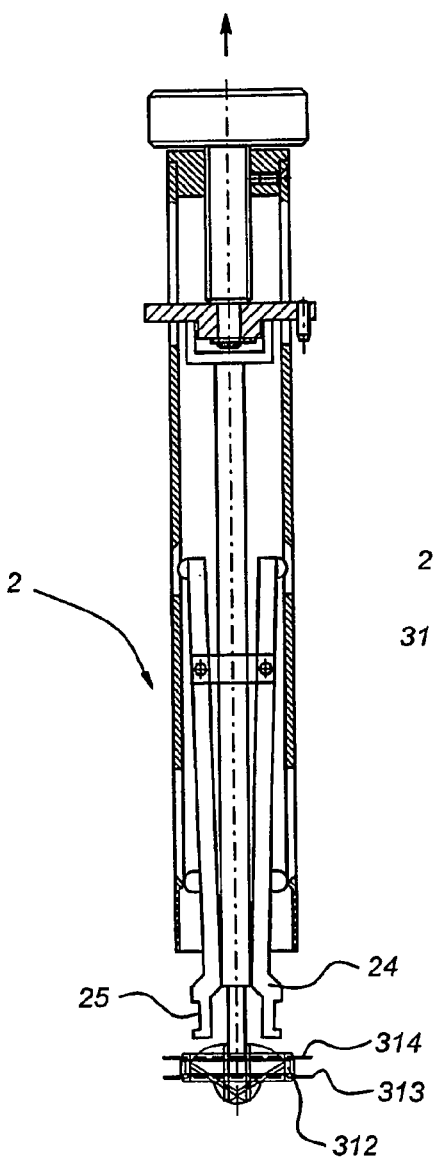
Figure 6B:
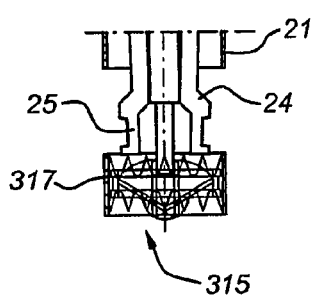
Figure 7:
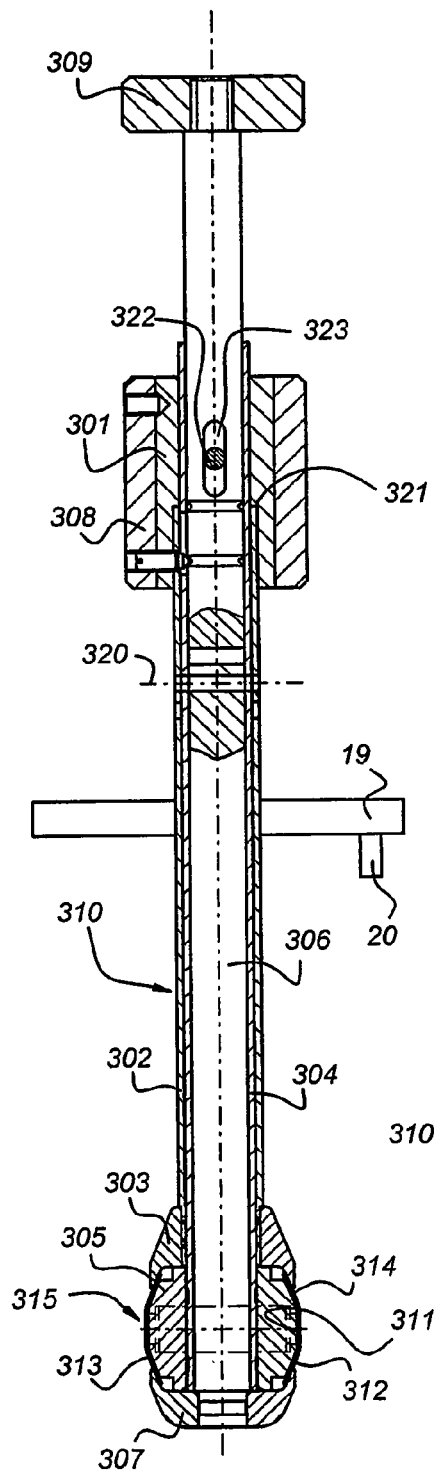
Figure 8:
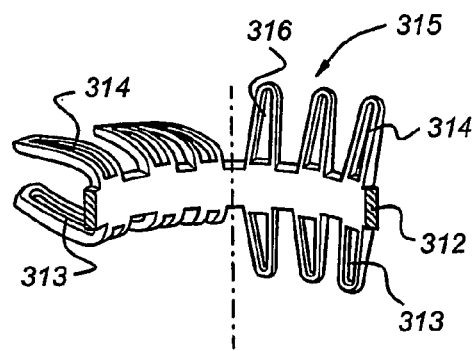
Figure 9:
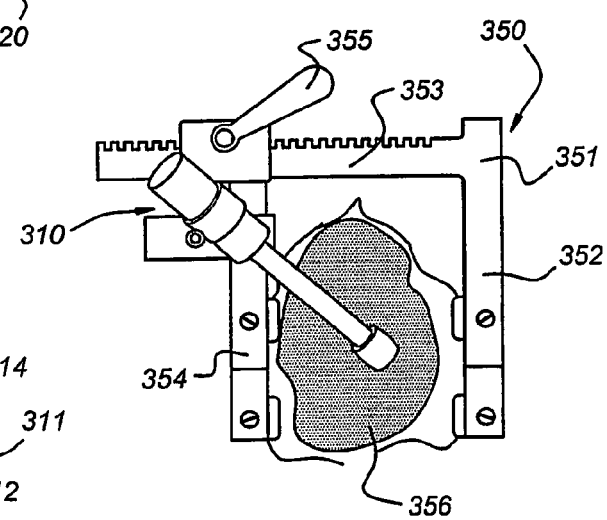
Figure 10:
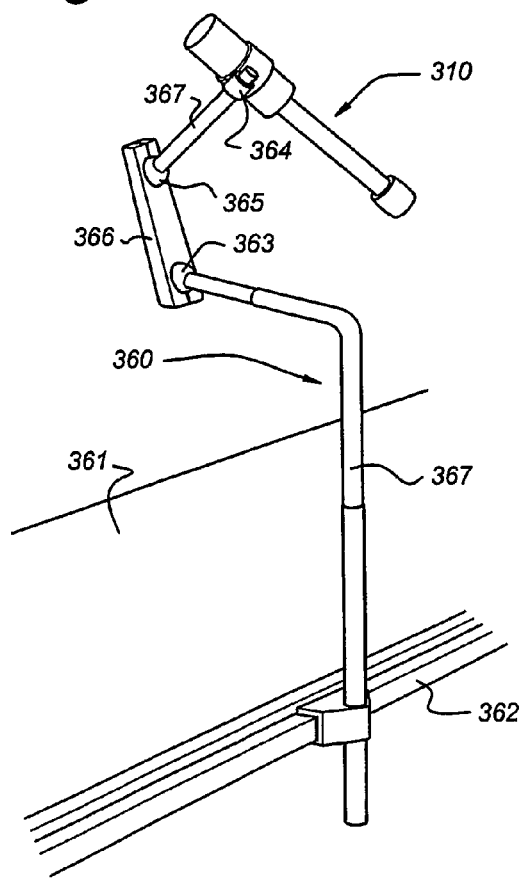
Figure 11:
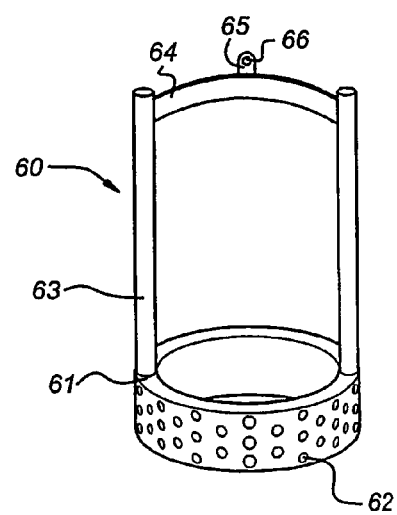
Figure 12:
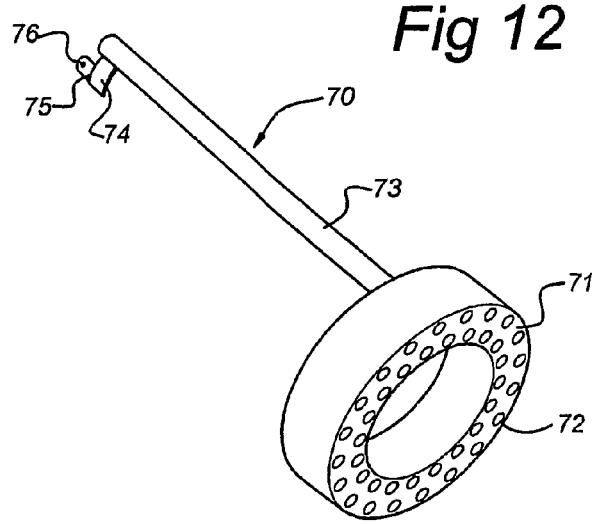
Figure 13:
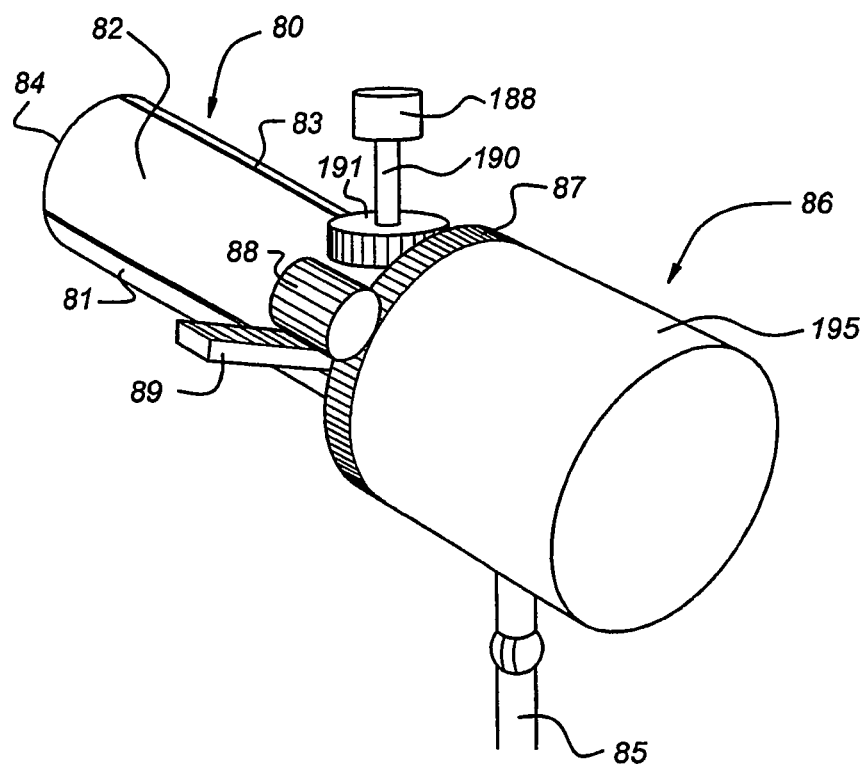
Figure 15:
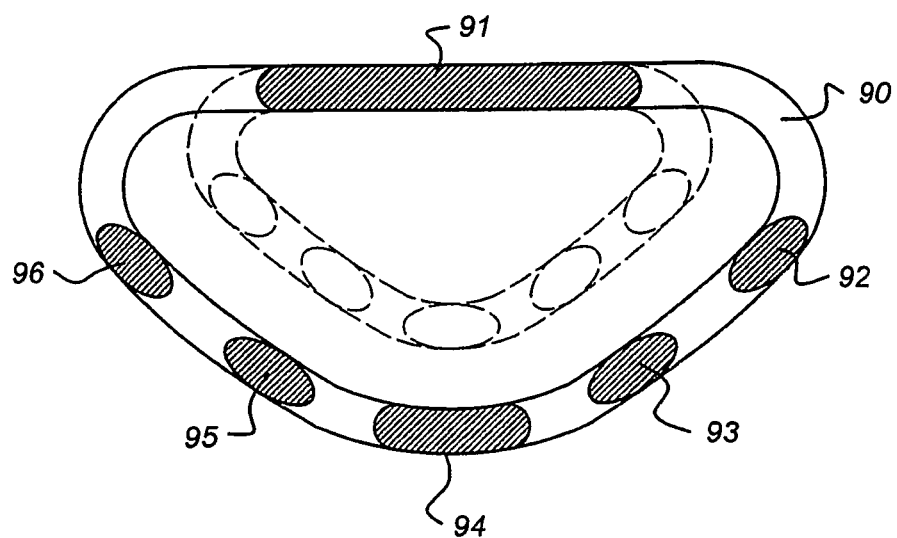
Figure 14A:
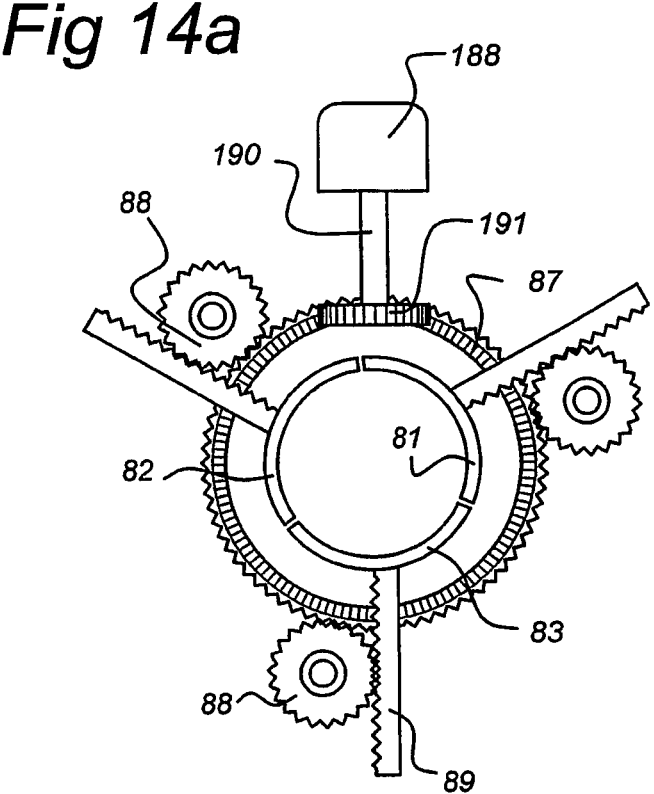
Figure 14B:
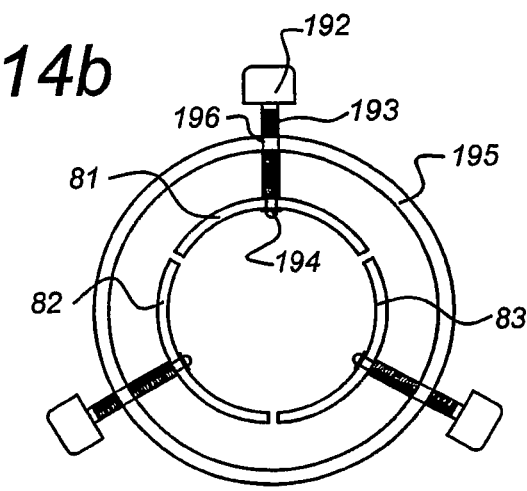
Figure 16:
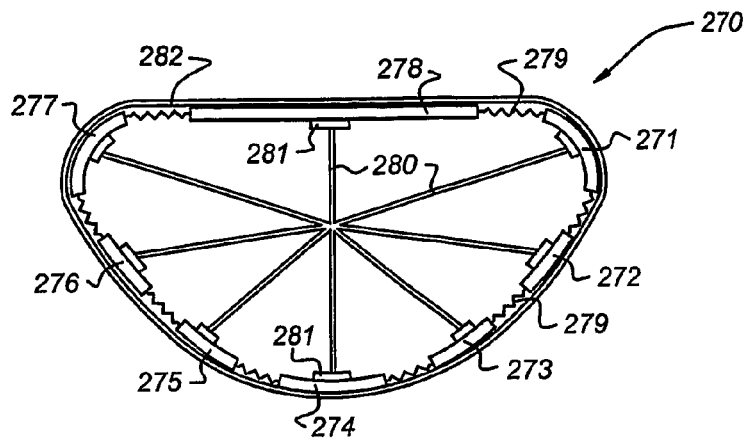
Figure 16A:
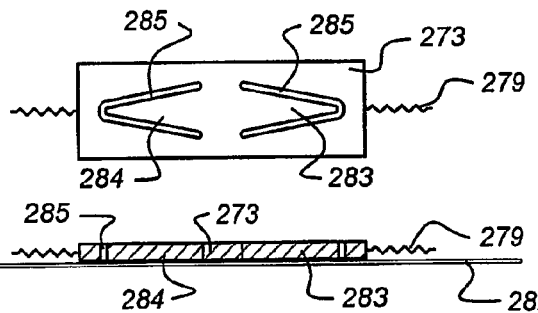
Figure 16B:
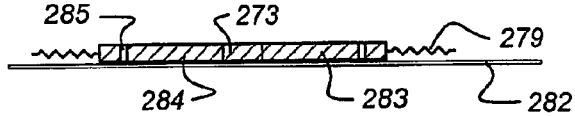
Figure 17:
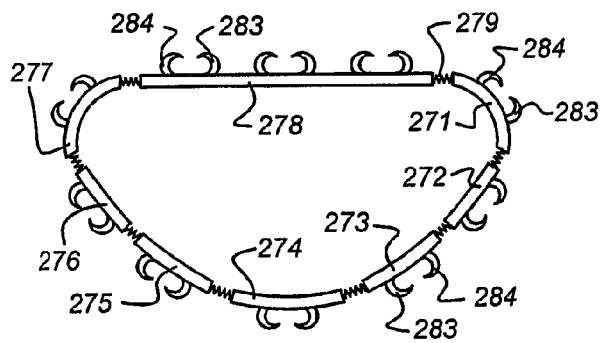
Figure 17A:
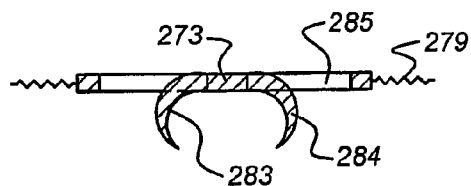
Figure 17B:
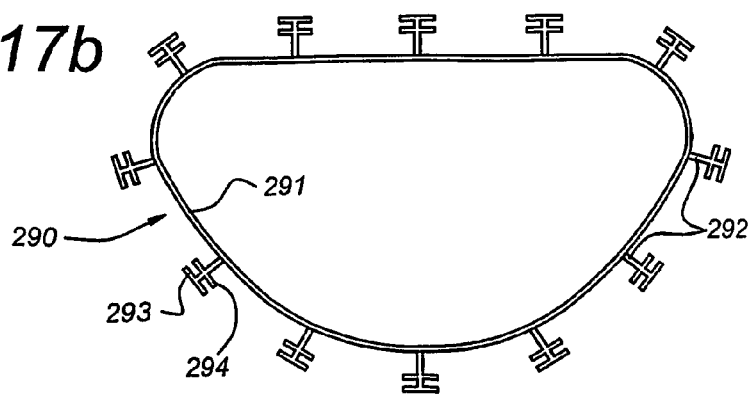
Figure 18:
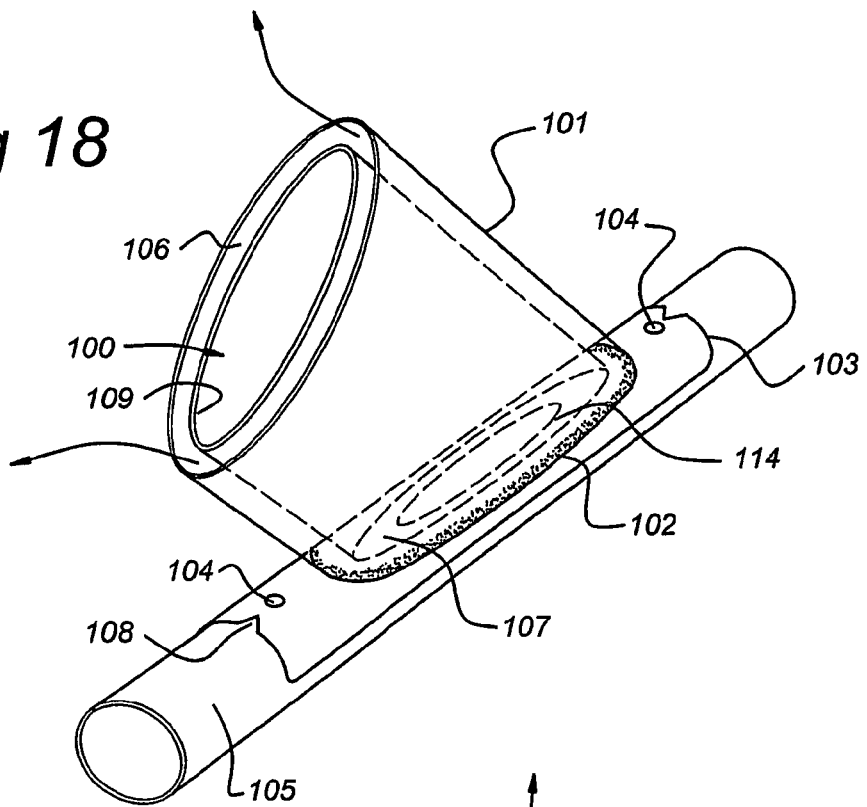
Figure 24:
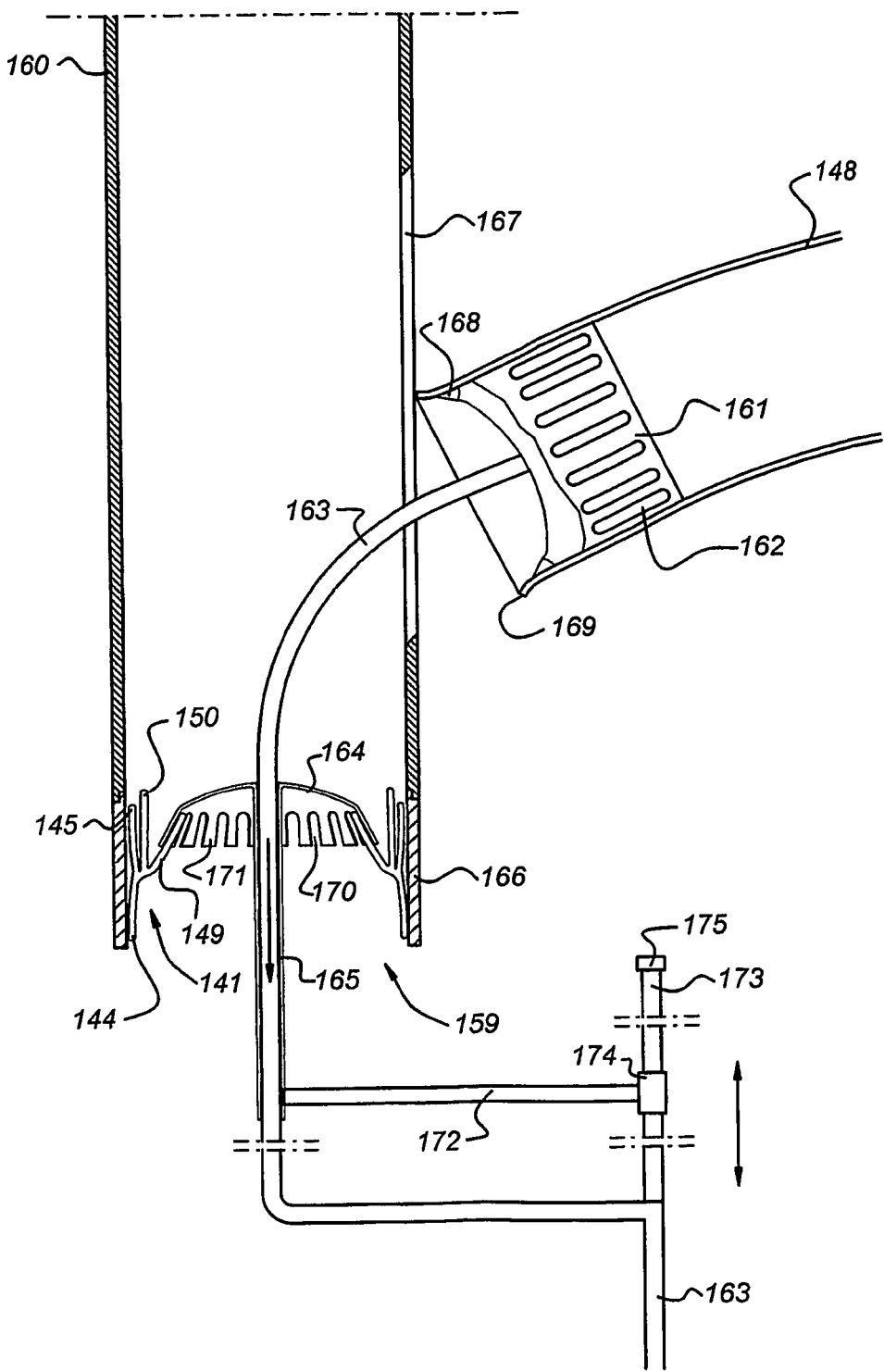
Figure 25:
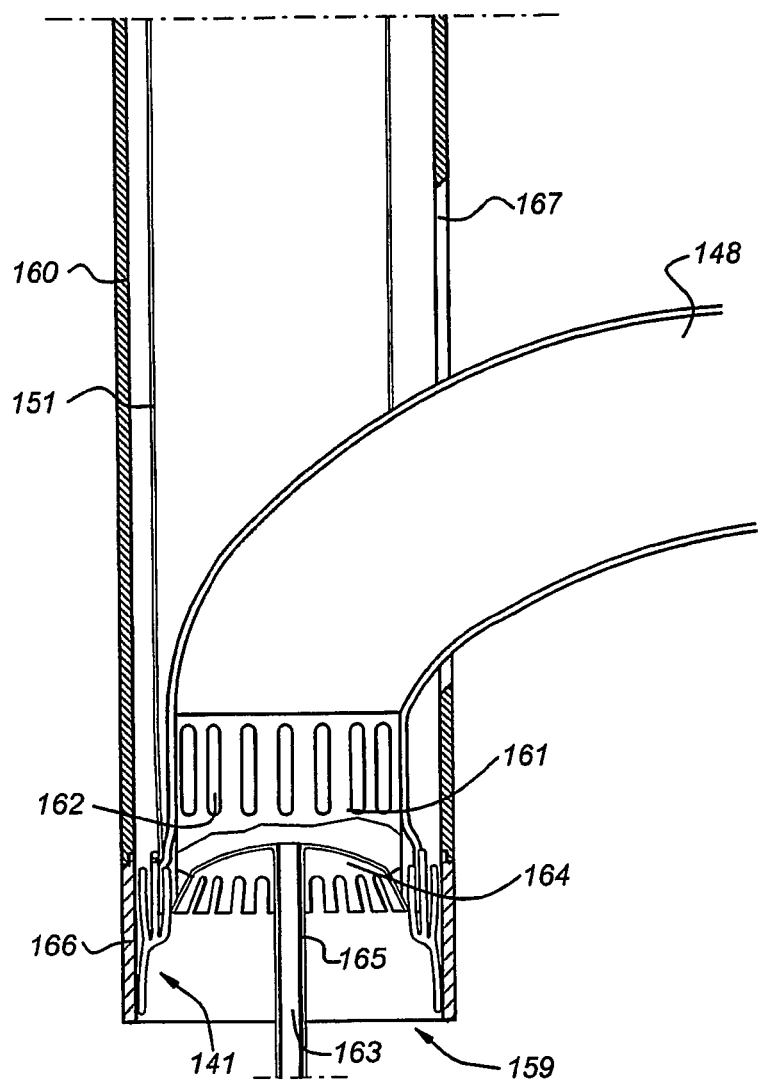
Figure 26:
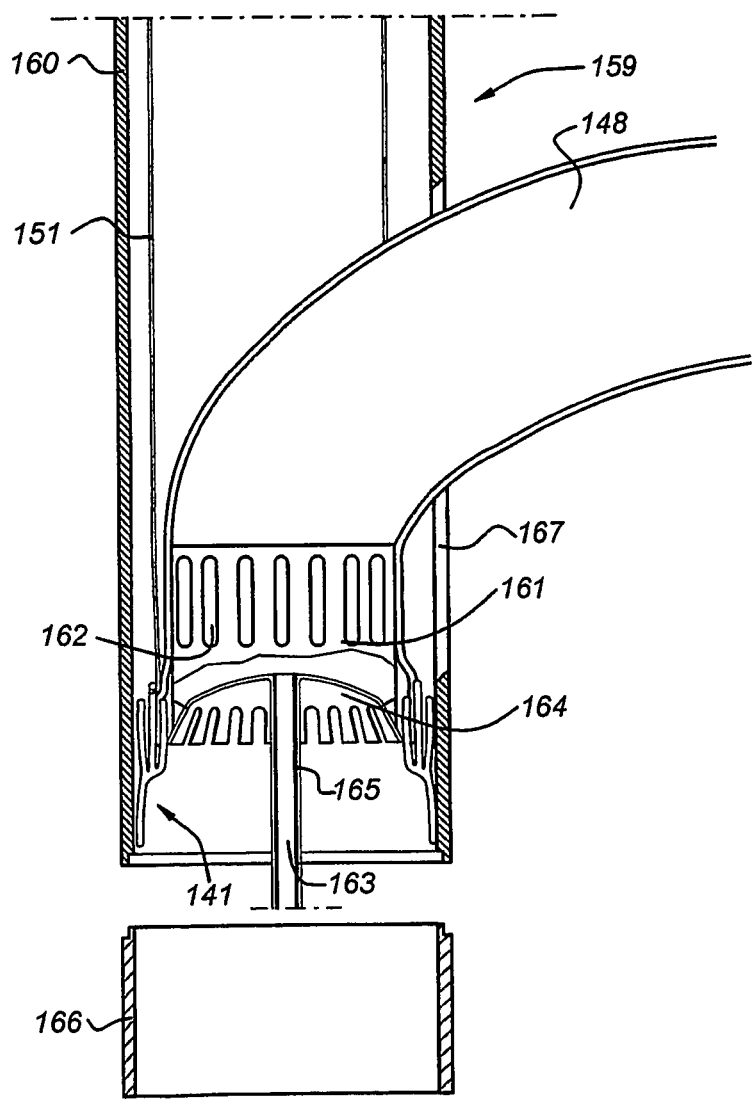
Figure 27:
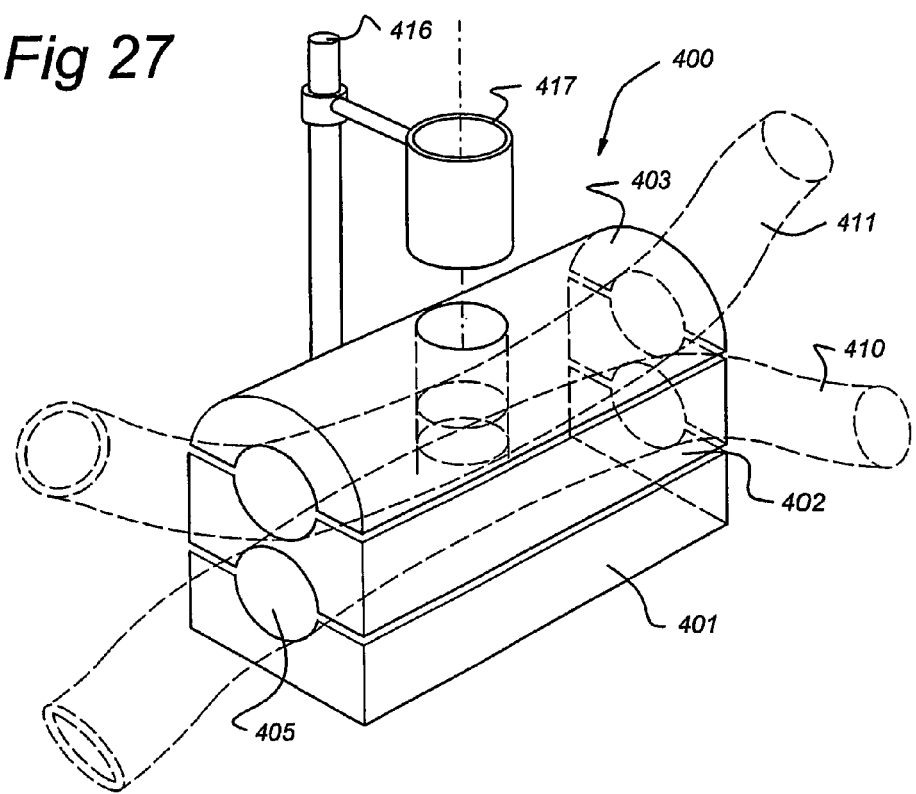
Figure 28:
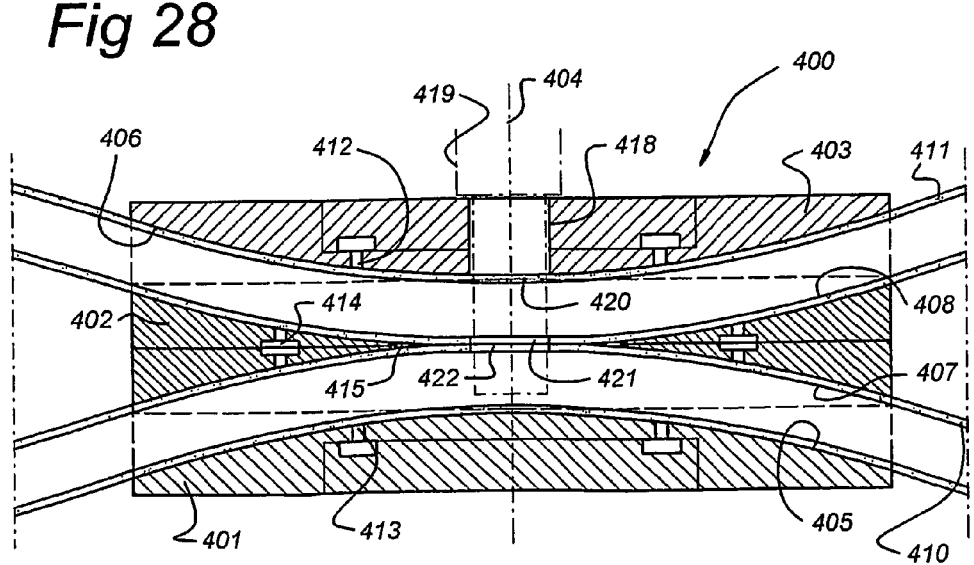
Figure 29:
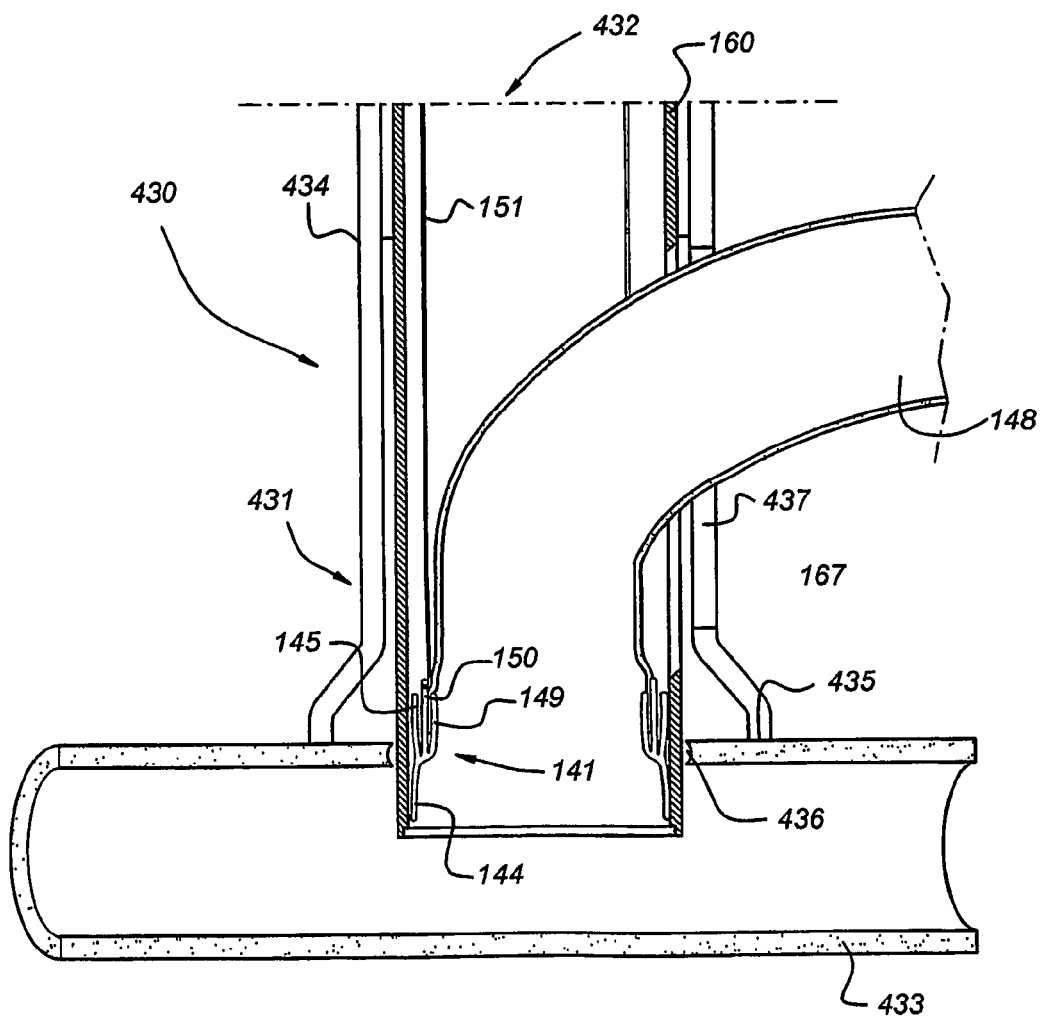
Figure 30:
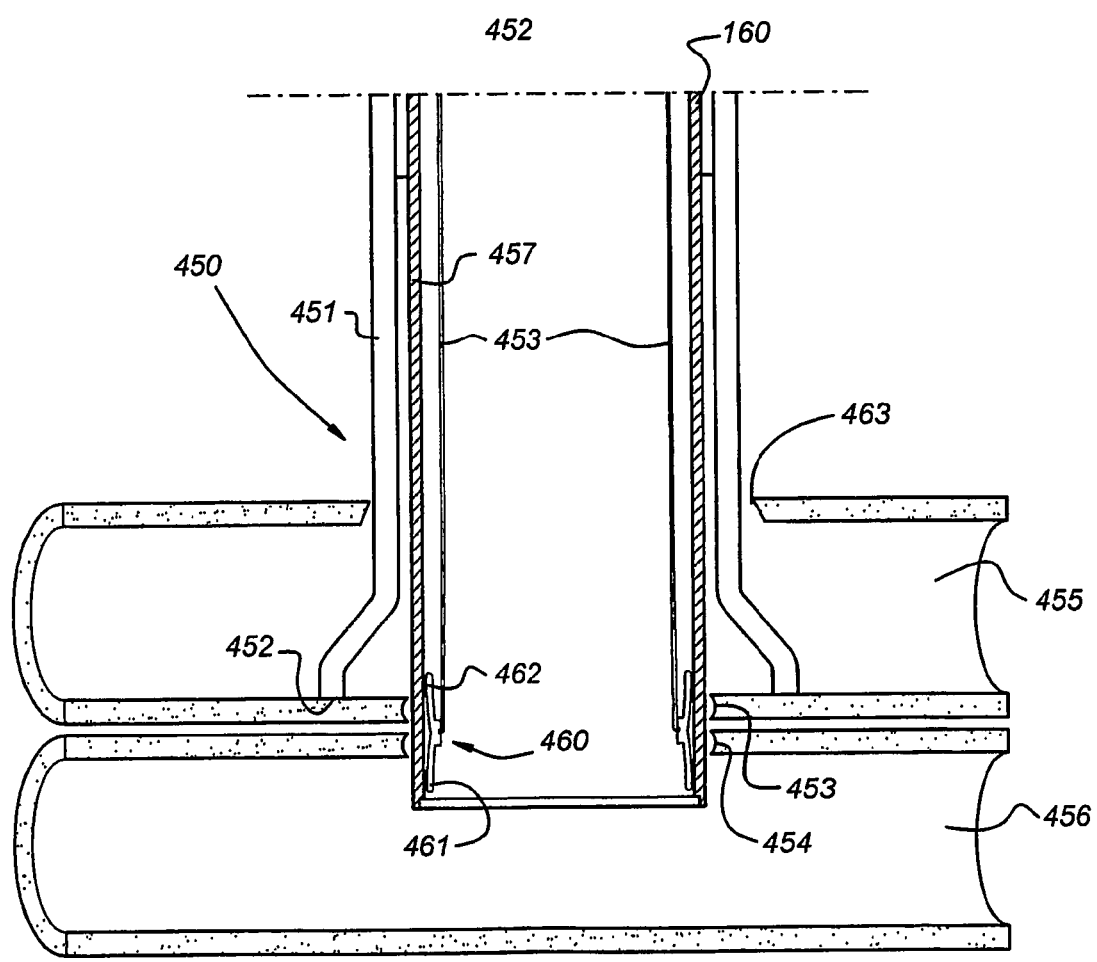
Figure 31:
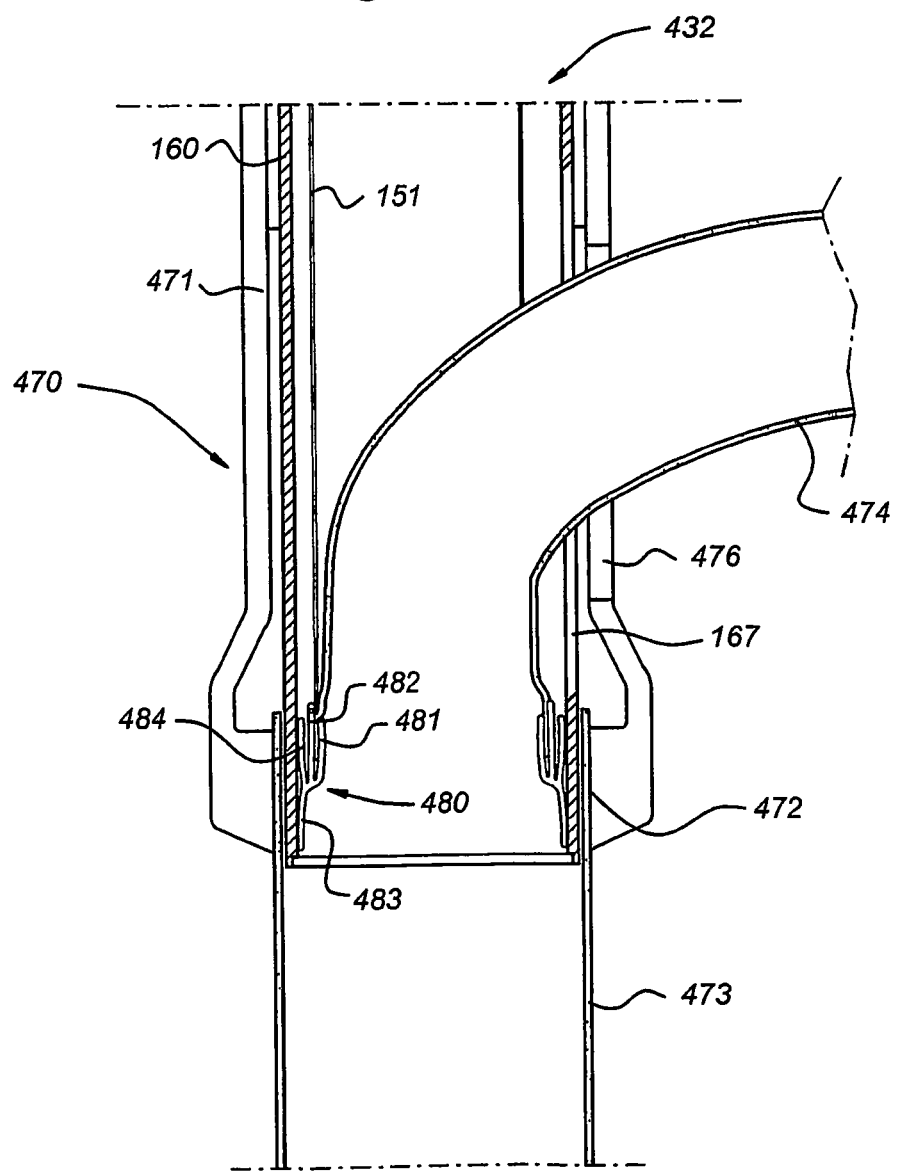
Figure 32:
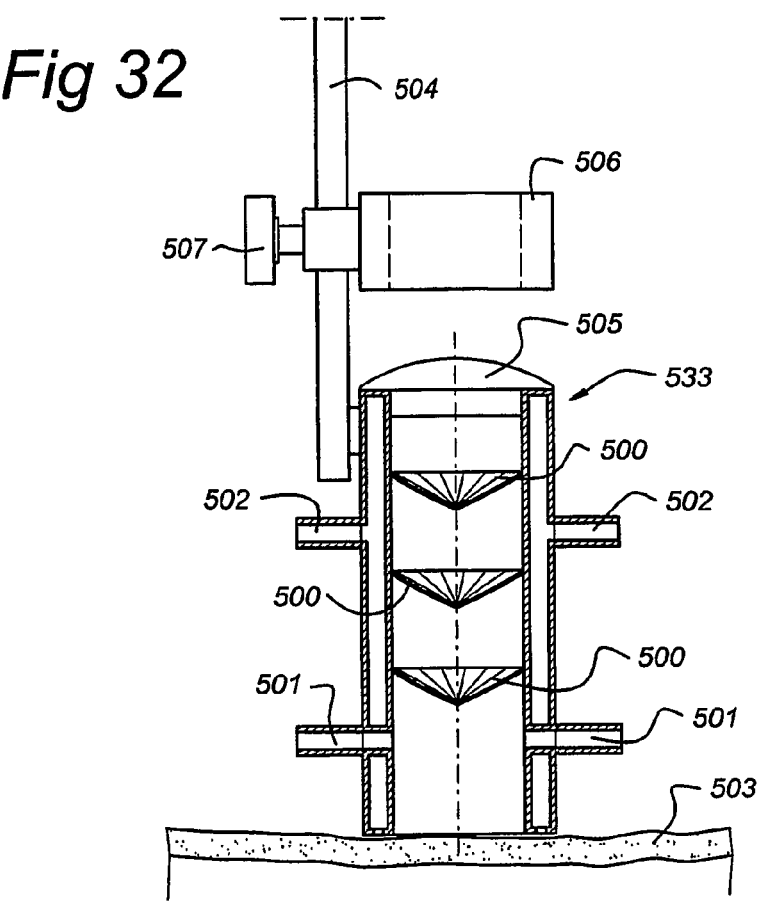
Figure 33:
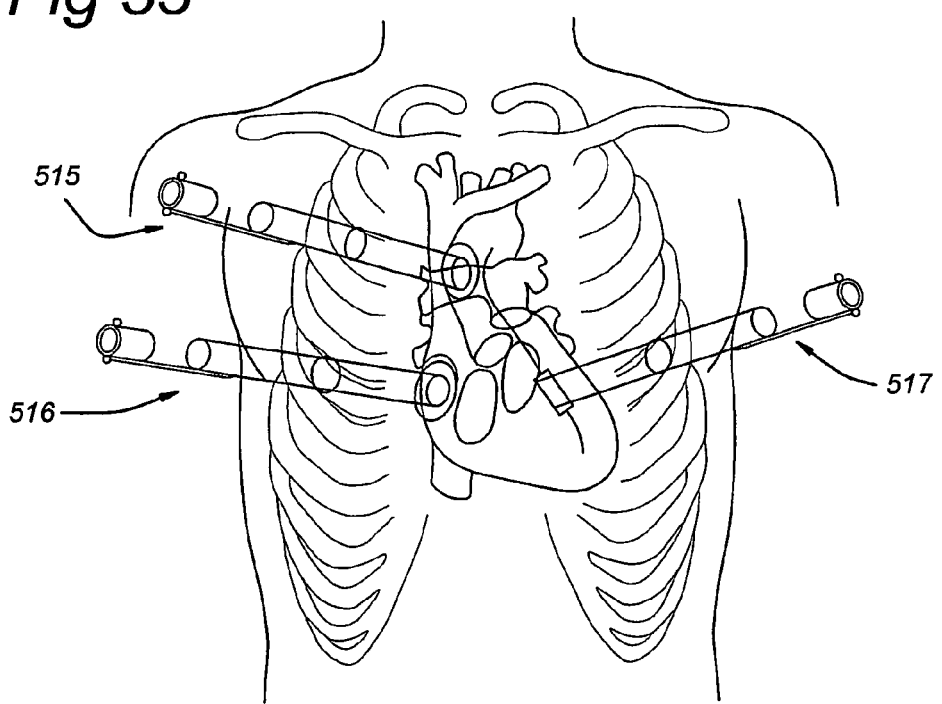
Figure 34:
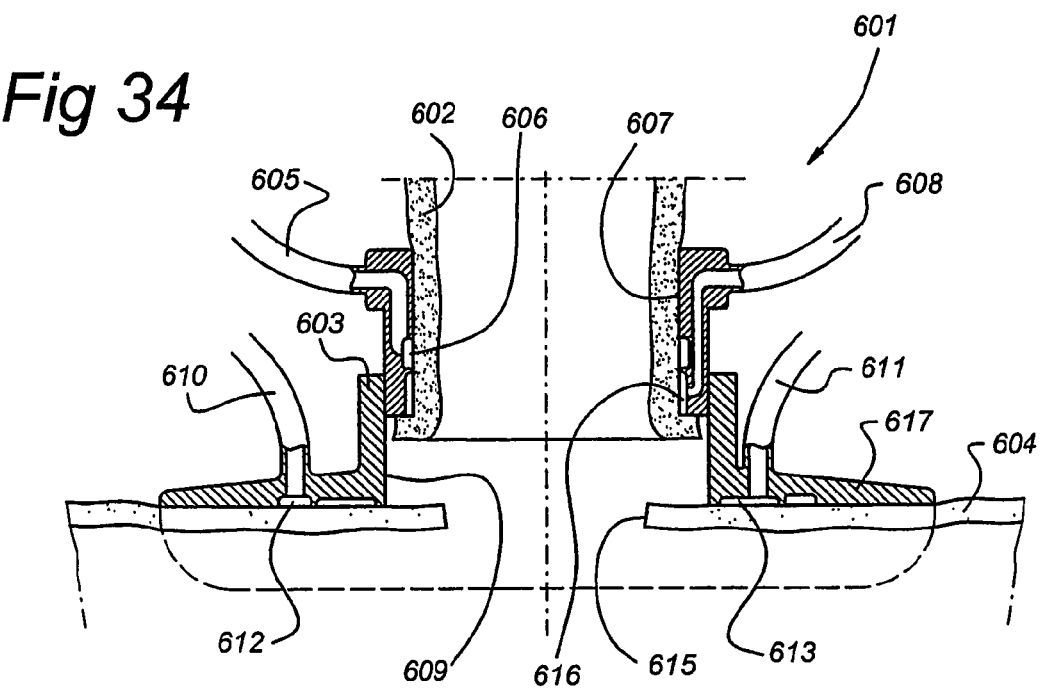
Figure 35:
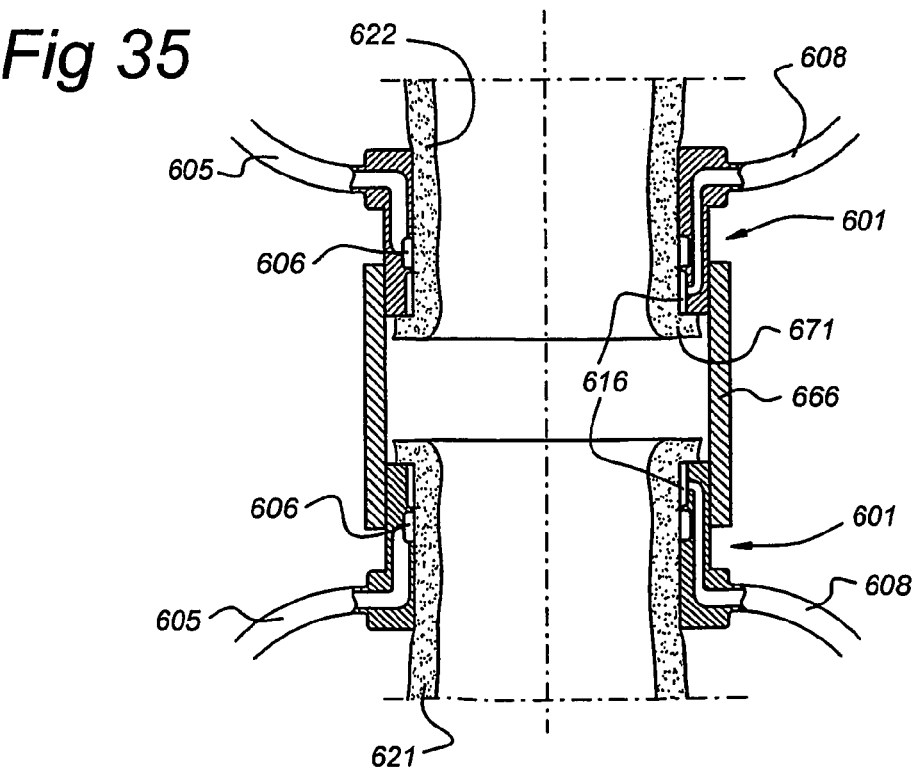
Figure 36:
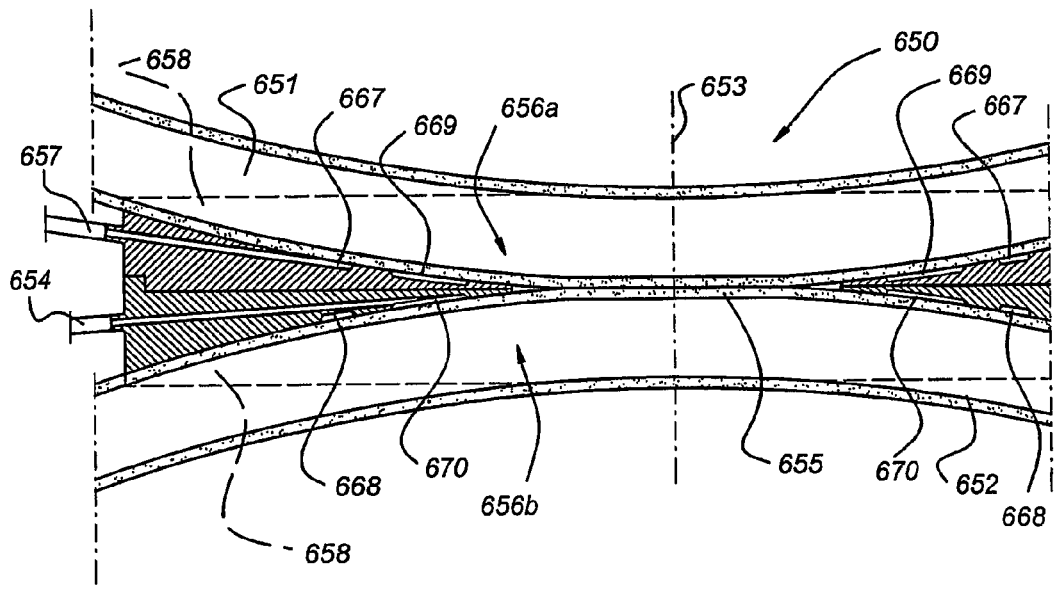

FIG. 6*a* shows the applicator according to FIGS. 1-5 in longitudinal section, the applicator being shown in the released position;

FIG. 6*b* shows the distal end of the applicator according to FIGS. 1-5 and 6 with an accessory for loading a fixing device on the applicator;

FIG. 7 shows a diagrammatic longitudinal sectional view of an applicator according to the third aspect of the invention intended for the assembly according to the first aspect of the invention, with a fixing device fitted under tension in the applicator, in a position suitable for positioning;

FIG. 8 shows, by way of illustration, an example of a fixing device that can be positioned using the assembly according to the invention;

FIG. 9 shows, highly diagrammatically, a first further embodiment of the assembly according to the first aspect of the invention;

FIG. 10 shows, diagrammatically, a second further embodiment of the assembly according to the first aspect of the invention;

FIG. 11 shows, highly diagrammatically, a first variant of a stabiliser for an assembly according to the invention;

FIG. 12 shows a second variant of a stabiliser for an assembly according to the invention;

FIG. 13 shows a third variant of a stabiliser for an assembly according to the invention;

FIG. 14*a* shows, highly diagrammatically, a possible operating mechanism for the stabiliser according to FIG. 13;

FIG. 14b shows, highly diagrammatically, a possible variant of an operating mechanism for the stabiliser according to FIG. 13;

FIG. 15 shows, highly diagrammatically, the mode of operation which can be achieved with a stabiliser according to the third variant, similar to that shown in FIGS. 13 and 14;

FIG. 16 shows, highly diagrammatically in plan view, a mitral valve ring according to the invention in the state ready for fitting;

FIG. 16a shows a detailed view of a fixing element on the mitral valve ring according to FIG. 16 and in the state in FIG. 16;

FIG. 16b shows a longitudinal sectional view of FIG. 16a;

FIG. 17 shows a diagrammatic view corresponding to FIG. 16, but now in the fitted state (omitting surrounding tissue);

FIG. 17a shows a sectional view corresponding to that in FIG. 16b, but now in the fitted state (omitting tissue);

FIG. 17b shows a highly diagrammatic plan view of a valve ring according to a further embodiment of the invention;

FIG. 18 shows a fourth variant of a stabiliser for an assembly according to the invention for use with an "end-to-side" anastomosis;

FIGS. 19 to 23 show, in diagrammatic longitudinal sectional view, partial view, an example of a procedure for producing an end-to-end anastomosis;

FIGS. 24 to 26 show, in diagrammatic longitudinal sectional view, partial view, an accessory for fixing a fixing device to a blood vessel in a number of intermediate steps;

FIG. 27 shows a diagrammatic, perspective view of a stabiliser for use when producing a side-to-side anastomosis;

FIG. 28 shows a longitudinal sectional view of that shown in FIG. 27;

FIG. 29 shows a diagrammatic longitudinal sectional view of an assembly according to the invention for producing an end-to-side anastomosis;

FIG. 30 shows a diagrammatic, longitudinal sectional view of an assembly according to the invention for producing a side-to-side anastomosis;

FIG. 31 shows a diagrammatic, longitudinal sectional view of an assembly according to the invention for producing an end-to-end anastomosis;

FIG. 32 shows a fifth variant of a stabiliser for an assembly according to the invention;

FIG. 33 shows a highly diagrammatic view of a trunk of the human body with examples of working duct connections;

FIG. 34 shows a highly diagrammatic sectional view with separated parts of an end-to-side anastomosis according to the invention;

FIG. 35 shows a highly diagrammatic sectional view with separated parts of an end-to-end anastomosis according to the invention;

FIG. 36 shows a highly diagrammatic sectional view of a side-to-side anastomosis according to the invention;

FIGS. 1-6 show an assembly according to the invention comprising a stabiliser 1 (see in particular FIGS. 1 and 2) and an instrument in the form of an applicator 2 (see in particular FIGS. 1, 3, 4, 5 and 6).

Figure 1:
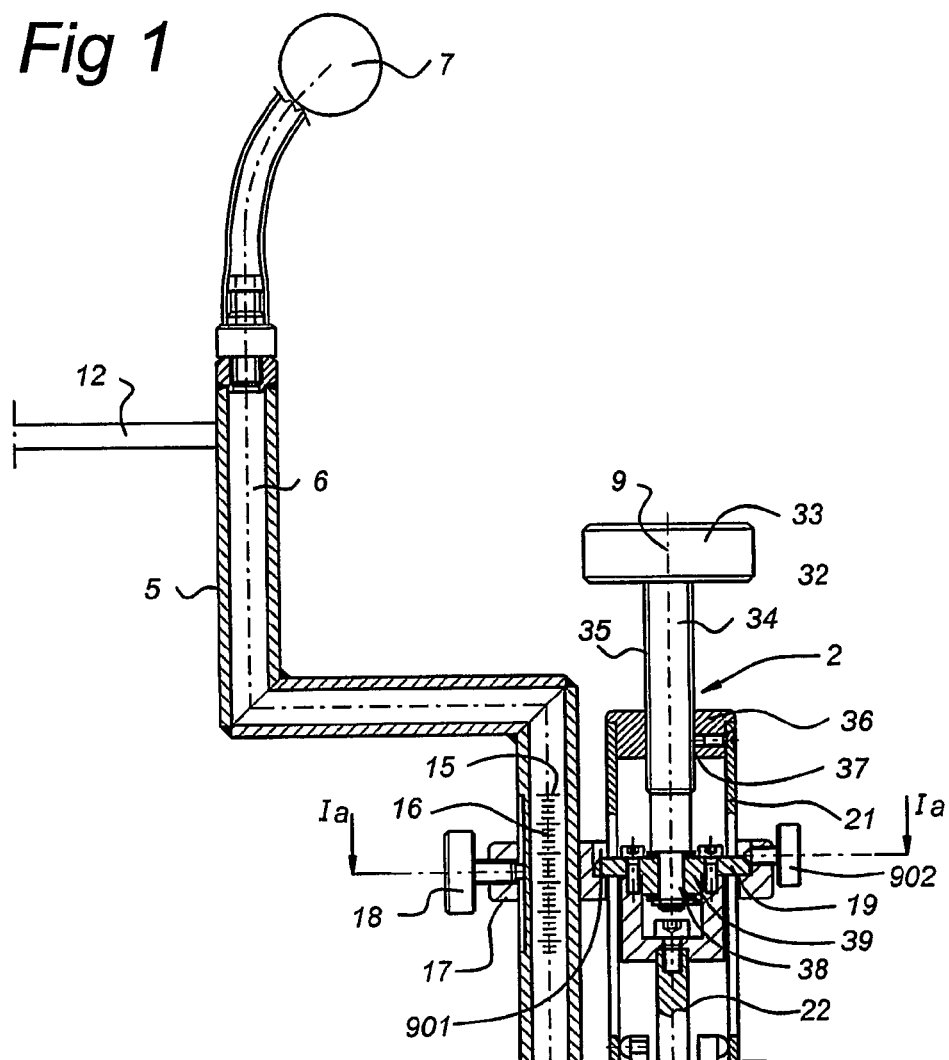

With reference to, in particular, FIGS. 1 and 2, the stabiliser 1 is made up of a working duct 3 in the form of a tube with a hollow suction rod 5 connected thereto, the interior 6 of which hollow suction rod 5 is connected or at least can be connected to a vacuum source, indicated diagrammatically by 7. Here the working duct 3 and the suction rod 5 are shown as a single rigid unit. However, the working duct 3 and the suction rod 5 can also be of flexible or rotary construction, for example by means of joints that can be locked. In this way, viewed in the longitudinal direction, the shape of both can be adapted as circumstances demand. If it is not so important that the user is able to adapt the shape him- or herself but a shape adapted to the circumstances is important, it is then also possible to provide the working duct and the suction rod with a predetermined curved or angled shape instead of the straight shape shown in the figures. The interior 6 of the suction rod 5 opens into a suction passage 4 formed in the interior of the wall of the working duct 3, which suction passage 4, in turn, is in communication with the suction nozzle 8. In this case the suction nozzle 8 opens in the radially outward direction. In this case the suction nozzle 8 is in one piece and extends over the entire periphery of the working duct 3 and, in the axial direction of the working duct 3 determined by the longitudinal axis 9, has a height that can vary from 1 mm to a few mm, for example can be 17 mm high.

The stabiliser and applicator shown in FIGS. 1-6 are intended in particular for positioning a fixing device for an aortic valve. In FIGS. 1 and 2 the natural aortic valve is at the level of the axis 10 and the surrounding vessel wall tissue 11 is shown there.

As is illustrated in FIG. 2, the stabiliser is introduced into the aorta to near, in particular close to, such as 5-15 mm away from, the location 10 of the natural aortic valve whilst vacuum has not yet been applied to the suction nozzle 8. Once the stabiliser has arrived sufficiently close to location 10, vacuum is applied to suction nozzle 8 so as then to suck tightly the vessel wall tissue 11 located around the suction nozzle 8. A sealing ring 900 is also provided at the distal bottom end of the working duct 3 to provide a good seal with the wall of the vessel tissue at that location. As a result of this suction hold it becomes possible to stabilise, and in particular to hold still, the location of the operation. All that needs to be done for this is to fix the stabiliser 1 to a solid construction. This is possible, for example, by fixing the suction line 5 to a stand 12. This stand 12 can then, in turn, be fixed to, for example, the operating table, the ceiling, the wall or the floor of the operating theatre or to some other solid construction. One possibility is to fix this stand 12 to a wound spreader, such as a sternum spreader, which is illustrated in FIG. 9 to be discussed below. Fixing to the operating table is illustrated on the basis of FIG. 10, which is to be discussed in more detail.

Figure 1A:
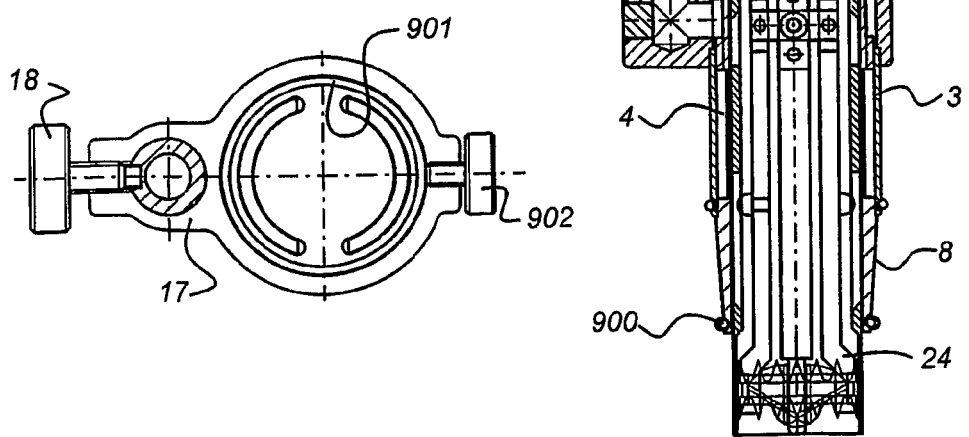

A scale 16 with a zero point 15 is provided on the suction rod 5. Furthermore, see FIGS. 1 and 1a, an instrument stop 17 that can be moved along the suction rod 5 is provided on the suction rod 5, which instrument stop 17 can be locked to the suction rod 5 by means of a rotary knob 18. Thus, here the suction rod 5 functions as a guide for the instrument stop 17. The scale 16 has a zero point 15. By now setting the instrument stop 17 along the scale depending on the measured distance between the distal bottom edge 13 (FIG. 2) and the location 10 for the fixing device it becomes possible to ensure, with high accuracy, that when the applicator 2, to be discussed below, is inserted in the working duct 3 the distal end of the applicator 2, which end carries the fixing device, reaches precisely the level of the location 10. For this purpose the applicator is provided with a stabiliser stop 19, to be discussed below, which comes into contact with the instrument stop 17 and thus can establish the mutual positions of applicator and stabiliser. As will be clear, with this arrangement it is practical if the zero point 15 is so chosen that when the instrument stop 17 is aligned with zero point 15 the fixing device 15 is precisely at the level of the distal bottom edge 13.

The assembly of instrument stop 17 and stabiliser stop 19 shown in FIG. 1 consists of a round, disc-shaped stop 19 that can be accommodated in a cylindrical accommodating cavity 901 which is provided in the instrument stop 17. In this way it is possible first to position the applicator and stabiliser with respect to one another in the longitudinal direction (i.e. in the longitudinal direction of the axis 9) and then to set the mutual angular position of the applicator and stabiliser (i.e. rotation of the one with respect to the other about axis 9). By means of the securing screw 902 it is possible with this arrangement first to fix the mutual longitudinal positioning and then, by further tightening the securing screw 902, the mutual angular positioning. Both fixed positions are thus achieved by operation of a single securing screw 902.

It is pointed out that the assembly of instrument stop 17 and stabiliser stop 19 in FIGS. 2, 3, 4, 5, 6 and 7 is shown and constructed differently to that in FIG. 1. The difference is that in accordance with FIGS. 2, 3, 4, 5, 6 and 7 there is no provision for setting the mutual angular position by means of securing screw 902. In these last-mentioned figures there is always a securing pin 20 and securing pin opening 903 which mutually positions both stops 17, 19 in an angular position and, if suitably constructed, for example as a screw, also determines the mutual longitudinal position. By providing several securing pin openings in one or both stops some provision for setting the mutual angular position is also possible. However, it should be clear that the stop assembly in the embodiment according to FIG. 1 can also be used in the embodiments according to FIGS. 2, 3, 4, 5, 6 and 7 or vice versa.

After the stabiliser 1 has sucked tightly to the vessel wall tissue 11, the distance between the distal bottom edge 13 (FIG. 2) of the working duct 3 and the location 10 where the fixing device has to be fixed can be measured with the aid of a suitable measuring instrument. Such a suitable measuring instrument can be, for example, an endoscope 14, as is shown in FIG. 2. This measuring instrument can, for example, consist of an opaque or transparent cylinder or part thereof having on the proximal side a stabiliser stop comparable to stabiliser stop 19 of applicator 2, and which measuring instrument is inserted in the working duct 3 by its distal end, and the position of the proximal end of which is established by the instrument stop 17 of the stabiliser. Transverse marks, for example a scale of marks 1 mm apart, can be made both on the distal side and on the proximal side of this measuring cylinder. By now measuring the distance between the distal bottom edge 13 of the working duct 3 and the desired location 10 using this measuring cylinder, for example under visual control with the aid of an endoscope, the instrument stop 17 on the suction rod 5 can be set correspondingly offset with respect to the zero point. By providing one or more longitudinal marks on the measuring cylinder it is possible to determine the desired rotation of the applicator and thus of the fixing device with respect to the stabiliser. By fitting a rotary ring on top of the instrument stop and bringing this into agreement with at least one vertical mark on the measuring instrument, the desired rotation of the applicator and thus of the fixing device can be determined. The measuring instrument can also be completely or partially integrated in or with the wall of the stabiliser, sections of a cylindrical shape or other shapes of the measuring instrument also being possible. It is also possible to determine the rotational position of the stabiliser with respect to the surrounding tissue in some other way in order to be able to determine the angle of rotation of the applicator with respect to the stabiliser. Furthermore, for example for use when fitting an aortic valve prosthesis, the bottom edge of the stabiliser and/or the measuring instrument and/or the applicator can be made sinusoidal.

In order to bring the stabiliser and/or applicator more easily to its destination, it can be advantageous to provide the distal end of the stabiliser and/or applicator with tapering narrowing in the distal direction. This makes it easier to pass by tissue.

By providing the distal end of the stabiliser and/or applicator, in particular of the working duct 3 and/or sleeve 21, respectively, with axial incisions, it becomes possible, if the working duct wall and/or sleeve wall, respectively, has adequate flexibility, to widen or narrow the distal ends somewhat should this be practical.

The applicator 2 will now be discussed below. The applicator 2 consists of an obstructing sleeve 21 which is provided at its proximal end with a stabiliser stop 19, which is provided with a securing pin 20. When this stabiliser stop 19 is in contact with the instrument stop 17 of the stabiliser, the securing pin 20 of the stabiliser stop 19 will drop into a corresponding recess made in the instrument stop 17 and thus prevent rotation of the sleeve 21 with respect to the working duct 3. If the working duct 3 and the sleeve 21 have a shape that differs from the circular shape, the securing pin 20 can optionally be omitted.

An elongated support member 22 in the form of a rod 22 is accommodated centrally in the sleeve 21. This rod bears, in turn, two, possibly three or four, gripper arms 23. Each gripper arm 23 is provided at the distal end with a gripper end 24. The gripper end 24 has a cut-out groove 25 in which the fixing device can be accommodated; see in particular FIG. 6.

The gripper arms 23 are fixed to the rod 22 via pivot points 26 such that they can swing. The support arms 23 are also provided with a distal projection 27 and proximal projection 28.

Partly also with reference to FIG. 8, the fixing device 315 consists of a tubular member 312 with distal flange fingers 313 and proximal flange fingers 314 thereon. In the position shown in FIGS. 1 and 3, these flange fingers 313 and 314 have been brought into a straightened position, overcoming resilience, and are held in said straightened position by the sleeve 21. By now moving the sleeve 21 in the proximal direction with respect to the rod 22, the sleeve 21 is brought into the release position shown in FIG. 4. During this movement the distal flange fingers 313 and proximal flange fingers 314 flip under the influence of the resilience into a position pointing radially outwards so as to anchor themselves in the surrounding vessel wall tissue. The gripper arms 23 remain unchangeably in their gripping position while the sleeve 21 is moved from the obstructing position in FIG. 3 into the release position in FIG. 4. The reason for this is that in the obstructing position the distal projections 27 protrude into slots 30 that have been made in the sleeve 21 and because these slots 30 have a length such that the projections 27 still protrude into said slots 30 when the tube 21 is in the release position shown in FIG. 4. By now moving the tube 21 further upwards in the distal direction with respect to the rod 22, the distal projections 27 will leave slot 30 at the distal end thereof. As a consequence of this the arms 23 are driven radially inwards on the distal side of the pivot point 26 so that the gripper ends 24 move into the release position shown in FIG. 5. In order to facilitate movement of the gripper ends 24 towards one another, the proximal projections 28 are at that point in time located in slots 31 that have been made in the wall of the sleeve 21. In the stage preceding the release position in FIG. 5, that is to say the stages according to FIGS. 3 and 4, the projections 28 ensure that the gripper arms 23 remain locked in their gripping position since the projections 28 push the gripper ends 24 radially outwards.

After the release position shown in FIG. 5 has been reached, the applicator 2 can be brought into a completely detached position by moving the applicator 2 in the proximal direction away from the fixing device 315, which in the meantime has been positioned and anchored, as is shown in FIG. 6(a). The movement of the sleeve 21 with respect to the rod 22 can easily be achieved by means of the operating mechanism 32 that is clearly visible in, in particular, FIG. 1.

This operating mechanism 32 consists of a rotary knob 33 to which a pin 34 provided with screw thread 35 is fixed. The screw thread 35 extends into an opening 37 provided with matching internal screw thread. This opening 37 has been made in a proximal plug 36 which is fitted in the proximal end of the sleeve 21. The distal end 38 of the pin 34 is accommodated such that it can freely rotate (without screw thread) in a unit 39 fixed to the rod 22. This unit 39 is, in turn, joined to the stabiliser stop 19 to prevent rotation. By now turning the rotary knob 33, the sleeve, the obstructing sleeve 21, is pulled upwards in the proximal direction with respect to the rod 22. In this way the positions according to FIGS. 4 and 5 can be reached successively from the obstructing position shown in FIG. 3.

FIG. 6b shows that use can be made of a sleeve 317 for loading a fixing device 315, with a valve prosthesis optionally already fitted therein in advance, on an applicator. This sleeve is comparable to the sleeve 166 shown in FIGS. 24-26. The fixing device 315 is positioned or supplied with the flange fingers 313, 314 straightened, against a resilient force, in the sleeve 317. The gripper ends 25 of an applicator that is in the position according to FIG. 6a are then inserted in the fixing device, after which the actions described with reference to FIGS. 3-5 are carried out in the reverse order. The gripper ends 25 will then pull the fixing device gripped by these from the sleeve 317 into the tube 21.

It is pointed out that the applicator as shown in FIGS. 1 to 6 can optionally also be used entirely independently of the stabiliser 1; this is in accordance with the second aspect of the invention.

As will be clear, it will be possible to construct the gripper arms 24 from FIGS. 1 to 6 in a wide variety of different ways. For example, it will be possible to adapt the shape and construction of the gripper sections 25 in particular to the valve prosthesis to be fitted. The gripper sections 25 can, for example, have a concave shape so as to be able to engage on the inside of a correspondingly curved tubular member of a fixing device. In the case of a valve prosthesis with a natural valve the gripper arms will preferably engage between the valve leaflets, or at the level of the so-called commissura. This essentially also applies for a synthetic valve which imitates the natural valve leaflets as far as possible. In the case of biological valves it is important, in particular, that the gripper arms are so constructed that they are not able to damage the biological valve leaflets when they snap fully inwards and the applicator is pulled out upwards. In the case of biological valves it is also readily conceivable, and in connection with it not being possible to damage the valve leaflets, also very useful if the gripper arms of the applicator engage on the tubular member along the outside of the so-called raised part of the biological valve. This is because the so-called raised part of the biological valve forms a sort of tube-like whole within which the natural valve leaflets are located. With diverse types of valve prosthesis it is also conceivable that raised lobes are fixed to the valve prostheses and/or the tubular member of the valve fixing device in the proximal direction, which lobes have holes or cut-outs therein in which pins or projections fixed to the gripper arms can engage. Incidentally, the holes or cut-outs do not necessarily have to be provided in raised lobes but can optionally be provided directly in the tubular member of the prosthesis and/or the tubular member of the valve fixing device, which first mentioned tubular member is ultimately accommodated in the fixing device according to the invention. It should be clear that the shape of the gripper arms also has to be adapted when fitting a valve ring prosthesis or vessel anastomosis fixing device. In the case of vessel anastomosis fixing devices the gripper arms can, for example, engage on the inside of the tubular member of the fixing device, but can also engage on fixed raised parts or lobes, which may or may not be extended, of the tubular part of the fixing device, it optionally being possible for openings for these gripper arms to have been made. Here the gripper arms can engage from the inside, but also from the outside. Direct clamping mechanisms or threaded connections are, for example, also possible.

FIG. 7 shows an applicator 310 that except for a stabiliser stop 19 and securing pin 20 is identical to the applicator from FIG. 1 of NL Patent 1018302 in the name of the Applicant, which was published on 17 Jul. 2001. Except for the stabiliser stop 19 and securing pin 20, the reference numerals in FIG. 7 have been taken from FIG. 1 of NL 1018302 after increasing by 300. Reference is made to NL 1018302, in particular FIGS. 1 and 2 and associated text, for a complete description of this applicator. As will be clear, the applicator 10 from FIGS. 1 and 2 of NL 1018302 can readily be used in the assembly according to the present invention. This applies more generally for all applicators according to Claims 1-16 of NL patent 1018302 and thus also including that which is shown in FIG. 3 of NL patent 1018302. For this applicator from FIG. 3 of NL 1018302 as well, just as for that from FIG. 7 of the present application (corresponding to FIG. 1 of NL 1018302) only a stabiliser stop 19 has to be added. With reference to FIG. 7 of the present application and what has been described in NL 1018302, it will be clear that it is preferable to fix the stabiliser stop 19 such that it is immovable with respect to the support tube 304, such that the release tube 302 surrounding it is able to move with respect to the support tube and stabiliser stop 19. This is easy to achieve, for example by providing axial slots in the release tube 302 through which pins protrude which fix the stabiliser stop 19 to the support tube 304. NL patent 1018302 can then also be integrally incorporated in its entirety in the present application by reference.

With reference to FIG. 8, in which an example of a fixing device 315 of the type according to the invention is shown merely for illustration, the fixing device 315 is made up of a tubular member 312, which usually is of closed annular shape, but can also be interrupted at one or more locations, and has bottom flange fingers 313 and top flange fingers 314, which in the present application are referred to as, respectively, distal flange fingers 313 and proximal flange fingers 314. In the right-hand half of FIG. 8 the flange fingers 313, 314 are shown in the straightened position (cf. the view of the fixing device 315 in FIG. 7) and in the left-hand half of FIG. 8 they are shown in a position pointing radially outwards. The flange fingers 313, 314 can be open as is shown (see: openings 316) or can also be closed, pin-shaped or V-shaped (not shown), sharp or blunt, it being possible for top and bottom flange fingers to be positioned opposite one another as mirror images with respect to the horizontal sectional plane, but also alternately, in which case at the location where there is a flange finger peak on one side there is a flange finger trough on the other side. The last mentioned variant will have high covering capacity. The flange fingers can be constructed as a pin, which in the case of a vessel fixing device are able, after release of the flange fingers on bending back again towards the tubular member, to perforate the optionally extended tubular part of the fixing device through pre-made openings in the tubular part. Insofar as a fixing device 315 is used for fixing a valve prosthesis or valve ring prosthesis, the tubular member 312 can be provided with facilities that completely or partially contain the valve or valve ring, but also with cut-outs and/or protuberances which can fit in corresponding protuberances and/or cut-outs of such prostheses, and in particular the valve housing of a valve prosthesis, which is contained by the fixing device. A protuberance facing radially inwards on the tubular member 312 can, for example, consist of two horizontal and/or vertical slits that are cut out of the wall of the tubular member in one or more locations, for example two or three, the intermediate wall section being able to move radially inwards, after removal of an obstruction, so as to clamp, permanently or temporarily, in a corresponding cut-out in the valve housing. Another example is a ring that is placed around and within a cut-out in the valve housing and which, for example, is joined to the tubular member 312 by welding. Usually such fixing mechanisms will enable the valve prosthesis to be turned within the tubular member 312.

FIG. 9 shows highly diagrammatically, by way of example, an applicator 310 according to the invention, which is not shown in more detail, fixed on a sternum spreader 350 known per se. As has already been made clear, instead of the instrument such as an applicator it is also possible to mount a stabiliser according to the invention on a sternum spreader, or both one or more instruments can be mounted on a single sternum spreader as a stabiliser. The sternum spreader 350 shown by way of example consists of an L-shaped part 351 with a first spreader arm 352 and guide arm 353, on which a second spreader arm 354 has been fitted by means of an adjusting lever 355 such that it can be moved. With this spreader the spreader arms 352 and 354 serve to push apart the sternum, which has first been split for this purpose, in order to make the heart 356 accessible for an intervention. By fixing the applicator 310 to the sternum spreader, optionally with a stand with lockable arms and/or joints between them, the applicator is able to be stabilised and immobilised with respect to the location where the fixing device has to be fitted.

FIG. 10 shows highly diagrammatically, by way of example, an applicator 310 which is fixed to an operating table 361 by means of a stand 360. As has already been made clear, instead of the applicator it is also possible to mount another instrument or a stabiliser according to the invention on an operating table, or both an applicator and one or more instruments can be mounted on a single sternum spreader. The stand 360 can be moved along a guide rod 362 in the longitudinal direction of the operating table 361 and is also provided with a ball joint 363, a ball joint 365 and a linear joint 364 with the necessary arms 366 and 367 between them, which arms can optionally also be adjustable in the longitudinal direction. Although not drawn, it will be possible to lock the various joints and arms in position using locking means that a person skilled in the art can easily find in the prior art. The main support arm of the stand consists of an L-shaped bar 367, the two arms of which, as is indicated diagrammatically, are preferably telescopic. The stabiliser and/or instruments can also be held in a stable position by an operation robot which is on the floor of the operating theatre or is fixed to the walls or the ceiling of the operating theatre.

When using a stand, stand and stabiliser or the at least one instrument can form an integral whole or can be coupled, and preferably also uncoupled, by means of a coupling such as a snap-fit connector.

In order to facilitate movement of the stabiliser and the instrument according to the invention through curved ducts it can be highly advantageous according to the invention to make the stabiliser and the instrument, in particular the working duct and optionally the suction rod, the support tube, the release rod and release tube, curved or deformable.

FIG. 11 shows a first variant of a stabiliser 60 for use with the assembly according to the invention. The stabiliser 60 consists of a suction ring 61 with a multiplicity of suction nozzle openings 62, which face radially outwards, on the outer peripheral surface thereof. The suction ring 61 is mounted on two rods 63 (there can also be one rod just as there can also be more, such as 3 or 4), at least one of which is of hollow construction for connection to a vacuum source in order to be able to apply a vacuum to the suction nozzles 62. The suction ring 61 is fixed to the rods 63 at the distal end. At the proximal end thereof, the rods 63 are joined to one another by a semicircular element 64 that forms an instrument stop, which optionally can be provided with a lip 65 with a securing pin 66. The stop 64 here has the same role as the stop 19 of the applicator according to FIGS. 1-7. The stabiliser 60 can completely replace the stabiliser 1. All that is then lost is that there is no longer really a working duct.

FIG. 12 shows a second variant of a stabiliser 70. This stabiliser is provided with a suction ring 71 with axially oriented axial suction nozzles 72. The suction ring 71 is fixed to a hollow rod 73 which can be connected to a vacuum source. In a manner comparable to that which has been described for the stabiliser 60, the rod 73 is provided proximally with respect to the suction ring 72 with a support 74 for a stop 75. The stop 75 is optionally again provided with a securing pin 76. The stabiliser 70 is suitable in particular for use in the case of a mitral valve or tricuspid valve.

FIGS. 13 and 14 together show a third variant of a stabiliser for use with an assembly according to the invention. In these FIGS. 13 and 14*a* belong together and FIG. 14*b* shows a variant of the adjustment mechanism in FIG. 14*a*. The possibility of incorporation of the adjustment mechanism from FIG. 14*b* in FIG. 13 will be immediately apparent. The stabilisers in FIGS. 13 and 14 are made up of three cylinder segments 81, 82 and 83. These cylinder segments 81, 82 and 83 are provided at their distal ends 84 with suction nozzles, which are not indicated in more detail. Proximally with respect to the distal ends 84, the cylinder segments 81, 82 and 83 are fixed to a stand 85 via an adjustment mechanism 86. The suction tube 5 from FIG. 1 can optionally run through this stand 85, but this suction tube 5, which is not shown in FIG. 13, can also run independently of the stand 85.

With reference to FIGS. 13 and 14, the adjustment mechanism comprises, in highly diagrammatic form, a large toothed ring 87. The toothed ring 87 can be turned by means of an adjusting knob 188 via a pin 190 and a gear 191. The toothed ring 87 can be regarded as a sun wheel. Three toothed planetary wheels 88 are provided around it. Each planetary wheel 88 engages with a rack 89. The toothed ring 87 is mounted in a bearing on a cylindrical support housing 195 such that it can rotate, which support housing 195, in turn, is fixed to the stand 85. The racks 89 protrude through the cylindrical support housing 195 so as to support the respective cylinder segments 81, 82 and 83 on the inside thereof and on the outside of the support housing 195 to engage with the planetary wheel 88 and via this planetary wheel 88 to engage with the toothed ring 87. By now turning the large ring 87 by means of the rotary knob 188, the planetary wheels 88 also start to turn, which then bring the racks 89 into motion. Depending on the ratios of the gearing it is then possible to move the racks 89 over an identical radial distance each time or optionally to move them over different radial distances. In the latter case the toothing on the planetary wheels 88, in particular, will have different numbers of teeth. In the embodiment according to FIG. 14*a*, the cylinder segments 81, 82 and 83 will be adjusted simultaneously in accordance with a relationship predetermined by the gear ratios.

FIG. 14*b* shows a variant of the adjustment mechanism from FIG. 14*a*. In the case of the adjustment mechanism shown in FIG. 14b it is possible to adjust each cylinder segment 81, 82 and 83 independently of the other cylinder segments 81, 82, 83. Thus, for example, the cylinder segment 81 can be adjusted whilst the cylinder segments 82 and 83 are not adjusted. In the embodiment according to FIG. 14b this is made possible by fixing each cylinder segment to a pin 193 provided with screw thread, which pin supports the respective cylinder segment at 194 in a manner such that the pin 193 is able to rotate freely about its longitudinal axis. The pin 193 extends through the cylindrical support housing 195 via a threaded hole and has a rotary knob 192 on the outside. By now turning the rotary knob 192 the pin 193 will move outwards or inwards with respect to the support housing 195 as a consequence of the threaded engagement 196 with the support housing 195. During this movement the respective cylinder segment 81, 82 or 83 will correspondingly move radially outwards or radially inwards. It will be clear that the embodiment according to FIG. 14b can easily be implemented in that shown in FIG. 13. The operating knob 188, the pin 190, the gear 191, the planetary wheels 88 and the toothed ring 87 will then be dispensed with. With regard to the toothed ring 87 it is pointed out that instead of this it is possible to extend the support housing 195. The racks 89 will be replaced by the threaded pins 193 with rotary knob 192.

As will furthermore be clear with reference to FIGS. 14a and 14b, the so-called cylinder segments 81, 82 and 83 can essentially have any desired shape and number. They definitely do not have to be cylinder segments. They can be straight, as it were flat, plate-like elements, or also curved segments having a curvature other than a cylinder curvature. If the stabiliser is used to stabilise one or more vessels, the segments can also consist of one, two or multiple parts which essentially together form a casting of the entire or partial wall of this vessel or these vessels. The adjustment mechanism can then be used in such a way that the segment parts are brought towards one another, after which the segment parts can be joined to one another, optionally by means of coupling means. For such a use provision is made according to the invention that the adjustment mechanism is equipped for making a movement where the segment parts move towards one another or away from one another in a straight line or curve instead of in the radial plane (not shown here).

According to the invention the cylinder segments, which essentially contain the vacuum nozzle(s) of the stabiliser, can also be so constructed that they can be coupled to and/or uncoupled from the rest of the stabiliser, including vacuum duct. If the segments are uncoupled from the rest of the stabiliser in the body, these segments can remain behind in the body as a functional or non-functional implant after fixing by means of suturing, mechanical fixing techniques, including those as described in WO 00/24339 and WO 00/44311, both in the name of the same Applicant as the present application, tissue adhesive or another fixing technique or combination of techniques. Furthermore, it will be clear from FIG. 14b in particular that the support housing certainly does not have to be of cylindrical construction. It will furthermore also be clear from FIGS. 13, 14a and 14b that after positioning the stabiliser the applicator can be fed by its distal head to the destination via the hollow support housing 195 and the through the segments 81, 82 and 83.

One application for a stabiliser according to FIGS. 13, 14 is shown on the basis of FIG. 15. The only difference compared with FIGS. 13 and 14 is that for the application according to FIG. 15 a stabiliser is needed which has six cylinder segments provided with suction nozzles, one cylinder segment of which can be of completely straight construction and held immobile, whilst the other cylinder segments are jointly movable in the radial direction. The number of cylinder segments can also consist of 2, 3, 4, 5, 7, 8 or more. Incidentally, it is pointed out that both in the case of the embodiment according to FIGS. 13 and 14 and in the case of a variant thereof suitable for FIG. 15 the so-called cylinder segments do not necessarily have to be a section from a cylinder; they can also be simply straight or curved in some other way.

Instead of first narrowing the valve annulus using the cylinder segments of the stabiliser and then fixing a valve ring fixing device, which has a more or less fixed shape, in place, it is also possible according to the invention first to fit a valve ring fixing device in place, which device by virtue of its memory properties can assume a smaller diameter, it being possible for the assumption of this smaller diameter optionally to be caused and/or supported by bringing the cylinder segments towards one another. A flexible valve ring of this type can also be capable of moving with the natural movements of the valve annulus, that is to say a smaller surface area during the systole and a larger surface area during the diastole of the heart. Such a flexible valve ring can, of course, also be introduced after the valve annulus has first been narrowed using the cylinder segments. The fixing device can consist of tubular elements here. A metal wire that forms a closed ring can, for example, have been fed through these hollow elements. This wire can have so-called memory properties, for example can be made of Nitinol or of memory plastics (shape memory polymers), but other materials which have a resilient action can also be used. When positioning the tubular elements the wire is stretched out. After anchoring the tubular elements to the valve annulus and removing the support member and/or optionally an obstructing member, the wire contracts to the shape it was given beforehand or the wire is constricted in some other way; in this way the tubular elements are moved towards the centre and the surface area that is surrounded by the valve annulus is reduced. The space between the tubular elements and the flexible wire can be covered with materials tolerated by the body, such as, for example, textile, such as Teflon and/or Dacron, or memory plastics (shape memory polymers). Incidentally, all components mentioned in this application can be completely or partially covered with such materials tolerated by the body. Instead of the wire being closed and curling up, the wire can also be open, the ends sliding over one another when they come together, either on the one side or on the other side of the ring that the wire forms. FIG. 15 shows highly diagrammatically the dilated vessel wall tissue 90 at the location of a mitral valve. The stabiliser has a first fixed suction head 91 and five suction heads 92, 93, 94, 95 and 96 that can be moved in the radial direction. A vessel wall in the constricted state is shown by a broken line in FIG. 15, the suction heads 92-96 also being shown in the position in which they have moved radially inwards.

FIGS. 16 and 17 show, in a highly diagrammatic view, a mitral valve ring which, as a variant on what is shown in FIG. 15, is able to be fixed in the wide state to the surrounding vascular tissue and then, after releasing the vascular tissue to which it has been fixed, to constrict. In order to achieve this the mitral valve ring 270 is made up of, in this case, eight elements 271-278 to be fixed to the vascular tissue. The way in which these elements can be fixed to the surrounding vascular tissue can be effected (not shown) according to the technique as shown in FIG. 8, or according to other techniques, including those disclosed in WO 00/24339 and WO 00/44311, or by suturing, or by stapling or by making use of a tissue adhesive or a combination of techniques. The method of fixing the elements 271-278 can, however, also be effected as will also be described below on the basis of FIGS. 16a, 16b, 17a and 17b. The elements 271-278 are held in the widened state by means of spreader arms 280 with grippers 281. The arms 280 with grippers 281 form part of an applicator which, incidentally, is not shown. Springs 279 are provided between the elements 271-278. As soon as the elements 271-278 have been fixed to the surrounding vessel wall tissue, the arms 280 with grippers 281 can be removed, or at least moved radially inwards. This can, for example, take place in the same way as the spokes of an umbrella are collapsed and extended. If the arms 280 are as it were pulled together or folded together, the elements 271-278 will be pulled towards one another by the intermediate springs 279 and thus locally constrict the bloodstream. The advantage of the springs is that these allow flexibility so that the diameter of the constricted passage can vary to some extent under the influence of internal pressure as a consequence of the pumping of the heart, as is natural per se. The valve prosthesis rings known from the state of the art are either (semi)-rigid or flexible, but in all these cases the total surface area of the passage during the heart cycle is more or less fixed. The valve prosthesis rings according to the invention, however, allow an increase in the total surface area of the passage during the diastole of the heart chamber and a reduction thereof during the systole of the heart chamber. Furthermore, the valve prosthesis rings according to the invention make it possible for the natural valve annulus at that location to continue to assume its changing anatomical shape during the heart cycle.

FIG. 17 shows the ring prosthesis 270 from FIG. 16 in a fixed position. As FIG. 17 shows, in the fixed position the springs 279 will be shorter, so that the surface area spanned by the ring prosthesis 270 according to FIG. 17 is smaller than was the case in the state shown in FIG. 16. As FIG. 17 shows, the elements 271-278 are anchored by means of anchoring members 283, 284 in the surrounding vessel wall tissue (not shown).

With reference to FIGS. 16a and 16b, the anchoring members 283 and 284 are formed by making punched holes 285 in the outward-facing surface of the elements 271-278, which punched holes can be, for example, V-, U- or pin-shaped. The open ends of these punched holes 285, which in this case are V-shaped, face one another. The V-shaped punched holes 285 each delimit an anchoring member, i.e. 283 and 284. This can clearly be seen in FIGS. 16a and 16b, which show a view of element 273, or, respectively, a longitudinal section of element 273, from the outside. The anchoring members 283 and 284 can have been brought under pretension, such that when they are located in the plane of the respective element 271-278 a resilient force oriented outwards acts on the element here. In order, in this case, to hold the anchoring members 283 and 284 in the position located in the plane of the respective element 271-278, an obstructing member 282 is provided around the ring prosthesis 270.

After the ring prosthesis 270 has been brought to its destination, the obstructing member 282 will be removed. To this end the obstructing member 282 can be, for example, a hose-like sleeve that is pulled away perpendicularly to the plane of the drawing in FIG. 16. The anchoring members 283 and 284 on each element 271-278 will then swing outwards under the influence of the resilient force that has already been mentioned, as is shown in more detail in FIG. 17a by means of a section. During this movement the anchoring members 283 and 284 will bore into surrounding vessel wall tissue and, moreover, also be able to pinch surrounding vessel wall tissue as it were firmly between them, which can also contribute to anchoring. Swinging of the anchoring members 283, 284 outwards can also be achieved without pretension by exerting a mechanical force on these anchoring members 283, 284 from the inside with the aid of an accessory instrument and/or applicator, as a result of which these anchoring members are pushed radially outwards. In this case obstructing member 282 can be completely dispensed with. The direction in which the anchoring members 283, 284 swing radially outwards does not incidentally always have to be precisely in the horizontal flat plane of the ring. By punching the anchoring members 283, 284 at an angle of 90° from, for example, the cylindrical elements 271-278, the direction of swing can also be combined with the vertical plane, as a result of which this direction is able to adapt to the local anatomy of the tissues.

With reference to FIGS. 16 and 17 it is pointed out that the elements 271-278 can be mounted directly on the vacuum nozzles of the stabiliser so that at the same time as positioning the vacuum nozzle segments (see, for example, the segments 91-96 in FIG. 15), the ring prosthesis elements 271-278 are brought to their destination. With this arrangement it is optionally conceivable that the vacuum suction takes place through the elements 271-278, for example via the V-shaped punched holes 285. In this sense the ring prosthesis elements 271-278 can then be regarded as detachable suction nozzles of the stabiliser, the ring prosthesis elements 271-278 being of double-walled (hollow) construction. With this arrangement it is even conceivable that the vacuum holds the anchoring members 283, 284 in the pretensioned state under resilient force and that the obstructing member 282 can be completely dispensed with. The vacuum then only has to be removed in order to fix the ring prosthesis. Optionally, removal of the vacuum can take place for each element 271-278 individually, for each pair of elements 271-278 or optionally for all elements 271-278 at the same time.

If the ring prosthesis elements 271-278 are of double-walled construction, optionally distributed over several compartments, these elements can also be attached to the tissue with the aid of tissue adhesive instead of by (or supplementary to) punched holes 285 and anchoring members 283, 284. For this purpose use can be made of separate adhesive ducts for supplying adhesive to these hollow elements, but all or part of the vacuum duct can also be used for supplying adhesive. If the hollow structure of the ring prosthesis elements 271-278 has been divided into several compartments, it is possible, for example, first to use all these compartments to provisionally suck the elements tightly to the tissue. The vacuum in one half of the compartments is then, for example, removed and this half filled with adhesive. After this adhesive has set, the vacuum over the other half of the compartments can then also be removed and this half also filled with adhesive, after which all elements are completely fixed to the tissue. Of course, the adhesive technique and provisions for this that have been described here can also be used in combination with other fixing devices where the elements form a complete or virtually complete ring, including those as described in WO 00/24339 and WO 00/44311, both in the name of the same Applicant as the present application, and in particular are also applicable to the fixing of rings in the case of a valve prosthesis ring, as is used in the case of valve replacements and/or repairs of heart valves.

With reference to FIGS. 16 and 17 it is furthermore pointed out that the elasticity for the ability to adapt shape during the transition between the systole and diastole can also be achieved by using a sort of zig-zag ring parts instead of by means of springs 279. The entire ring prosthesis can also be constructed as a sort of zig-zag ring or spring ring. The zig-zag pattern then makes stretch and shrinkage possible during the transition from systole to diastole and vice versa.

With reference to FIG. 17b, the stabiliser with adjustment mechanism can also be used in combination with a closed or open valve ring 290 which has been designed for use in combination with the insertion of individual staples (not shown). Such a valve ring 290 can consist of a rigid or flexible ring 291 which has, at the periphery, a number of fixing projections 292 which extend radially outwards with respect to the ring and on which one or two transverse bars 293, 294 are arranged for fixing the staples (not shown). After all, the staples must be inserted parallel to the ring or ring parts because if they were inserted transversely over the ring they could damage the valve leaves themselves. By now first bringing the stretched valve ring tissue towards the ring 291 with the aid of the adjustable stabiliser or in some other way, the staples can be inserted between the ring 291 and a transverse bar 293 or between two transverse bars 293, 294. If a flexible material, for example bendable metal or plastic, is used as material for the fixing projections, the fixing projections can even be bent accordingly during the operation such that these projections fit well with the shape of the tissue surrounding the annulus. Of course, the staples must be inserted parallel to the valve annulus a safe distance away from the valve leaves themselves, so that these are not damaged.

Instead of [lacuna] transverse bars, the ring can also be so constructed that each fixing projection is joined to a second ring which is parallel to and on the radial outside of the first ring. The fixing projections thus form a sort of transverse connection like the treads of a flight of stairs, it being possible for transverse bars 293, 294 to be dispensed with.

As another variant, such a valve ring prosthesis that is to be stapled can be combined with the ring prosthesis as described in FIGS. 16 and 17, anchoring of the ring prosthesis elements 271-278 being effected not by anchoring members 283, 284 but as described above by inserting and/or firing in staples firmly or loosely positioned between transverse bars on fixing projections, which in this case can then each individually be joined to the individual ring prosthesis elements 271-278, likewise in a manner oriented radially outwards. According to the invention it is also possible to insert and/or fire in all or several staples at the same time. The staples can also already form part of the fixing projections and then themselves serve as deformable transverse bars and/or replace these.

The shape of a mitral valve ring or parts thereof and fixing techniques described above can also be applicable to other heart valves, such as, for example, the tricuspid valve where the shape of the ring (sections) has to be adapted to the anatomy of such a valve, as is known from the state of the art. The fixing techniques described for securing a mitral valve ring or parts thereof can also be used when fixing a valve prosthesis, or in combinations with other fixing techniques, including those as described in WO 00/24339 and WO 00/44311, both in the name of the same Applicant as the present application.

The present invention also relates to a method for positioning a fixing device in or around a passage surrounded by vessel wall tissue. In accordance with this method the vessel wall tissue at the intended location for the fixing device is stabilised by sucking this tissue tightly against a stabilisation device by means of vacuum. With this method after the tissue has been sucked on tightly the intended location can correspond to the bottom edge of the stabiliser. Subsequently, optionally after measuring the distance between the distal bottom edge of the stabilisation device and the precise intended location, the fixing device will be fed by means of an applicator towards the desired location until a stop member provided on the applicator comes to a stop against a stop member provided on the stabilisation device. The position of one of the two stop members with respect to the stabilisation device or applicator (depending on what the stop member concerned is fixed to) can be adjusted if appropriate, depending on the previously measured distance between the distal end of the stabilisation device and the desired location for the fixing device. In this way a fixing device can be positioned with high accuracy in a location that, for example is moving, in the case of a beating heart, or that usually is pushed away as a consequence of feeding in an applicator.

FIG. 18 shows a fourth variant of a stabiliser according to the invention which, in particular, is suitable for an inclined "end-to-side" anastomosis. The stabiliser 100 consists of a hollow 106 double-walled working duct 101 having, at the distal end, a saddle-shaped suction nozzle zone 102 with one suction nozzle or a greater or smaller number of suction nozzles. These suction nozzles are each oriented perpendicularly to the plane determined by the saddle shape and will be located some distance away from the elliptical passage 114 in the vessel wall so that an elliptical ring 107 of vessel wall tissue still remains between the passage 114 and the inside wall 109 of the working duct 101. The ring 107 provides a gripping surface for flange fingers 313, 314 (FIG. 8). The opening 114 can optionally be made after positioning the stabiliser or can already have been made beforehand. A flange part 103 that is likewise saddle-shaped can be fixed to the bottom of the working duct 101, which flange part 103 is optionally completely or partially in communication with the hollow 106 double-walled working duct 101. Sensors 104 can be positioned on this flange part 103. By means of these sensors it is possible to move the whole over the target vessel 105 and thus to seek the correct location for the anastomosis. These sensors can, for example, consist of Doppler or duplex echo sound heads or other imaging or current-displaying techniques, the shape and size of which is determined by the application. With regard to the correct location it is pointed out that it is important in particular to centre the working duct precisely in the middle on the longitudinal axis of the blood vessel 105. Instead of, or supplementary to, sensors 104, the flange part 103 can also be provided with, in particular pointed, notches 108 or possibly projections. The notches 108 or projections can be visually positioned by the surgeon above the longitudinal axis, i.e. the centre, of the blood vessel 105. As already stated above, one or more markers for a navigation system can be arranged on flange part 103 or other parts of the stabiliser, preferably as close as possible to and/or around passage 114. If vessel 105 is freely accessible, or is exposed for this purpose, suction nozzle zone 102 and/or flange part 103 can be located around all or part of the cylindrical periphery of vessel 105, but can also have a shape such that it extends over the surrounding tissue on either side of vessel 105, such as, for example, can be the case with coronary arteries located at the surface which are embedded in the epicardial tissue. By this means a fairly flat shape is obtained which is able to bend somewhat with the surface radius formed by the heart surface (not shown). As will be clear, the working duct 101 can also be perpendicular, instead of inclined, on the flange 103 or the blood vessel 105.

By inserting an applicator of suitable construction, optionally an applicator according to FIGS. 1-7 adapted for a vessel fixing device, into the stabiliser 100, an anastomosis fixing device, for example one from WO 00/24339 in the name of the Applicant, can be positioned. This applicator will then be pushed into the working duct 101 or 111 to a predetermined or optionally preset depth by means of stop means, which are not shown. The stop formed on the stabiliser 100 can optionally be formed by the proximal top edge 106 thereof.

An example of a procedure for producing an end-to-side anastomosis will be described below with reference to FIGS.

Figure 19:
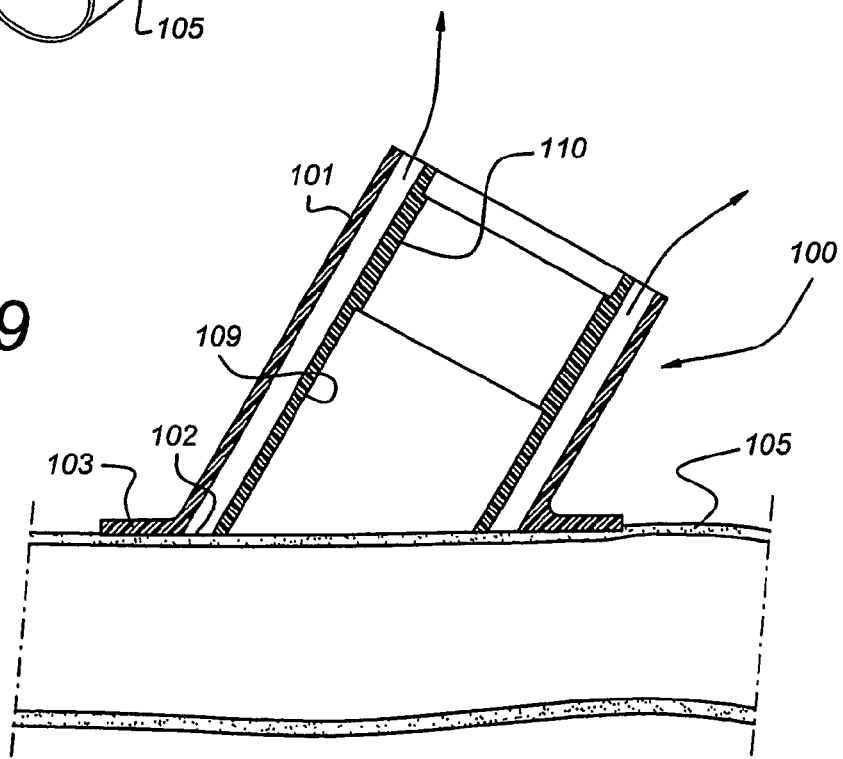

19 to 23. FIG. 19 shows a blood vessel 105 to which a bypass blood vessel will be connected at an angle. For this purpose use is made of a stabiliser 100, such as that which has been described with reference to FIG. 18. Even before a passage has been made in the blood vessel 105, this stabiliser 100 is positioned laterally on the blood vessel 105 at an angle and sucked tightly thereto by applying suction to the double-walled working duct 101. The suction nozzle running in the peripheral direction then sucks tightly to the zone 102. For internal guiding of instruments to be inserted in the stabiliser 100 the inner jacket 9 of the stabiliser 100 can be locally provided with a peripheral rib 110.

Figure 20:
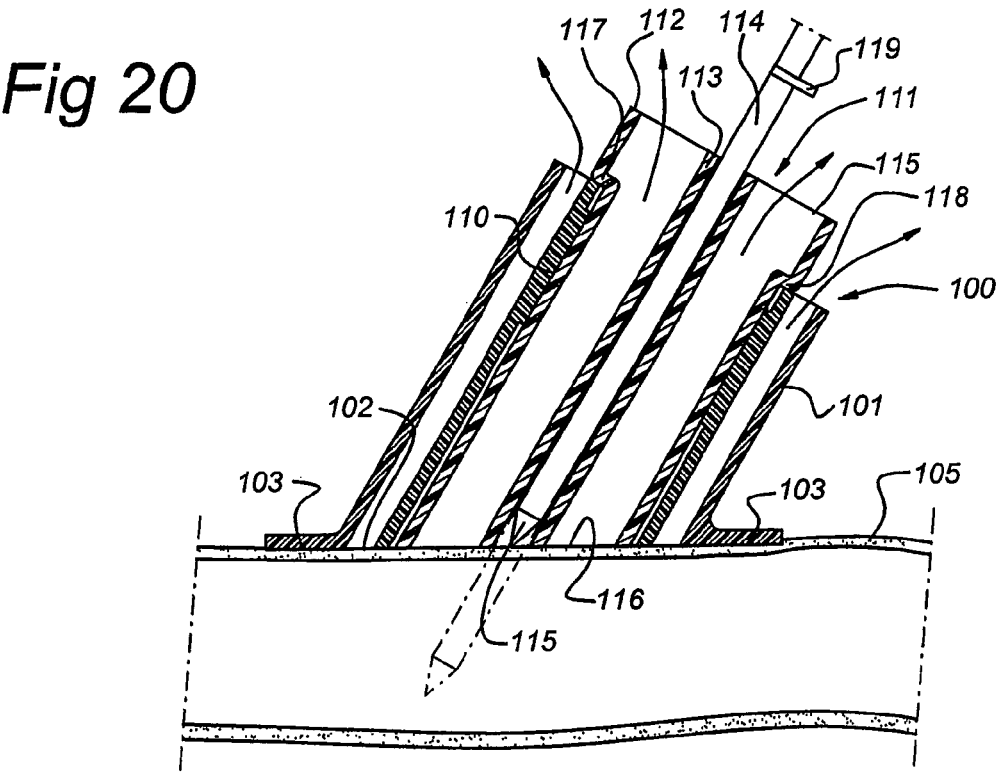

With reference to FIG. 20, an instrument 111 is inserted in the stabiliser 100, which together form an assembly 100, 111 according to the invention. The instrument 111 is in this case a guide probe guide for guiding a guide probe 114 having a sharp perforation point 115. Here the guide probe guide consists of a tubular inside wall 113 with, around it, a hollow space 115 that is closed on the outside by a wall 112. Via the hollow space 115 it is possible optionally, but this is not absolutely necessary, to apply suction to the oval-shaped zone 116 of the outside wall of the blood vessel 105. This guide probe guide 111 is provided with a stop 117 that comes to bear on a stop surface 118 on the stabiliser 100. In this way it is ensured that the end of the instrument 111 facing the blood vessel 105 assumes a more accurate position with respect to the bottom end of the stabiliser 100; in this case the two bottom ends are precisely aligned. After the guide probe guide 111 has been positioned, a perforation can be made in the blood vessel 105 by means of a pointed 115 guide probe wire 114, by, as is indicated by broken lines, puncturing the wall with the guide probe 114. In this context it can be advantageous to suck the zone 116 tightly to the guide probe guide 111 by means of suction, since it is then possible accurately to ensure the location at which the wall of the blood vessel 105 is precisely pierced. After all, the wall will then not first be pushed away by said point 115 at that location before piercing of the blood vessel 105 by point 115, which would make determination of the location of piercing less accurate.

After having pierced the blood vessel 105, the guide wire 114 provided with a sharp point 115 can optionally be replaced by a guide wire with a point that is not sharp. The reason for this is to prevent the sharp point from being able to damage the blood vessel 105 on insertion further into this blood vessel. As desired, the guide wire could be fed through the blood vessel 105 over a small to large distance. This can also be useful if the aim is not at all to produce an end-to-side anastomosis but merely, for whatever reason, to feed a guide wire or other instrumentation through a blood vessel to a desired location for investigation or a medical intervention. It will be clear that for this purpose the guide wire can optionally be made curved or can be of flexible construction, as, incidentally, is not unknown from the state of the art.

So that it is not possible to overshoot when piercing the vessel wall 105 with the sharp point 115 and thus possibly damage the opposite portion of the vessel wall, a stop 119 can be provided on the guide wire 114, which stop comes to a stop on, for example, the inside wall 113 of the guide wire guide 111. It will be clear that if the guide wire guide 111 is provided with a suction nozzle, this, together with the guide wire 114 provided with a stop, forms an assembly 111, 114 according to the invention, the guide wire guide 111 then being the stabiliser and the guide wire 119 provided with a stop being the instrument. It is also possible first to puncture blood vessel 105 using a sharp pointed guide wire 114/115 or a blunt guide wire 114 in a sharp needle, after which, around the guide wire, assembly 111, 100 is placed on the outside wall of blood vessel 105, as a result of which a central position of the stabiliser 100 over blood vessel 105 can be ensured.

Figure 21:
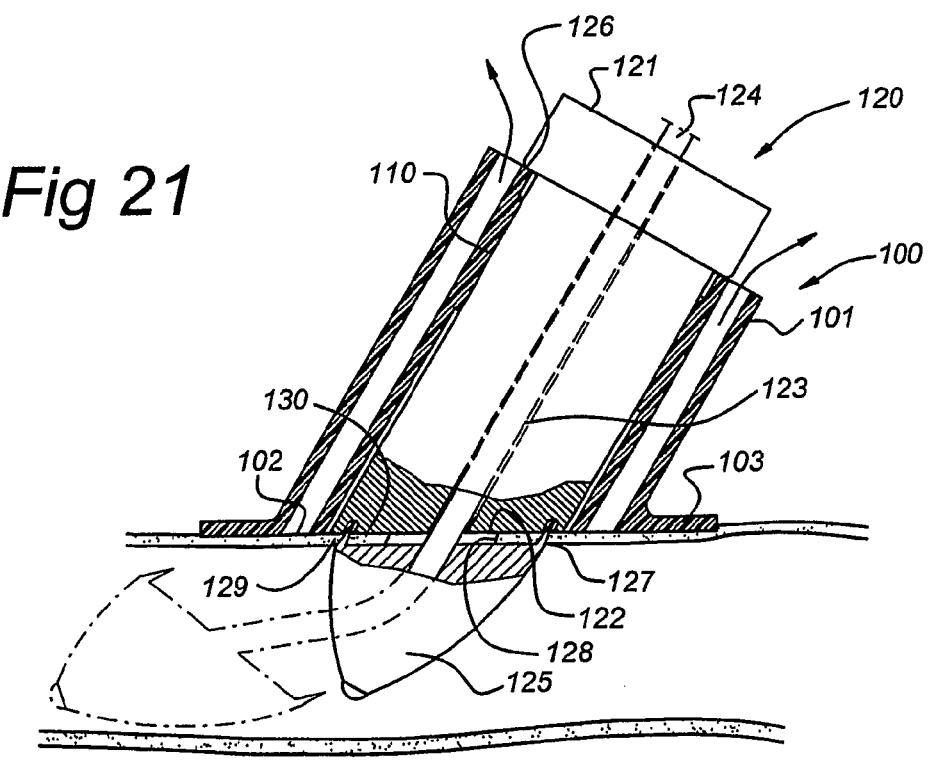

If it is then desired to attach a bypass to the blood vessel 105, it is important that the passage created in the vessel wall 105 using the guide wire is enlarged. This can be effected using a so-called dilator, by means of which the opening is stretched by pushing an object of increasing diameter through it. The disadvantage of a dilator is that, especially in the case of relatively substantial stretching of the passage, there is a risk of tearing of the vessel wall tissue. For this reason it is usually preferred to work with a punching technique. In the case of a punching technique the passage will usually be enlarged in steps by pushing a punching member having a diameter larger than that of the opening through it, then allowing the passage to become smaller again as a consequence of the tissue springing back so as then, whilst punching, to withdraw the punching member against a die and so cutting out an oval or circular piece of tissue. This step can then be repeated a number of times using increasingly wider punching members in order to enlarge the passage stepwise to the desired size. An example of this punching technique is illustrated in FIG. 21, which differs from FIG. 20 in the sense that the guide wire guide 111 has now been replaced by a punching device 120. The punching device consists of a punch guide 121 that fits tightly in the guide 110 of the stabiliser 100.

The head section of the punching device 120 located at the bottom in FIG. 21 comprises a die with a guide passage 123 in the middle for the operating wire or rod 124 of the punching member 125. The punching device 120 has a stop 126 by means of which the punch guide 121 is able to come into contact with the stabiliser 100 in order thus to position the location of the die 122 with respect to the suction nozzle 102 of the stabiliser 100. In this case the die 122 is aligned with the suction nozzle 102. However, it is also conceivable to position the die 122 somewhat higher than the suction nozzle 102. The point at issue is that the position of the die 122 with respect to the suction nozzle 102 is determined by the stop 126. As can be seen in FIG. 21, the punching member 125 has been pushed by means of the wire 124 through the already widened passage 128, as is indicated by broken lines, in order then to pull back this punching member 125 by means of the wire 124 until the cutting edge 127 of the punching member drops into the die 122 so as thus to widen the passage 128 to a diameter determined by that of the cutting edge 127.

In order to be able to hold the vessel wall tissue located around the punching member accurately positioned during punching there is, according to the invention, a possibility of providing the punching member with a loop-shaped suction nozzle 129, in a manner corresponding to that in the case of the stabiliser, which suction nozzle 129 holds the vessel wall tissue sucked tightly precisely around the cutting edge 127. In order to be able to hold the—in this case elliptical—ring of the vessel wall tissue that has been cut out firmly on the die 122, a loop-shaped suction nozzle can optionally also be provided at the location of 130. If a loop-shaped suction nozzle 129 is provided the punching device 120 can be regarded as an assembly according to the invention, the wire 124 with punching member 125 then being the instrument and the component 121 the stabiliser. According to the invention such a punching member can also be used to remove valve tissue, parts thereof, or other tissue, optionally after decalcification thereof, from a hollow organ. Instead of mechanical cutting forces it is also possible to use other forces, such as, for example, electrical, sound or laser power sources during this operation. The punching member can have diverse shapes, such as, inter alia, circular, elliptical or oval, but also bean- or kidney-shaped, such as can be suitable when, for example, punching out a mitral valve.

Figure 22:
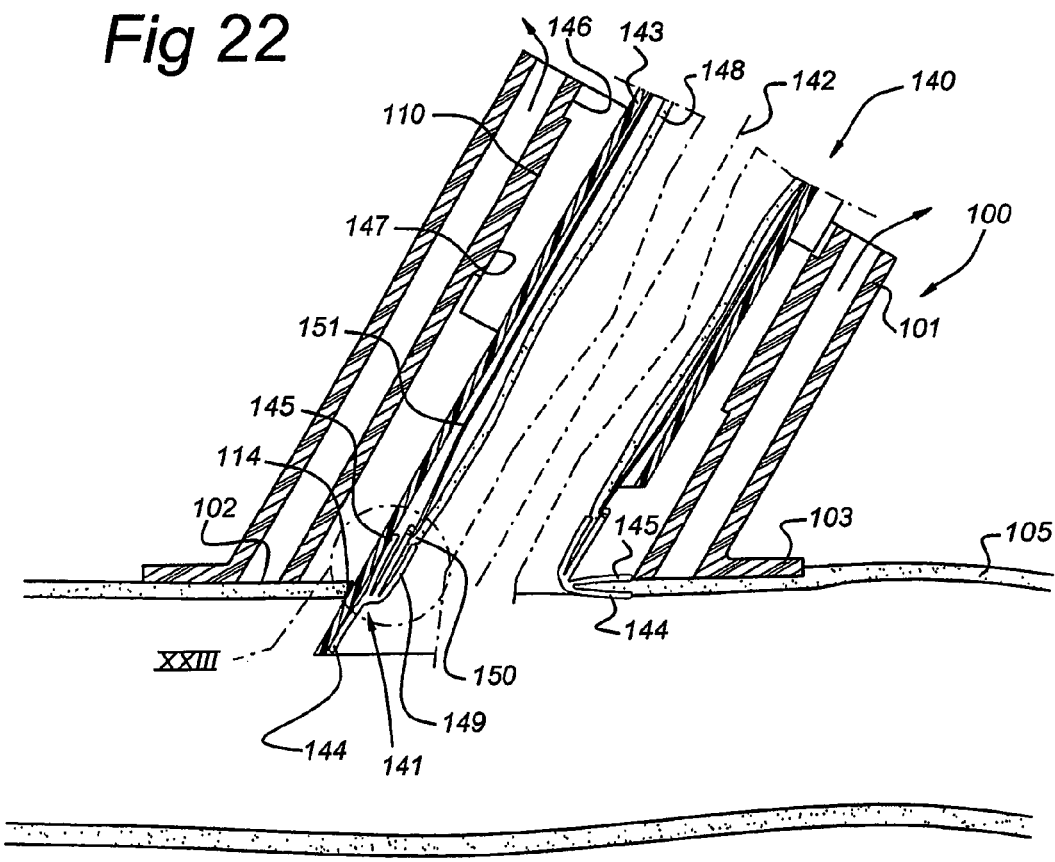
Figure 23:
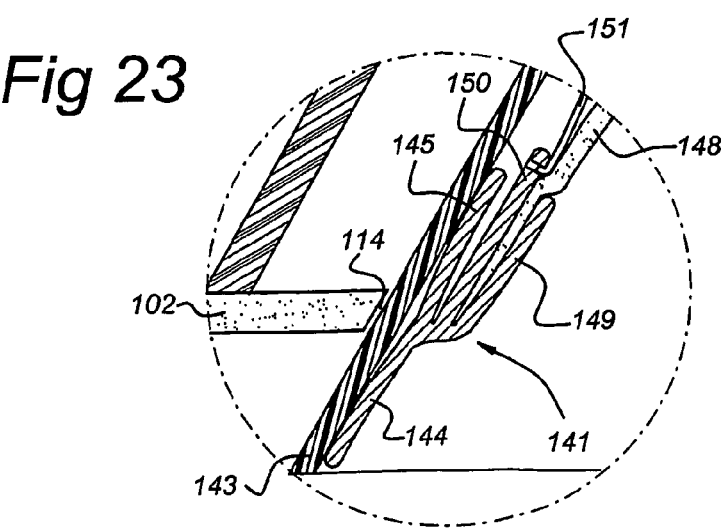

FIGS. 22 and 23 show an assembly according to the invention comprising a stabiliser 100 and an applicator 140 for securing a fixing device 141 for an end-to-side anastomosis in the passage 114 in the blood vessel 105. Although the mutual stops on the applicator 140 and stabiliser 100 are not shown in FIG. 22—after all only the bottom part of the applicator 140 is shown diagrammatically—it will be clear that this can be implemented in accordance with what is shown in FIG. 1 or also—within the scope of the invention—in some other way.

FIG. 22 shows on the right of the axis 142 the fixing device 141 in the completely fixed position, but without the applicator 140 yet being completely removed. On the left-hand side of the axis 142 the fixing device 141 and also the applicator 140 are shown in the initial position—with correct positioning—just before the fixing actions by means of the applicator 140. Here the fixing device 141 is positioned somewhat inclined with respect to the longitudinal axis of the applicator (gripper arms and sleeve) and not perpendicularly thereto, as in the case of a right-angled vessel join.

In FIG. 22 and FIG. 23, showing the detail XXII circled in FIG. 22, 143 indicates the sleeve, which is comparable to the sleeve 21 in FIGS. 1 to 6. The mode of operation of the fixing member 141 is comparable to that of the fixing device 315 from FIG. 8 in the sense that it has distal flange finger 144 (cf. distal flange fingers 313 in FIG. 8) and proximal flange fingers 145 (cf. the proximal flange fingers 314 in FIG. 8). When the sleeve 143 has been pulled back up, as is shown on the right-hand side, the distal flange fingers 144 and proximal flange fingers 145 have the room to flip outwards so that they are able to clamp vessel wall tissue 105 between them. The blood vessel 148 to be joined is joined to the fixing device 141 beforehand, or optionally later, by securing the bottom end thereof between a tubular part 150 and an inner flange or inner flange fingers 149 (also see, for example, FIGS. 24-26 and the associated description). However, this can also be achieved in a different way, for example by suturing to tubular part 150, in which case inner flange 149 can then be dispensed with. So that the fixing member 141 can be held firmly by the applicator, the tubular part 150 is provided with holes or cut-outs in which pins pointing radially outwards (shown) or radially inwards (not shown) at the bottom end of grippers 151 are able to engage; see the detail in FIG. 23.

So that the position of the applicator in the radial direction with respect to the stabiliser 100 is reliably determined unambiguously, it is advantageous to provide the sleeve 143 with a thickening 147 that interacts with the guide 110 of the stabiliser 100. The thickening 147 can be provided at the top with a further radial projection 146, that can make contact, as a stop, on the top of the guide 110 of the stabiliser. In this way the lowered position of the sleeve 143 can be unambiguously determined with respect to the stabiliser 100.

As will be clear in the case of FIGS. 19 to 22, the stabiliser 100 will be connected to a suction source during the actions described, in order to suck the vessel wall tissue 105 tightly from the outside with the suction nozzle 102.

FIGS. 24 to 26 show an accessory 159 for fitting a fixing device 141 on a blood vessel 148, which, for example, can be joined laterally to a blood vessel 105 in accordance with FIG. 22. As will also be apparent from the following description, the accessory 159 also makes it possible to insert the blood vessel 148, with fixing device 141 fixed thereto, into an applicator, or at least into the sleeve 160 thereof (comparable with the sleeve 143 in FIG. 22 and sleeve 21 in FIGS. 1 to 6).

The accessory 159 consists of an insertion part 161 that is inserted in one end 169 of the blood vessel 148 and that is provided at the periphery with suction nozzles 162 in order to suck said blood vessel 148 tightly after applying a vacuum. The insertion part 161 is also provided with fingers 168 which extend to close to the free end 169 of the blood vessel 148 in order to hold this free end fixed in its position for subsequent positioning in the fixing device 141. The insertion part 161 is mounted on a hollow suction tube 163 via which the insertion part 161 can be manipulated and via which a vacuum can also be applied to the suction nozzles 162. The insertion part 161 is inserted into the sleeve 160 from below and then guided out of the sleeve 160 via a side opening 167 in said sleeve 160. Here the side opening 167 is shown relatively close to the bottom end of the sleeve 160. In practice, it will be possible for this opening 167 to be further away from the bottom end of the sleeve 160 or to be longer. The blood vessel 148 can be slid relatively easily onto the insertion part 161 protruding from the sleeve via the opening 167, in order then to be sucked tightly by means of the vacuum nozzles 162. As will be clear, the blood vessel 148 sucked tightly by the insertion part 161 can be drawn via the opening 167 into the sleeve 160 by pulling on suction tube 163, or, optionally, the blood vessel can be inserted in the sleeve 160 via opening 167. It will be clear that the blood vessel 148 sucked tightly by the insertion part 161 can optionally also be fed in via the proximal opening at the end of sleeve 160.

The accessory 159 furthermore optionally comprises an auxiliary sleeve 166 in which the fixing device 141 is held under tension with the distal flange fingers 144 and proximal flange fingers 145 straightened (see also FIG. 22 and the right-hand part of FIG. 8). The accessory furthermore comprises a fingered cap 164, the fingers 171 of which hold the inner flange fingers 149 in the position in which they are bent inwards. The cap 164 is mounted on a tube 165 and the suction tube 163 runs through the tube 165. By turning the tube 165 the inner flange fingers 149 will be released, after which they are able, under the influence of resilience, to spring outwards in the radial direction between the fingers 171, via the slots 170, into a position as is shown in FIGS. 25 and 26. It is also conceivable to push the cap 164 (vertically) upwards so as to release the inner flange fingers 149. The fingers 171 can then optionally be dispensed with. However, the insertion part 161 will have to allow some room for this pushing upwards, either by maintaining an adequate distance from the cap or by having an internal receiving cavity for this purpose. It is optionally also possible to construct 164 as a flat disc, fingers 149 taking up a position transverse to the longitudinal axis of the tubular member. This flat disc 164 can then be turned or moved in the vertical direction. In the case where 164 is moved towards insertion part 161 (upwards towards it), the flat disc must, however, then be allowed room at the bottom of insertion part 161. In the case where 164 is moved in the opposite direction to insertion part 161 (downwards), the flange fingers 149 must bend almost fully towards flange fingers 144, so as then, following release, to bend back fully again towards parts 150.

As has already been explained, the free end of the blood vessel 148 gripped by the insertion part 161 can be guided into the sleeve 160 by means of the insertion part 161 and the suction tube 163 in order then for the free bottom end 169 to be positioned between the tubular part 150 and the inner flange fingers 149. For this purpose the suction tube 163 will be pulled through tube 165. In order accurately to define the end position into which the bypass 148 is pulled into the sleeve 160, a guide system with a stabiliser stop 174 and instrument stop 175 is also provided. This guide system consists of an arm 172 that is mounted on tube 165 and is provided with a guide sleeve 174 acting as stabiliser stop. An arm 173 mounted suction tube 163 extends through guide sleeve 174, which arm 173, in turn, is provided with the instrument stop 175. When suction tube 163 is pulled a long way down with guiding, in accordance with the arrow, the instrument stop 175 then comes to a stop on the stabiliser stop 174. This guide system with stops 174, 175 is important in particular when the cap 164 has to undergo a movement in the longitudinal direction of the sleeve 160 in order to be able to release the inner flange finger 149. If this is not necessary, it is optionally conceivable that the convex top of the cap 164 and the concave underside of the insertion part 161 are used as stabiliser stop and instrument stop, respectively. Subsequently, at least in the illustrative embodiment shown, the cap 164 will be turned so that the inner flange fingers 149 spring outwards via the cut-outs 170 between the fingers 171 and between the fingers 168 in order to clamp the bottom end 169 of the blood vessel.

This clamped position is shown in FIG. 25. (The guide and stop system shown in FIG. 24 is not shown again in FIG. 25 or in FIG. 26). Here the fixing device 141 is still in the auxiliary sleeve 166 which has been pushed onto the bottom end of the sleeve 160. By now continuing to apply, or reapplying vacuum to the suction nozzle 162 and pushing the suction tube 163 upwards, optionally in combination with the tube 165, the unit formed by blood vessel 148 and fixing device 141 can be pushed upwards out of the auxiliary sleeve 166 into the bottom end of the sleeve 160. However, it is better to use the gripper arms 151 of the applicator for this purpose. These gripper arms can grasp the vessel fixing device 141 from above or optionally from below. Insertion part 161 and cap 164 can then already have been removed, but these can also be used to support the gripper arms 151. The auxiliary sleeve 166 can then be removed, after which previously described actions using an applicator for fixing the blood vessel 148, to, for example, a blood vessel 105 for an end-to-side anastomosis can be carried out or, optionally, an end-to-end anastomosis can also be produced. If the fixing device has already been placed in sleeve 160 in advance, the auxiliary sleeve 166 can then be dispensed with. In the case of an end-to-end anastomosis, where the anastomosis is produced at the end face of the target vessel, the distal flange fingers 144 will not so much be under spring tension, but mainly the proximal flange fingers 145 will be under spring tension in order, after removal of the sleeve 160, to flip through 180° from the upward-pointing position shown in FIG. 26 into a downward-pointing position. In the last-mentioned, downward-pointing position the proximal flange fingers 145 will then be able, together with the distal flange fingers 144, to grasp one end of a further blood vessel in a manner corresponding to the manner in which the end 169 of the blood vessel 148 has been grasped.

With reference to FIG. 26 it will be clear that after an anastomosis has been produced, that is to say after joining the blood vessel 148 to another blood vessel, it must still be possible to remove the sleeve 160 and other parts of the applicator. This can be achieved by making the sleeve 160 and, if necessary, also the other parts of the applicator separable. Sleeve 160 and, if necessary, also the other parts of the applicator can, for example, be made in two parts, i.e. the half shown located behind the plane of the drawing and the, essentially identical, half, that is not shown and is located as a mirror image in front of the plane of the drawing. The plane of the drawing is thus coincident with the separating surface.

With regard to the actions described with reference to FIGS. 24-26 it is pointed out that these can also be carried out in a different sequence. For instance, it is possible, for example, first to slide the fixing member 141 from the auxiliary sleeve 166 into the sleeve 160 or to place it in the sleeve 160 in advance in some other way. Furthermore, it is also possible first to fix the blood vessel to the fixing member 141, which may have already been placed in auxiliary sleeve 166, and then to place the end 169 of the blood vessel with the fixing member 141 fixed thereto in the sleeve 160, optionally making use of the fact that said sleeve 160 is separable and/or of side opening 167. It is also possible to leave the fixing device in sleeve 166 and to make use of a connection between sleeve 160 and sleeve 166 that is so firm that by pulling sleeve 160 upwards sleeve 166 is also pulled upwards. For this purpose it is possible, for example, to provide facilities on both sleeves, or sleeve 160 can be introduced into sleeve 166 such that it can be compressed and joined thereto by expansion.

The technique as described in FIGS. 19 to 26 for use when fixing a vessel fixing device for an end-to-side anastomosis can also be used in whole or in part for an end-to-end or side-to-side anastomosis, fitting a port fixing device, a working duct, a cannula or another accessory in or on the wall of a blood vessel or hollow organ.

FIGS. 27 and 28 show, highly diagrammatically, a stabiliser 400 which can be used to produce a so-called side-to-side anastomosis. In this context FIG. 27 shows, highly diagrammatically, a perspective view and FIG. 28 a vertical longitudinal sectional view. The vessels shown are here always shown completely parallel to one another, but can also be mutually turned through 0-90 degrees with respect to one another, it being possible for the stabiliser components associated with the individual vessels to be able to turn with respect to one another, in any event insofar as the vessels have not yet been firmly joined to one another. The stabiliser 400, as shown here, is made up of three stabiliser bodies, i.e. a bottom stabiliser body 401, a middle stabiliser body 402 and a top stabiliser body 403. The middle stabiliser body 402 will preferably be of divided construction with, for example a dividing surface 404 perpendicular to the plane of the drawing according to FIG. 28.

The bottom stabiliser body 401 is provided with an arc-shaped curved cylinder segment-shaped recess 405 in which the bottom section of a blood vessel 410 can be accommodated. Correspondingly, the top stabiliser body 403 is provided with a curved, cylinder segment-shaped recess 406 for accommodating a section of a second blood vessel 411. The middle stabiliser body 402 is provided with two curved, cylinder segment-shaped cut-outs 407 and 408 which touch one another approximately in the middle of the central stabiliser body 402 in such a way that when stabiliser bodies are placed on top of one another two curved cylindrically shaped channels are formed which touch one another at the point of contact so as to be in communication with one another at that location via a generously sized passage.

As shown in FIGS. 27 and 28, blood vessels 410 and 411 can be accommodated in the curved, cylindrical passage. These blood vessels 410 and 411 can be secured in the assembly of the stabiliser bodies 401, 402 and 403 by means of vacuum nozzles 412, 413 and 414 after applying a vacuum. The vacuum nozzle 414 extends in elliptical or circular shape around the vertical passage 415 made in the central stabiliser body. The vacuum nozzle 414 can be a slit-shaped vacuum nozzle, but this can also be made up of a series of vacuum nozzles, which optionally can be distributed between compartments, which optionally can be in communication with one another. The vacuum nozzles 412 and 413 are constructed in a corresponding manner. These also extend in circular or elliptical shape and can consist of a single slit or a series of openings, it being possible for the vacuum nozzles to extend around the periphery and in the longitudinal direction of the vessels, parallel to cut-outs 405-408, so that vessels 410 and 411 are accommodated in a vacuum channel. If necessary, at the location of the ends of cut-outs 405-408, use can be made of a facility which temporarily compresses vessels 410 and/or 411 in order to obtain a good seal for the vacuum channel. Such a facility can consist of a half-moon-shaped partition which is made of a soft, resilient material, such as, for example, rubber. For reasons of clarity the respective vacuum ducts associated with the vacuum nozzles and the respective suction rods are not shown in FIGS. 27 and 28. These suction rods can lead to a common suction rod, but can also remain separate, one or several stabiliser bodies each keeping its own suction rod, optionally in this way forming a component of individual stabilisers. According to a particular embodiment of the invention it is possible for the stabiliser bodies to form part of or to be mounted on an adjustment mechanism which makes controlled opening or uncoupling and closing or connecting of the stabiliser bodies possible. The movement that the stabiliser bodies then make could then rather be in accordance with a straight or curved line, but can also be a radial movement, as described in FIGS. 13 and 14. With reference to FIG. 27, the stabiliser 400 also comprises a guide rod 416, for an instrument stop 417, fixed to the assembly of the stabiliser bodies 401, 402 and 403. The instrument stop 417 can be locked in an adjustable, or to put it more precisely settable, manner along the guide rod 416. A passage 418 for an instrument has been made in the top stabiliser body 403. An instrument 419, indicated diagrammatically by dash-and-dot lines in FIG. 28, can be inserted via this passage. This instrument will first make an opening in the top blood vessel 411 at 420 and will then make the openings 421 and 422 via which the blood vessels 411 and 410 make communication with one another. By means of a widening, the instrument 419 can come to a stop on the top surface of the top stabiliser body 403, which top surface then also acts as stop. In this case the guide rod 416 and instrument stop 417 are then superfluous. In order to make an opening in a vessel, instrument 419 can be constructed and used correspondingly to the accessories and techniques as shown and described in FIGS. 19-21, the passage surrounded by working duct 101 and the inside wall 109 thereof being comparable with the passage 418 in the top stabiliser body 403, and these accessories then preferably making an angle of 90 degrees with respect to the blood vessels 411 and 410.

In order to join the blood vessels 410 and 411 to one another at the location of the passages 421 and 422 it is possible to position, for example, a fixing device as shown in FIG. 8 with the aid of an applicator, for example an applicator adapted to this purpose as shown in one of FIGS. 1 to 6.

Stabiliser 400 as shown in FIGS. 27 and 28 is, as stated, made up of three stabiliser bodies. The essence is, however, that the vessels involved are temporarily held by one or more stabiliser bodies in a position such that controlled fixing of a joining device is possible remotely. After the join has been produced it is usually desirable to remove the stabiliser bodies, so that in this case the stabiliser bodies present at the location around the join itself will always be separable. Holding the two vessels in contact with one another can, however, also be effected by positioning both vessels in one stabiliser body, which, for example, can be flapped open and shut. It is also possible first to place the one vessel in a stabiliser body and then to place the other vessel in another stabiliser body and thereafter to connect both stabiliser bodies to one another. If it is then desired to remove the stabiliser bodies again, these must, for example, be constructed such that they are separable or can be flapped open in the longitudinal direction. It is also possible to leave stabiliser body 400 in the body, optionally after uncoupling from the remainder of one or more stabilisers, certainly if this stabiliser body is used in combination with gluing techniques, such as described in FIGS. 34, 35 and 36 of this application. Incidentally, the technique as described here in the form of a stabiliser body 400 for the production of a side-to-side anastomosis, is also applicable, with a few modifications, to the production of an end-to-side or end-to-end anastomosis.

FIG. 29 shows, diagrammatically, a further embodiment of an assembly 430 comprising a stabiliser 431 and an applicator 432 for producing an end-to-side anastomosis. Here the receiving blood vessel is indicated by 433 and the blood vessel that comes laterally into contact with this and is to be fixed is indicated by 148. The applicator 432 is essentially no different to the applicator described in FIGS. 24-26 (and comparable with that described in FIGS. 18-23). For this reason the same numbers as in FIGS. 24-26 have therefore also been used again for corresponding reference numerals. Reference can also therefore be made to these figures for the manner in which the blood vessel 148 making lateral contact and the fixing device 141 can be loaded in the applicator 432. The stabiliser 431 consists of a hollow tube 434 that is of widened construction at the receiving vessel and, by means of a saddle-shaped suction nozzle 435, sucks tightly to the receiving blood vessel 433 some distance away around the passage 436 made therein. So that the blood vessel 148 that comes into lateral contact can pass not only laterally through the sleeve 160 but also can pass laterally through the suction tube 434 of the stabiliser, the suction tube 437 is provided with a slot 437 that is open towards the receiving blood vessel. As far as the remaining further production of the end-to-side anastomosis is concerned, the sleeve 160 will be pulled upwards in the vertical direction in order to release the distal flange fingers 144 and proximal flange fingers 145, as has also been described with reference to FIGS. 22 and 23.

FIG. 30 shows, diagrammatically, in longitudinal sectional view, an assembly 450 of a stabiliser 451 and an applicator 452, derived from that in FIG. 29, for the production of a side-to-side anastomosis. The stabiliser 451 consists of a suction tube having a suction nozzle 452 at the bottom end that extends around the passages 453 and 454 to be joined to one another in the blood vessels 455 and 456. The applicator 452, consisting of a sleeve 457 with gripper arms 453 therein, has been inserted in the suction tube 451. The gripper arms 453 carry at a bottom end a fixing member 460 with distal flange fingers 461 and proximal flange fingers 462. Whilst the gripper arms 453 are held in place and thus hold the fixing device 460 in place, the sleeve 457 can be pulled vertically upwards, after which the distal and proximal flange fingers 461 and 462, respectively, are released so as to flip from their vertical position shown in FIG. 30 into an outward-pointing horizontal position under the influence of spring tension. During this movement the distal flange fingers 461 and proximal flange fingers 462 will clamp the vessel wall tissue around the passages 453 and 454 to each other. In the course of time this vessel wall tissue can then grow together at this location. Corresponding to what is shown in FIGS. 27 and 28, an additional passage 463 has been made in the top blood vessel 455 through which the assembly 450 has been inserted into the top blood vessel 455. This passage 463 will also still have to be closed after producing the join between the two passages 453 and 454. This can optionally be carried out using a fixing device similar to fixing device 460. However, the fixing device used for this purpose will have been provided with gripping means at the location of the gripping by the gripper arms 453 for fitting a cap herein. These gripping means can be, for example, internal screw thread, the cap then being provided with external screw thread. Use can also be made of a port fixing device that can be closed by a cap, as has already been shown in a few figures in WO 00/44311 and has been described on the basis of these. Instead of feeding in an assembly 450 of a stabiliser 451 and an applicator 452 through lateral opening 463 in blood vessel 455, it is possible also to feed in the assembly 450, or the applicator 452 on its own, through an end opening in vessel 455, insofar as this is available, to produce a side-to-side anastomosis. In this case the assembly 450 or the applicator 452 on its own will have to make a bend or angle of approximately 90 degrees at the location of the openings 453 and 454 or will have to have such a shape (not shown). In this case the stabiliser can also be constructed with a cylindrical shape (comparable to insertion body 161), which is located in vessel 455 on either side of opening 453 therein, or proximally or distally to said opening (not shown).

FIG. 31 shows an assembly according to the invention for producing an end-to-end anastomosis between two blood vessels 473 and 474. The assembly consists of a stabiliser 471 and an applicator 432 which essentially is the same as the applicator 432 in FIG. 29 and therefore has been provided with reference numerals accordingly. The fixing device by means of which the anastomosis is produced is also very similar to that which is shown in FIG. 29. However, the mode of action of the distal and proximal gripper members is somewhat different. In FIG. 31 the fixing device is indicated by 480. The reference numeral 481 corresponds to reference numeral 149 in FIG. 29 and reference numeral 482 corresponds to reference numeral 150 in FIG. 29. There are not yet any differences here. Reference numeral 483 corresponds to reference numeral 144 in FIG. 29 and reference numeral 484 corresponds to reference numeral 145 in FIG. 29. In the case of reference numerals 483 and 484, there are, however, differences to be pointed out. As far as loading fixing device 480 and blood vessel 474 in the applicator tube 160 is concerned, reference can again be made to the description for FIGS. 24-27. The stabiliser 471 consists of a suction tube that has a cylindrical suction nozzle 472 at its bottom end by means of which this suction tube engages on the lower blood vessel 473 from the outside by sucking on tightly. After the lower blood vessel 473 has been inserted in the suction tube 471 and sucked tightly by means of the suction nozzle 472, the applicator 432, which is already in the suction tube 471, can be pushed downwards so as to overlap the suction nozzle 472 with the sleeve 160 inside the blood vessel 473. To make this possible the cut-out 167 in the sleeve 160 is continued upwards to an adequate extent, as is also the corresponding cut-out 476 in suction tube 471. After the position described in FIG. 31 has been reached, the sleeve 160 can be pulled back up, after which the distal 483 and proximal 484 anchoring members are able to flip outwards under the influence of resilience so as to pierce the upper zone of the blood vessel 473 or at least to press into this. The anchoring members 483 and 484 can optionally pierce the blood vessel, certainly if it is taken into account that the suction nozzle 472, which can allow adequate room for this purpose at the ends of the anchoring members 483 and 484, is located on the outside of the blood vessel 473.

If the anastomosis produced is not an end-to-end anastomosis where the fixing device is positioned entirely intraluminally, as is shown here in FIG. 31, but an end-to-end anastomosis where the fixing device is positioned precisely on the end face of blood vessel 473, the suction nozzles 472 will have to make room for fingers 484 of the fixing device. This can be achieved by positioning the suction nozzles somewhat beyond the end face, somewhat more distally, or by making room for fingers 484 in these suction nozzles (not shown here).

As an alternative or as a supplement to the use of stabiliser 471 on the outside surface of target vessel 473, use can also be made of a stabiliser that is fed in through the proximal terminal or lateral opening in blood vessel 474 and through the fixing device 480 and on the distal side thereof is positioned on the inside of blood vessel 473 (not shown here). Such a stabiliser nozzle can then, for example, have a cylindrical shape comparable with insertion body 161, which then has to be removed by pulling back through the fixing device 480 after the vessel join has been produced.

With regard to FIGS. 29, 30 and 31 it is pointed out that the interacting stops on the stabiliser and applicator have not been shown here. However, these will be present in order to be able to guarantee the position with respect to one another. It is rather for retaining the clarity of the drawings that the instrument stop and stabiliser stop have been omitted.

As already indicated at the start of the description of FIG. 1, the stabiliser 1 shown in that figure is made up of a working duct 3 that is in the form of a tube. This working duct 3 is then provided with one or more suction nozzles at its distal end. A further advantage of such a tubular working duct essentially closed in the peripheral direction is that the working duct, insofar as this is in communication with the bloodstream at its distal end, provides an access route by means of which unnecessary blood loss outside the bloodstream can be counteracted. This can be achieved in particular if, with reference to FIG. 32, the working duct 533 is provided in one or more locations with one or more valves 500. The connection ports 501, which can consist of so-called Luer-lock joints, are ports which serve to vent the lumen of the working duct and/or to fill the working duct with fluid, such as infusion solutions, blood, optionally supplemented by medicaments, such as, for example, heparin. Ports 502, which can also consist of so-called Luer-lock joints can serve to perfuse the hollow wall of the vacuum duct itself with fluid at the end of the operation, by which means release of the vacuum duct can be promoted. The working duct 533 can be closed off at the proximal end by a cap 505. As far as the valves 500 are concerned, one or more flapping or sphincteral parts 500, for example made of rubber, silicone or silicone rubber or other plastics, can be provided inside the duct. An applicator or optionally another instrument can then easily be fed in through the working duct or stabiliser 533 via these sphincteral valves 500, optionally via a so-called guide wire. As is shown in FIG. 32, the working duct 533 is connected by means of a suction tube 504 to a vacuum source so as to be able to suck tightly to the wall of a blood vessel or hollow organ 503. The suction tube 504 is also provided with an instrument stop 506 that can be moved along it and can be adjustably locked by means of a rotary knob 507. By locking the instrument stop 506 in the correct position with respect to the suction tube 504 it is possible to ensure that the applicator or other instrument, not shown in FIG. 32, cannot be inserted too deeply into the working duct 533.

It will be clear that a working duct as shown in FIG. 32 can also be used in other locations. It is also conceivable to use such a working duct when fitting a valve in the heart. In such a case this working duct 533 will usually be fed to the heart via a relatively large blood vessel or via the wall of a heart chamber. If such an operation has to be carried out while the heart is beating, it can be advantageous to make the working duct 533 of perforated construction, at least as far as that section that is located in the bloodstream is concerned. The aim of this is to ensure that the blood is as far as possible still able to follow its normal route. With such a construction of the working duct 3 the valves 500 and ports 501 and 502 shown in FIG. 32 will be dispensed with, or at least will be able to be dispensed with, insofar as the working duct is at least in the bloodstream. The actual opening in the large blood vessel or in the wall of the heart chamber can be made by a hilum port fixing device that can be closed off by a cap, as has already been shown in a few figures in WO 00/44311 and has been described with reference to these. Such a port fixing device can have been positioned or can be positioned beforehand or at the end of the operation, usually within an external working duct that by means of its vacuum nozzle is in contact with the outside of the wall of the large blood vessel or the wall of the heart chamber concerned, around said opening.

The working duct shown in FIG. 32 can also be used for feeding in another working duct or a cannula through it. Said latter working duct or cannula can then itself be connected to a further fixing device. The other working duct to be fed in through the working duct 533 in FIG. 32 can optionally also once again be an (internal or inner) working duct 533 of a stabiliser for an assembly according to the invention. The external or outer working duct 533 is then mainly used as access route. In the case of a side join to another vessel or hollow organ 503, as shown in FIG. 32, it will then be possible to fix a port fixing device as shown in, for example, FIG. 8 in the passage formed in the blood vessel wall. At the end of the intervention, it will then be possible to fix a sealing cap in the fixing device, the various features being as already shown in a few figures in WO 00/44311 and described with reference to these. Furthermore, it will be clear that the so-called working duct can not only be made straight, as shown, but equally can also be made curved. With a view to adaptability to the circumstances, it is even preferable in this context if the working duct is made bendable, or at least flexible.

FIG. 33 shows, highly diagrammatically, part of the trunk of a human body with the thorax and the heart once again drawn diagrammatically therein. By way of example, three examples of working duct connections are also drawn diagrammatically. Working duct 515 is a working duct, for example corresponding to that shown in FIG. 32, that passes through the so-called second intercostal space, (between the 2nd and 3rd ribs) on the right-hand side of the body. Here the vacuum nozzle is on the aorta for, for example, an aortic valve operation, an aorta coronary bypass operation or the introduction of an arterial cannula for a heart/lung machine. The vacuum working duct 516, which once again can, for example, be constructed in accordance with that shown in FIG. 32, runs through the fourth intercostal space (between the 4th and the 5th ribs) on the right-hand side of the body. Here the vacuum nozzle is on the left atrium for, for example, a mitral valve operation. However, the vacuum nozzle can also be on the right atrium here for, for example, a tricuspid valve operation or the introduction of a venus cannula for a heart/lung machine. The vacuum working duct 517, which once again can, for example, be constructed in accordance with that shown in FIG. 32, runs through the 4th intercostal space (between the 4th and 5th ribs) on the left-hand side of the body. Here the vacuum nozzle relates to the left coronary artery for, for example, an aorta coronary bypass operation.

As will have been made clear, the present invention makes it possible not only to position the fixing device in a controlled manner at the desired distance at the location of or around the passage in the body tissue, but also to effect the desired turn and angular position. In this context the invention makes it possible to adapt the cross-section and/or shape of the passage in the body tissue to the cross-section and shape of the fixing device. The invention also makes it possible to work through small access routes, possibly without a direct view of the passage in the surrounding body tissue. Furthermore, the invention makes it possible to work, if desired, through closed working ducts so that there is no unnecessary loss of blood. The invention can also be used in operations on a beating heart without a heart/lung machine. Finally, the limited and simple mechanical actions and the controlled manner of these make the invention eminently suitable for (semi)automatic robotisation of the surgical intervention for which the invention is intended.

According to a further embodiment of the invention it is possible to construct the part of the stabiliser with the suction nozzle or nozzles such that it can be uncoupled from the rest of the stabiliser. This can, for example, be very useful if the suction nozzle section of the stabiliser can no longer be easily removed from the body following the operation, or possibly if it is intended to leave it in the body so that the suction nozzles continue to perform a specific function, such as providing the join made with extra rigidity, or permanently serving as a joining aid. In such a case this detachable suction nozzle section of the stabiliser can also be additionally fixed to a body part, for example vessel wall tissue, by other means. This can, for example, be effected by suturing or a mechanical join, including those as described in WO 00/24339 and WO 00/44311, both in the name of the same Applicant as the present application. However, a method that is very particularly advantageous according to the invention is to do this by means of an adhesive and specifically, in particular, a so-called tissue adhesive, such as, for example, fibrin adhesive, an acrylate adhesive, such as, for example, octyl cyanoacrylate, or a glutaraldehyde-resorcinol-formaldehyde adhesive, or a so-called BioGlue, or other tissue adhesive. The advantage of gluing joins according to the invention is that this can also be carried out in situations where the tissues have been pathologically changed, such as thickened, hardened and/or calcified, in which situations the use of mechanical joining means can be more difficult or impossible. Furthermore, the gluing technique according to the invention makes it possible not to introduce any foreign material into the bloodstream. In particular, inert materials tolerated by the body, such as are known from the state of the art, will then be used for the parts of the stabiliser remaining in the body. In this context consideration can be given to, for example, titanium or high grade stainless steel or nitinol. However, consideration can also be given in this context to diverse plastics, such as Teflon, silicones or (pyrolytic) carbon.

However, in this context it is also possible according to the invention to go a step further and, as it were, to integrate the stabiliser and applicator with fixing device. Specifically, it is also possible to use the vacuum nozzle section of the stabiliser left in the body as fixing means and completely or partially to dispense with the applicators and fixing devices to be positioned individually, which have been described in detail above. Three examples of this will be described with reference to the following FIGS. 34, 35 and 36.

FIG. 34 shows diagrammatically and in longitudinal section one example of adhesive joining means according to the invention for producing an end-to-side anastomosis. in FIG. 34 an end-to-side join is shown where donor vessel and target vessel make an angle of 90 degrees with respect to one another, but instead of being at right angles, this joining angle can also be inclined, such as, for example, at 45 degrees. Here the adhesive joining means consist of two bodies, i.e. a cylindrical body 601 for fixing to the bypass blood vessel 602 and a cylindrical body 603 for fixing to the receiving blood vessel 604. The first cylindrical body 601 is provided with a central opening 607 for accommodating the blood vessel 602. Blood vessel 602 can be introduced into cylindrical body 601 using an aid corresponding to insertion body 161 (see FIGS. 24-25), it then being possible for the suction nozzle to have a purely cylindrical shape or an ellipsoidal variant thereof, it being possible for fingers 168 to be dispensed with. The smaller the internal diameter of the blood vessel 602, and the diameter of the insertion body 161 must then also be smaller, the longer the relative length of insertion body 161 can then be made. The first cylindrical body 601 is also provided with a connection 605 for connection to a suction line. This connection 605 is in communication with a suction nozzle 606 or several suction nozzles 606 which are arranged distributed around the periphery of the internal passage of the cylindrical part 601 so as to suck tightly a blood vessel 602 that has been inserted in the accommodating opening 607. Such a suction nozzle 606 can consist of one or more compartments, which, for example, can run around the vessel, transversely, in the longitudinal direction, inclined, in a spiral or in another shape. At the bottom end the cylindrical body 601, or at least the accommodating opening 607, is provided with a tissue adhesive. The adhesive is on the inside of body 601, in any event close to the front end (distal end) of the bypass 602. This tissue adhesive can have been applied in advance but can also have been fed to the body 601 by means of an adhesive feed line 608 (which is thus optional). The adhesive feed line 608 can open into the passage 607 by means of one or more adhesive nozzles 616 similar to the suction nozzle 606. The adhesive feed line can also consist of the original vacuum line 605. Both the vacuum feed line(s) and the adhesive feed line(s) can be detachable from bodies 601 and 603. In a corresponding manner, the cylindrical body 603 has a accommodating opening 609 in which the body 601 can be inserted and joined. At the end facing the blood vessel 604, body 603 is provided with a semi-cylindrical, saddle-shaped flange 617. The flange 617 can equally well extend completely cylindrically around the entire periphery of blood vessel 604 if the blood vessel can be exposed all round. If blood vessel 604 is attached at both ends, a completely cylindrical flange 617 will in this case have to consist of at least two parts split in the lengthwise direction of blood vessel 604. A suction line 610, which is in communication with the suction nozzle 612, is connected to the body 603. The suction nozzle 612 runs around the hole 615 made in the receiving blood vessel 604. The outside of the blood vessel 604 is coated with a tissue adhesive 613 between the peripheral edge of the hole 615 and the suction nozzle 612. This tissue adhesive can be supplied via an adhesive feed 611. If present, the adhesive feed 611 will, like the adhesive feed 608, be able to dispense adhesive at the desired location by means of a line system and adhesive feed nozzles. After body 603 has been joined to blood vessel 604 in this way, lateral hole 615 can be made in vessel 604, it being possible to make use of the technique as described for FIGS. 19-21. Such a lateral hole 615 can also be made before positioning body 603, but it is then desirable to leave all or a number of the requisite accessories in place to prevent any adhesive passing into the lumen of blood vessel 604 via hole 615. After the body 601 has been joined to the blood vessel 602 and the body 603 has been joined to the blood vessel 604 in this way and opening 615 has been made therein, the body 601 can be inserted in the accommodating opening 609 of the body 603 and fixed thereto. Joining of bodies 601 and 603 to one another can take place in situ or remotely by making use of mutual stops, as have been described elsewhere in this publication, the other parts of one or more stabilisers, insofar as the bodies 606 and 603 are joined thereto, or on applicators suitable for temporarily holding bodies 601 and 603 tightly, or on both stabilisers and applicators. Many diverse coupling means are possible for fixing the body 601 to the body 603. It is also very readily conceivable, and is possibly even highly preferable, to produce this coupling as well by means of an adhesive join. After the adhesive 616 and 613 have completely set, the vacuum can be removed from the lines 603 and 605. According to the invention it is the case here that both body 601 and the front end of the wall of blood vessel 602 itself are in contact with the outside wall of blood vessel 604 and that only the inside wall (endothelium) of blood vessel 602 is against opening 615, as a result of which there is a maximum chance that a good intima-to-intima join is produced. If the blood vessel 602 has been inserted sufficiently far into the bottom of body 601, the blood vessel 602 will be able to start to grow together with the blood vessel 604. It should be clear that after the blood vessels 602 and 604 have grown together sufficiently a join has been obtained where no foreign material whatsoever that does not belong to the body extends into the bloodstream.

FIG. 35 shows a variant of FIG. 4 for producing an end-to-end anastomosis. Here there are essentially two cylindrical bodies similar to the cylindrical body 601 in FIG. 34. Therefore these bodies have been provided with corresponding reference numerals and the description of the components concerned is not repeated. The blood vessels to be joined end-to-end are indicated by 621 and 622. Here again it is advantageous to insert the blood vessels 621 and 622 sufficiently far through the respective cylindrical body 601 such that when the front ends of the cylindrical bodies 601 are moved towards one another and are positioned in contact with one another the front end edges of the blood vessels 621 and 622 come into contact with one another so as to be able to grow together in the course of time. Here again the blood vessels 621 and 622 can in the first instance be positioned in the cylindrical bodies 601 with the aid of an adapted insertion body 161 corresponding to the description for FIG. 34. Coupling means, such as the neck 666, will have been provided in order to hold the cylindrical bodies 601 fixed to one another. These coupling means can be of very diverse type and an average person skilled in the art will easily be able to work out details. The cylindrical bodies 601 can optionally also be glued together at their front ends. The bodies 601 will be pushed towards one another and fixed so that the tissue edges 671, which preferably have been folded over, are in contact with one another.

Both in the case of the end-to-side join (FIG. 34) and in the case of the end-to-end (FIG. 35) join it is possible to evert the terminal blood vessel over a terminal edge of the cylindrical body in order thus to bring even more intima tissue to the location of the front end of the cylindrical body. The folded-over part of the vessel wall can then likewise be sucked tightly and/or glued to the outside of the cylindrical body, which at that location can have suction and/or adhesive nozzles both on the inside and the outside.

FIG. 36 shows an example of adhesive joining means 650 for producing a side-to-side anastomosis. Here the accessories can consist of two cylindrical discs 656A and 656B which are essentially identical to one another and have circular cross-sections, but any other shapes that can be joined to one another are possible. On the side of the surfaces facing away from one another, these discs are provided with a recess 658, in which a blood vessel 651 or a blood vessel 652 can be laid, the various features being in accordance with what has been described with reference to FIGS. 27 and 28 as far as the intermediate part 402 there is concerned. The most important difference between the intermediate part 402 and the joining means 650 is that the intermediate part 402 is in one piece, whilst the joining means 650 are in two pieces and that the joining means 650, as stated, preferably have a circular cross-sectional shape. The circular cross-sectional shape makes it possible to be able to turn the parts 650 with respect to one another about the axis of rotation 653, at least in any event prior to the definitive join. In this way the position in which the blood vessels 651 and 652 cross one another can be set. The parts 650 are each provided with a connection for a suction line 657 (only 1 shown) which is in communication with suction nozzles 667, 668. These suction nozzles 667, 668 correspond to the suction nozzles 414 in FIG. 28. These suction nozzles can optionally also extend around the periphery and in the longitudinal direction of the vessels, parallel to the recesses, so that vessels 651 and 652 are accommodated in a vacuum duct. In this way the blood vessels 651 and 652 can be sucked tightly to parts the 656A and 656B. Between the suction nozzles 667, 668 and the central passage 655 the parts 650 are provided with a tissue adhesive which can be fed to that location, optionally via an adhesive feed duct 654 and adhesive nozzles 669, 670. With regard to making the openings in the blood vessels 651 and 652, reference is made to the corresponding description for FIGS. 27 and 28 and FIG. 34.

With reference to FIGS. 34, 35 and 36 it is pointed out that the adhesive nozzles are always shown closer to the existing passage, or passage that has been made or still has to be made, in the vessel wall than the vacuum nozzles. This mutual position of adhesive nozzles and suction nozzles can, however, also be reversed. The adhesive and suction nozzles can also be provided alternately around such a passage, or mixed between one another or alongside one another around such a passage.

With reference to FIGS. 34, 35 and 36 it is also pointed out that, on the one hand, for reasons of clarity and, on the other hand, because the adhesive joining means can also be used without this, the possibility of an assembly of one or more adhesive joining means with a guide rod fixed to one or more joining bodies, corresponding to guide rod 416 for an instrument stop 417 in FIG. 27, has not been shown in any of these drawings. With reference to FIGS. 34, 35 and 36 it is furthermore pointed out that the adhesive joining accessories have always been described as consisting of two parts. However, it is also readily conceivable to integrate the two parts into one part in each case. What then still remains is to place the respective blood vessels, if desired making use of an insertion part 161 adapted for this purpose, into the passages or recesses intended for this, to apply the vacuum and optionally to feed the tissue adhesive if this has not already been applied to the respective surfaces in advance. The adhesive joining accessories can also be such that the procedure is not first to position the one vessel in a separate accessory and then to position the other vessel in another separate accessory, but to position both vessels in one half of an accessory suitable for this purpose and then to join this half to the other half of the accessory. With this arrangement these accessories can be joined to one another by a movable joint, for example by using flexible plastics, the adhesive joining accessory only having to be flapped open, and after positioning the two vessels, can be flapped shut again. A mechanism of this type that flaps open and shut can also be used when positioning the two individual vessels in separate adhesive joining accessories, after which the two adhesive joining accessories can be joined to one another. In this sense the stabiliser bodies, of stabiliser 400, as described for FIGS. 27 and 28, if appropriate adapted by making use of several compartments or of separate adhesive feed ducts, can also be used in combination with gluing techniques.

To prevent kinking of the vessels due to the weight of the adhesive joining accessories or the edges thereof, it is preferable, especially in the case of side-to-side vessel joins, to fit the adhesive joining accessories, which in this case are usually separable, completely around the periphery of the vessel and/or to make these accessories tapered at the edges or otherwise to make the accessories bear on the tissue that may surround them.

A number of problems arise when gluing vessel joins together. Firstly, the vessels must be held in a stable position the correct distance apart and at the correct angle with respect to one another, not only while applying the adhesive but also thereafter. Secondly, complete squashing or constriction of the lumen of one or both vessels during administration of the adhesive must be prevented. Thirdly, no adhesive may enter the lumen itself and the passage between the two vessels must not be obstructed. In the case of adhesive techniques it is furthermore known that the adhesive cannot work well if the surfaces to be glued are not properly dry. In the case of blood vessels this means that there must be no blood on the surfaces to be glued. A gluing technique for a side-to-side anastomosis is described in WO 99/16359 and U.S. Pat. No. 6,245,083. In this technique the vessels are held together by temporarily introducing a balloon (of dual construction) into the lumen of both vessels through the respective openings. The adhesive is applied generously around the two vessels. However, feeding balloons into blood vessels is not always desirable or possible and can cause damage. The present invention makes it possible to stabilise both vessels by means of vacuum nozzles. The vacuum nozzles can be arranged around all or part of the periphery of the vessels, it being possible for the vacuum nozzles to be constructed in several parts, which can be brought towards one another by an adjustment mechanism and, if desired, can be joined to one another. The adhesive can be introduced into the vacuum nozzle through the vacuum duct or through a separate access route. The vacuum nozzle can consist of one or more compartments, as a result of which it becomes possible, for example, first to use all compartments to suck the vacuum nozzles tightly to the tissue in the first instance. The vacuum in the one half of the compartments is then, for example, removed and this half filled with adhesive. After this adhesive has set, the vacuum over the other half of the compartments is then also removed and, if desired or necessary, this half is also filled with adhesive, after which all adhesive joining accessories are completely fixed to the tissue. The adhesive feed connections and suction connections shown in FIGS. 34, 35 and 36 can then be in communication with the first and second series of compartments, respectively, and serve as suction line and/or adhesive feed line. Not only the vacuum nozzles, but also the adhesive nozzles can consist of various compartments, which may or may not be in communication with one another. If desired, separate adhesive feed lines can be used here if the adhesive consists of several components. Because the vessel wall tissue is always held tightly against the suction nozzle part when applying the adhesive, adhesive is prevented from being able to completely squash the vessel. In this case the adhesive also does not come into contact with blood because in the case of an end-to-side or side-to-side anastomosis the suction nozzle parts can first be glued to the separate unopened vessels before the requisite lateral opening is made in the vessel or vessels. The adhesive can then be placed around the existing opening, or opening that is to be made or has been made, in the tissue, such as a blood vessel, optionally the entire compartment or part of the compartment being used for vacuum and/or adhesive, but can also be applied to other parts of the adhesive joining accessories, such as the mutual contact surfaces and/or bearing zones on the surrounding tissue.

Although it is possible according to the invention first to glue the vessels to be joined to one another with the aid of vacuum nozzle/gluing accessories suitable for this purpose and then to make the mutual openings, it is also possible first to glue the individual vessels to such accessories and then, after making the requisite lateral opening(s) in the vessel walls, to join these accessories to one another, it then being easy to handle these accessories. The invention thus makes it possible first to position remotely, in a controlled manner, the adhesive joining accessories around existing openings, or openings that have been made or are to be made, in the walls of the vessels to be joined and to move parts of these adhesive joining accessories and/or the adhesive joining accessories with the vessels therein towards one another, if desired using an adjustment mechanism. Secondly, the invention ensures that the adhesive joining accessories and/or vessels are held in a stable position the correct distance apart and at the correct angle with respect to one another, not only when applying the adhesive but also thereafter. Thirdly, that the lumen of one or both vessels is not completely squashed or constricted during the administration of the adhesive. Fourthly, that no adhesive enters the lumen itself or the passage between the two vessels are obstructed. Fifthly, with the adhesive technique according to the invention the surfaces to be glued are always properly dry because the passage(s) in the wall of the blood vessel or blood vessels have to be made only after gluing. Sixthly, the invention makes it possible for a lateral opening to be made remotely, in a controlled manner, in the wall of a vessel or vessels which are surrounded by adhesive joining accessories. Seventhly, the invention provides for remote loading, in a controlled manner, of vessels into adhesive joining accessories.

The deformation or complete squashing of the vessel wall as a result of a possible surplus of adhesive or too high an administration pressure can furthermore be prevented by making use of administration means, such as (micro)pumps with a metered volume and/or metered pressure, as known from the state of the art, for the administration of the adhesive.

Of course, the adhesive technique and facilities for this purpose described here can also be used in combination with other fixing devices where components to be glued can have a completely or virtually completely circular shape, including those as described in WO 00/24339 and WO 00/44311, both in the name of the same Applicant as the present application, and in particular can also be used for fixing vessel fixing devices and/or rings in the case of a valve prosthesis ring, such as is used in the case of valve replacements and/or repairs of heart valves. Such components, including those as described in FIGS. 8, 16, 17 and 17b of this application, must then, however, be of double-walled (hollow) construction and be provided on at least one side with one or more suction nozzles, while such a component/such components must be provided with an access route for either a vacuum duct or hose or an adhesive administration duct or hose, or both. In the context of the invention such components can then be joined to the rest of the stabiliser such that they can be (un)coupled, but can also be used completely independently of the stabiliser.

It is also possible to use the adhesive joining accessories without using vacuum. The description for FIGS. 34-36 must then be so read that all vacuum nozzles and vacuum lines can also serve for applying adhesive or can be dispensed with. In this case also it is possible, without making use of a vacuum stabiliser, to move such adhesive joining accessories or components thereof apart and/or towards one another by means of an adjustment mechanism, which can be operated remotely and by means of mutual stops. If no vacuum is used the risk of deformation of the surface to be glued will increase. In this case it will usually be possible to combine the adhesive joining accessories with the use of methods for exerting counter-pressure on the tissue to be glued. Here, for example in the case of a vessel wall to be glued, use can be made of a probe, stent and/or balloon, for example positioned in the lumen of the vessel, which usually can be removed again after gluing, mostly through a change in shape.

Furthermore, it will also be clear that all actions described with regard to the stabilisers and applicators can not only be performed manually by the surgeon but also, exclusively or to support manual actions, with the aid of electric, hydraulic or pneumatic forms of drive, which may or may not be robotised.

Many variants of the present invention which fall within the scope of the claims are conceivable. For instance:
- the sleeve of the applicator, the working duct of the stabiliser and possibly also other components can be made transparent to afford a visual view of the location of the (surgical) intervention;
- the stabiliser and in particular the suction nozzles thereof can also be so equipped that they engage around a (tubular) wall of (vessel) tissue from the outside instead of from the inside; for example in the case of an aortic valve operation it is also possible by means of the stabiliser to suck the aorta tightly from the outside around the location of the valve;
- the components of the assembly according to the invention that come into contact with blood can be coated with anticoagulants and/or anti-infection agents and/or other medicaments and/or can be made of materials having such an action, such as, for example, (pyrolytic) carbon;
- the components of the assembly that come into contact with blood can be covered by materials, such as textile, such as, for example, Dacron or Teflon, or tissues from the body itself, which are well tolerated by the body, and, insofar as the components remain behind in the body, promote ingrowth of tissue and reduce the risk of blood clots;
- insofar as they remain behind in the body, the components and/or accessories described can, if desired, be produced completely or partially from material that is resorbable and/or soluble.
- the various stabilisers and instruments that have been described or fall within the scope of the claims and/or description can also be used independently of one another and in combinations other than the combinations mentioned, including combinations with other components known from the state of the art, including those that have been described in WO 00/24339 and WO 00/44311, both in the name of the same Applicant as the present application.
- the present invention can be employed in interventions both on a beating heart and on a heart that has been temporarily stopped;
- the present invention can be employed both in the case of heart operations with a closed thorax and in the case of heart operations with an opened and/or minimally opened thorax;
- the stabilisers and instruments can be given diverse dimensions, partly depending on the application. As far as the length of the stabiliser is concerned, lengths of 5 to 40 cm can be considered. As far as the diameter of the instruments is concerned, a diameter of 1 to 3 cm can be considered in the case of heart valve operations and diameters of 4 cm to less than 2 mm can be considered in the case of vessel joins.

The invention claimed is:

1. An assembly, comprising:
   a vacuum source;
   a tissue stabilizer comprising a tubular working duct and a loop-shaped suction nozzle;
   a suction line; and
   an instrument,
   the tubular working duct having a length and a diameter extending transverse to the length,
   the loop-shaped suction nozzle having a single suction opening extending over the entire circumference of the distal end of the working duct, said single suction opening being operationally connected to the vacuum source,
   the instrument being sized so as to be removably insertable through the tubular working duct, and
   the suction line extending from the vacuum source to the single suction opening, wherein the suction line is operationally separate from the working duct.

2. The assembly according to claim 1, further comprising a closure adapted for closing an axial passage through the working duct.

3. The assembly according to claim 1, wherein said single suction opening is an axial suction opening, which opens in the axial direction, viewed with respect to the working duct.

4. The assembly according to claim 1, wherein said single suction opening is a radial suction opening, opening in the radially outward direction, viewed with respect to the working duct.

5. The assembly according to claim 1, wherein said single suction opening is a radial suction opening, opening in the radially inward direction, viewed with respect to the working duct.

6. The assembly according to claim 1, wherein said single suction opening is an inclined suction opening, opening outwards obliquely with respect to the axial direction, viewed with respect to the working duct.

7. The assembly according to claim 1, wherein said single suction opening is an inclined suction opening, opening inwards obliquely with respect to the axial direction, viewed with respect to the working duct.

8. The assembly according to claim 1, wherein one or more valves are arranged within the working duct, which valves allow passage of said instrument.

9. The assembly according to claim 8, wherein the one or more valves comprise flapping or sphincteral parts.

10. The assembly according to claim 1, wherein the working duct is a hollow double walled working duct and wherein the suction line comprises a suction passage formed in the interior of the wall of the double walled working duct.

11. The assembly according to claim 1, wherein the suction line comprises at least one axial suction duct, the at least one axial suction duct being located in the wall of the working duct.

12. The assembly according to claim 1, wherein, when viewed in an axial direction, the working duct is curved.

13. The assembly according to claim 1, wherein, when viewed in an axial direction, the working duct is bendable or flexible.

14. The assembly according to claim 1, wherein the stabilizer is configured so as to allow the removable insertion of the instrument through the open proximal end of the working duct while the vacuum source is applying a vacuum to said single suction opening of the loop-shaped suction nozzle.

15. The assembly according to claim 1, wherein the instrument comprises a heart valve prosthesis and wherein the working duct is sized so as to enable insertion of the valve prosthesis through the tubular working duct.

16. The assembly according to claim 1, wherein the instrument has a diameter of 4 cm or less.

17. The assembly according to claim 1, wherein the instrument has a diameter of 1 to 3 cm.

18. The assembly according to claim 1, wherein the stabilizer and the instrument are provided with, respectively, an instrument stop provided on the stabilizer and a stabilizer stop provided on the instrument, which stops define a stop position when in contact with one another, and wherein, when the instrument is inserted through the proximal end of, and into, the working duct and the stops are in the stop position, the stops unambiguously define the position of a head section of the instrument with respect to the position of the loop-shaped suction nozzle.

19. The assembly according to claim 18, further comprising a guide on the stabilizer on which the instrument stop is provided such that it can slide along the guide and with respect to which the instrument stop can be locked, wherein the guide is provided at the proximal end of the working duct and has a direction of extension essentially transverse to the loop-shaped suction nozzle.

20. The assembly according to claim 19, wherein the stabilizer is provided with said guide, and wherein the suction nozzle and the guide are firmly linked to one another in such a way that the mutual positions of the loop-shaped suction nozzle and guide are fixed with respect to one another.

21. The assembly according to claim 20, wherein the guide is provided with a scale with a zero point and wherein the distance from the zero point to the loop-shaped suction nozzle is chosen such that when the instrument stop and stabilizer stop are in the stop position and aligned with the zero point, the head section is located at the distal end of the stabilizer.

22. The assembly according to claim 1, wherein the stabilizer further comprises a flange provided at the distal end of the working duct, said flange extending in a radially outward direction with respect to the working duct, and wherein the flange is provided with said single suction opening.

23. The assembly according to claim 1, wherein said single suction opening has a ring-shaped, circular, ellipsoidal, oval-like, tubular, saddle-shaped, 3-fold sine shaped, bean-shaped or kidney-shaped contour.

24. The assembly according to claim 1, wherein part of the suction line is accommodated in the wall of the working duct.

* * * * *

UNITED STATES PATENT AND TRADEMARK OFFICE
CERTIFICATE OF CORRECTION

PATENT NO. : 8,636,755 B2  Page 1 of 1
APPLICATION NO. : 10/510032
DATED : January 28, 2014
INVENTOR(S) : Eric Berreklouw It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1362 days.

Signed and Sealed this
Twenty-second Day of September, 2015

Michelle K. Lee
*Director of the United States Patent and Trademark Office*